US012626780B2

(12) United States Patent
Filippova et al.

(10) Patent No.: US 12,626,780 B2
(45) Date of Patent: May 12, 2026

(54) METHOD AND SYSTEM FOR SELECTING, MANAGING, AND ANALYZING DATA OF HIGH DIMENSIONALITY

(71) Applicant: GRAIL, Inc., Menlo Park, CA (US)

(72) Inventors: Darya Filippova, Sunnyvale, CA (US); Anton Valouev, La Canada, CA (US); Virgil Nicula, Cupertino, CA (US); Karthik Jagadeesh, San Francisco, CA (US); M. Cyrus Maher, San Mateo, CA (US); Matthew H. Larson, San Francisco, CA (US); Monica Portela dos Santos Pimentel, San Jose, CA (US); Robert Abe Paine Calef, Redwood City, CA (US)

(73) Assignee: GRAIL, Inc., Menlo Park, CA (US)

(*) Notice: Subject to any disclaimer, the term of this patent is extended or adjusted under 35 U.S.C. 154(b) by 1043 days.

(21) Appl. No.: 16/352,739

(22) Filed: Mar. 13, 2019

(65) Prior Publication Data

US 2019/0287649 A1 Sep. 19, 2019

Related U.S. Application Data

(60) Provisional application No. 62/642,461, filed on Mar. 13, 2018.

(51) Int. Cl.
*G16B 30/10* (2019.01)

(52) U.S. Cl.
CPC .................................. *G16B 30/10* (2019.02)

(58) Field of Classification Search
None
See application file for complete search history.

(56) References Cited

U.S. PATENT DOCUMENTS

| | | | |
|---|---|---|---|
| 6,466,923 B1 | 10/2002 | Young | |
| 8,642,349 B1 | 2/2014 | Yeatman et al. | |
| 8,706,422 B2 | 4/2014 | Lo et al. | |
| 9,260,745 B2 | 2/2016 | Rava et al. | |
| 9,373,059 B1 | 6/2016 | Heifets et al. | |
| 10,095,831 B2 | 10/2018 | Duenwald et al. | |
| 10,457,995 B2 | 10/2019 | Talasaz | |
| 10,741,269 B2 * | 8/2020 | Chudova | |
| 2003/0215120 A1 | 11/2003 | Uppaluri et al. | |
| 2010/0112590 A1 | 5/2010 | Lo et al. | |
| 2010/0145894 A1 | 6/2010 | Semizarov et al. | |
| 2012/0053253 A1 | 3/2012 | Stone et al. | |
| 2013/0034546 A1 | 2/2013 | Rava et al. | |
| 2013/0325360 A1 | 12/2013 | Deciu et al. | |
| 2014/0066317 A1 | 3/2014 | Talasaz | |
| 2014/0080715 A1 | 3/2014 | Lo et al. | |
| 2014/0100121 A1 | 4/2014 | Lo et al. | |
| 2014/0242588 A1 | 8/2014 | Van Den Boom et al. | |
| 2014/0371078 A1 | 12/2014 | Abdueva | |
| 2015/0102216 A1 | 4/2015 | Röder et al. | |
| 2015/0220838 A1 | 8/2015 | Martin et al. | |

| | | | |
|---|---|---|---|
| 2016/0002739 A1 | 1/2016 | Schutz et al. | |
| 2016/0232290 A1 | 8/2016 | Rava et al. | |
| 2016/0251704 A1 | 9/2016 | Talasaz et al. | |
| 2016/0364522 A1 | 12/2016 | Frey et al. | |
| 2017/0107576 A1 | 4/2017 | Babiarz et al. | |
| 2017/0121767 A1 | 5/2017 | Dor et al. | |
| 2017/0220735 A1 | 8/2017 | Duenwald et al. | |
| 2017/0240973 A1 | 8/2017 | Eltoukhy et al. | |
| 2017/0270245 A1 | 9/2017 | van Rooyen et al. | |
| 2017/0329893 A1 | 11/2017 | di Iulio et al. | |
| 2017/0342477 A1 | 11/2017 | Jensen et al. | |
| 2017/0342500 A1 | 11/2017 | Marquard et al. | |
| 2017/0362638 A1 | 12/2017 | Chudova et al. | |
| 2018/0046851 A1 | 2/2018 | Kienzle et al. | |
| 2018/0144261 A1 | 5/2018 | Wnuk et al. | |
| 2018/0148777 A1 | 5/2018 | Kirkizlar et al. | |
| 2018/0173845 A1 | 6/2018 | Sigurjonsson et al. | |
| 2019/0106737 A1 | 4/2019 | Underhill | |
| 2019/0131016 A1 | 5/2019 | Cohen et al. | |
| 2019/0164627 A1 | 5/2019 | Blocker et al. | |
| 2019/0287646 A1 | 9/2019 | Hubbell et al. | |
| 2019/0287649 A1 | 9/2019 | Filippova et al. | |
| 2019/0287652 A1 | 9/2019 | Gross et al. | |
| 2019/0316209 A1 | 10/2019 | Hubbell et al. | |
| 2020/0005901 A1 | 1/2020 | Cohen et al. | |
| 2020/0219587 A1 | 7/2020 | Hubbell | |
| 2020/0294624 A1 | 9/2020 | Filippova et al. | |
| 2020/0365229 A1 | 11/2020 | Fields et al. | |

(Continued)

FOREIGN PATENT DOCUMENTS

| | | |
|---|---|---|
| AU | 2015360298 | 6/2016 |
| WO | 2010/037001 A2 | 4/2010 |

(Continued)

OTHER PUBLICATIONS

Robinson, Peter N., Marten Jager, and Rosario Michael Piro. Computational Exome and Genome Analysis. First edition. Boca Raton, FL: CRC Press, 2017. Web.(2017) (Year: 2017).*

Clark, Travis A. et al. "Analytical Validation of a Hybrid Capture-Based Next-Generation Sequencing Clinical Assay for Genomic Profiling of Cell-Free Circulating Tumor DNA." The Journal of molecular diagnostics: JMD 20.5 (2018): 686-702. Web. (Year: 2018).*

Xia, Ligang et al. "Statistical Analysis of Mutant Allele Frequency Level of Circulating Cell-Free DNA and Blood Cells in Healthy Individuals." Scientific reports 7.1 (2017): 7526-7. Web and Supplemental (Year: 2017).*

Gunasegaran, Thineswaran, and Yu.-N Cheah. "Evolutionary Cross Validation." 2017 8th International Conference on Information Technology (ICIT). IEEE, 2017. 89-95. Web.(2017) (Year: 2017).*

Odegaard, Justin I et al. "Validation of a Plasma-Based Comprehensive Cancer Genotyping Assay Utilizing Orthogonal Tissue- and Plasma-Based Methodologies." Clinical cancer research 24.15 (2018): 3539-3549. Web. (Year: 2018).*

(Continued)

*Primary Examiner* — Karlheinz R. Skowronek
*Assistant Examiner* — Joseph Pulliam
(74) *Attorney, Agent, or Firm* — Bookoff McAndrews, PLLC

(57) ABSTRACT

A system, method and computer program product for analyzing data of high dimensionality (e.g., sequence reads of nucleic acid samples in connection with a disease condition) are provided.

17 Claims, 36 Drawing Sheets
(14 of 36 Drawing Sheet(s) Filed in Color)

(56) References Cited

U.S. PATENT DOCUMENTS

| | | |
|---|---|---|
| 2020/0372296 A1 | 11/2020 | Maher |
| 2021/0125683 A1* | 4/2021 | Zhou |
| 2021/0324477 A1 | 10/2021 | Xiang et al. |

FOREIGN PATENT DOCUMENTS

| | | |
|---|---|---|
| WO | WO 2010/051318 | 5/2010 |
| WO | 2011/127136 A1 | 10/2011 |
| WO | WO 2018/071621 | 6/2012 |
| WO | WO 2013/052907 | 4/2013 |
| WO | WO 2014/149134 | 9/2014 |
| WO | WO 2016/094853 | 12/2015 |
| WO | 2016/094853 A1 | 6/2016 |
| WO | WO 2017/161175 | 9/2017 |
| WO | WO 2017/181202 | 10/2017 |
| WO | WO 2017/212428 | 12/2017 |
| WO | 2018031929 A1 | 2/2018 |
| WO | WO 2018/022890 | 2/2018 |
| WO | WO 2018/022906 | 2/2018 |
| WO | 2018009723 A1 | 10/2018 |
| WO | WO 2019/084559 | 5/2019 |
| WO | WO 2019/232435 | 5/2019 |
| WO | WO 2021/119471 | 6/2021 |

OTHER PUBLICATIONS

Minarik, Gabriel et al. Utilization of Benchtop Next Generation Sequencing Platforms Ion Torrent PGM and MiSeq in Noninvasive Prenatal Testing for Chromosome 21 Trisomy and Testing of Impact of In Silico and Physical Size Selection on Its Analytical (Year: 2015).*

Kersaudy-Kerhoas, Maïwenn, and Elodie Sollier. "Micro-Scale Blood Plasma Separation: From Acoustophoresis to Egg-Beaters." Lab on a chip 13.17 (2013): 3323-3346. Web. (Year: 2013).*

Ulz, P., Thallinger, G. G., Auer, M., Graf, R., Kashofer, K., Jahn, S. W., Abete, L., Pristauz, G., Petru, E., Geigl, J. B., Heitzer, E., & Speicher, M. R. (2016). Inferring expressed genes by whole-genome sequencing of plasma DNA. Nature genetics, 48(10), 1273-1278. (Year: 2016).*

Smedley, D., Schubach, M., Jacobsen, . (2016). A Whole-Genome Analysis Framework for Effective Identification of Pathogenic Regulatory Variants in Mendelian Disease. American journal of human genetics, 99(3), 595-606. (Year: 2016).*

Hudecova, I., & Chiu, R. W. (2017). Non-invasive prenatal diagnosis of thalassemias using maternal plasma cell free DNA. Best practice & research. Clinical obstetrics & gynaecology, 39, 63-73. (Year: 2017).*

Enyedi, Márton Zsolt et al. "Simultaneous detection of BRCA mutations and large genomic rearrangements in germline DNA and FFPE tumor samples." Oncotarget 7.38 (2016): 61845-61859. Web. (Year: 2016).*

Leek and Storey, 2007, "Capturing Heterogeneity in Gene Expression Studies by Surrogate Variable Analysis," PLoS Genet 3, pp. 1724-1735.

Rumelhart et al., 1988, "Neurocomputing: Foundations of research," ch. Learning Representations by Back-propagating Errors, pp. 696-699, Cambridge, MA, USA: MIT Press.

Zeiler, 2012 "ADADELTA: an adaptive learning rate method," CoRR, vol. abs/212.5701.

U.S. Appl. No. 62/679,347, filed Jun. 1, 2018.

"U.S. Appl. No. 62/847,223, entitled Model-Based Featurization and Classification," filed May 13, 2019.

U.S. Appl. No. 62/851,486, entitled "Systems and Methods for Determining Whether a Subject Has a Cancer Condition Using Transfer Learning," filed May 22, 2019.

U.S. Appl. No. 62/827,682, entitled "Systems and Methods for Using Fragment Lengths as a Predictor of Cancer," filed Apr. 1, 2019.

Agresti, "An Introduction to Categorical Data Analysis" Chapter 5, John Wiley & Son, New York, 103-144, 1996.

Alkan, et al. Nat Genet 41, p. 1061-7, 2009.

Angermueller, Christof, et al. "DeepCpG: accurate prediction of single-cell DNA methylation states using deep learning", Genome Biology, 18(1), 2017.

Benjamin, et al., 2012, "Summaraizing and Correcting the GC Content Bias in High-Throughput Sequencing" Nucleic Acids Research, vol. 40, Issue 10, 1-14.

Boeva, et al. "Control-Free Calling of Copy Number Alternations in Deep-Sequencing Data using GC-Content Normalization", Bioinformatics, 27(2), 266-269.

Boser, et al., "A training algorithm for optimal margin classifiers", Proceedings of the 5th Annual ACM Workshop on Computational Learning Theory, ACM Press, Pittsburgh, Pa., 142-152, 1992.

Casadio, et al. "Urine cell-free DNA integrity as a marker for early bladder cancer diagnosis: preliminary data," Urol Oncol. 31(8), 1744-1750.

Chan, et al. "Clinical Sciences Reviews Committee of the Association of Clinical Biochemists Cell-free nucleic acids in plasma, serum and urine: a new tool in molecular diagnosis".

Chen, et al., "Conflict of CpG density and DNA methylation are proximally and distally involved in gene regulation in human and mouse tissues", Epgenetics 13(7), 721-741, 2018.

De Mattos-Arruda and Caldas, 2016, "Cell-free circulating tumour DNA as a liquid biopsy in breast cancer," Mol Oncol. 2016;10(3):464-474.

Du, et al., "Comparison of Beta-value and M-value methods for quantifying methylation levels by microarray analysis", BMC Bioinformatics 11, 587, 2010.

Duda, "Pattern Classification", Second Edition, John Wiley & Sons, Inc., 259, 262-265.

Fabregat, et al., "The Reactome Pathway Knowledgebase", Nucleic Acids Res., 46, D649-D655, 2018.

Frenel et al., 2015, Serial next-generation sequencing of circulating cell-free DNA evaluating tumor clone response to molecularly targeted drug administration. Clin Cancer Res. 21(20):4586-4596.

Furey, et al., "Support vector machine classification and validation of cancer tissue samples using microarray expression data", Bioinformatics 16, 906-914, 2000.

Goessl et al., "Fluorescent methylation-specific polymerase chain reaction for DNA-based detection of prostate cancer in bodily fluids," Cancer Res. 2000;60(21):5941-5945.

Gold, "Softmax to Softassign: Neural Network Algorithms for Combinatorial Optimization", Journal of Artificial Neural Networks 2, 381-399, 1996.

Hao et al., "Circulating cell-free DNA in serum as a biomarker for diagnosis and prognostic prediction of colorectal cancer," Br J Cancer. 2014; 111(8): 1482-1489.

Hassoun, "Fundamentals of Artificial Neural Networks", Massachusetts Institute of Technology, 1995.

Hastie, The Elements of Statistical Learning, Springer, New York, 2001.

Heitzer et al., 2013, "Establishment of tumor-specific copy number alterations from plasma DNA of patients with cancer," Int J Cancer. 133(2):346-356.

Heitzer et al., 2015, "Circulating tumor DNA as a liquid biopsy for cancer," Clin Chem. 61(1):112-123.

Hoadley, et al. "Multi-platform analysis of 12 cancer types reveals molecular classification within and across tissues-of-origin", Cell, 158(4). 929-944, 2014.

Jaccard, "Étude comparative de la distribution florale dans une portion des Alpes et des Jura", Bulletin de la Société vaudoise des sciences naturelles, 37 547-579, 1901.

Jaccard, "The Distribution of the flora in the alpine zone" New Phytologist, 11, 37-50, 1912.

Jenkinson, et al.,"Potential energy landscapes identify the information-theoretic nature of the epigenome", Nat. Genet. 49(5), 719-729, 2017.

Kanehisa, et al., KEGG: Kyoto Encyclopedia of Genes and Genomes, Nucleic Acids Res., 28(1), 27-30, 2000.

(56) References Cited

OTHER PUBLICATIONS

Kim et al., 2014, "Circulating cell-free DNA as a promising biomarker in patients with gastric cancer: diagnostic validity and significant reduction of clDNA after surgical resection," Ann Surg Treat Res. 2014;86(3): 136-142.

Kosub "A note on the triangle inequality for the Jaccard distance" arXiv:1612.02696.

Larochelle, et al., "Exploring strategies for training deep neural networks", J Mach Learn Res 10, 1-40, 2009.

Levandowsky, et al., "Distance between sets", Nature 234(5), 34-35, 1971.

Li, et al., "Mapping short DNA sequencing reads and calling variants using mapping quality scores", Genome Research, 18, 1852-8, 2008.

Lipkus, "A proof of the triangle inequality for the Tanimoto distance", Journal of Mathematical Chemistry, 26 (1-3), 263-265, 1999.

Liu, et al., "Bisulfite-free direct detection of 5-methylcytosine and 5-hydroxymethylcytosine at base resolution", Nature Biotechnology 37, 424-429, 2019.

Lo et al., 2010, "Maternal plasma DNA sequencing reveals the genome-wide genetic and mutational profile of the fetus," Sci Transl Med. 2(61):6lra91.

Miller, et al. "ReadDepth: A parallel R package for detecting copy numer alterations from short sequencing reads" PLOS One, vol. 6, 1-7, 2011.

Moulton, et al., "Maximally Consistent Sampling and the Jaccard Index of Probability Distributions", International Conference on Data Mining, Workshop on High Dimensional Data Mining, 2018.

Nuel, "Exact distribution of a pattern in a set of random sequences generated by a Markov source: applications to biological data", Algorithms for Molecular Biology 5(15, 2010.

Oxnard, et al. "Simultaneous Multi-cancer Detection and Tissue of Origin (TOO) Localization Using Targeted Bisulfite Sequencing of Plasma Cell-free DNA (cfDNA)", American Society of Clinical Oncology (ASCO) Breakthrough, Oct. 11-13, 2019, Bangkok, Thailand, 2019.

Poplin, Ryan, et al. "A universal SNP and small-indel variant caller using deep neural networks" Nature Biotechnology, 36(10), 2018.

Qian, et al., "Intelligent Surveillance Systems", Springer, 161, 2011.

Raptis and Menard, 1980, "Quantitation and characterization of plasma DNA in normals and patients with systemic lupus erythematosus," J Clin Invest. 66(6): 1391-1399.

Rogers, et al., "A Computer Program for Classifying Plants", Science 132(3434), 1115-1118, 1960.

Salvi et al., 2016, "Cell-free DNA as a diagnostic marker for cancer: current insights," Onco Targets Ther. 9:6549-6559.

Shao et al. 2015 "Quantitative analysis of cell-free DNA in ovarian cancer," Oncol Lett. 2015; 10(6):3478-3482.

Shapiro et al., 1983, "Determination of circulating DNA levels in patients with benign or malignant gastrointestinal disease," Cancer. 51(11):2116-2120.

Siegel et al., 2015, "Cancer statistics," CA Cancer J Clin. 65(1):5-29.

Sorber L. et al., J Mol Diagn., 19(1): 162-68 (2017).

Sozzi et al., 2003 "Quantification of free circulating DNA as a diagnostic marker in lung cancer," J Clin Oncol. 21(21):3902-3908.

Stroun et al., "Neoplastic characteristics of the DNA found in the plasma of cancer patients," Oncology. 1989;46(5):318-322).

Tan, et al., "Introduction to Data Mining", 2005.

Tanimoto, et al., "An Elementary Mathematical theory of Classification and Prediction", Internal IBM Technical Report, 1958.

Terry et al., 2016, "A prospective evaluation of early detection biomarkers for ovarian cancer in the European EPIC cohort," Clin Cancer Res. Apr. 8, 2016.

Vapnik, "Statistical Learning Theory", Wiley, New York, 1998.

Vincent, et al., "Stacked denoising autoencoders: Learning useful representations in a deep network with a local denoising criterion", J Mach Learn Res, 11, 3371-3408, 2010.

Yang, et al., "DistAl: An Inter-pattern Distance-based Constructive Learning Algorithm", Intelligent Data Analysis, 3(1), 55-83, 1999.

Yoon et al., 2009, Genome Research 19(9): 1586.

Yu, et al., "GaussianCpG: a Gaussian model for detection of CpG island in human genome sequences", BMC Genomics 18(4), 392, 2017.

Zhang, et al., "A novel method to quantify local CpG methylation density by regional methylation elongation assay on microarray", BMC Genomics 9:59, 9 pages, 2008.

Zhang, et al. "Tumor markers CA19-9, CA242 and CEA in the diagnosis of pancreatic cancer: a meta-analysis" Int J Clin Exp Med. 8(7), 11683-11691, 2015.

Zonta et al., "Assessment of DNA integrity, applications for cancer research," Adv Clin Chem. 2015;70: 197-246.

U.S. Appl. No. 62/642,507, filed Mar. 13, 2018, and entitled "Identifying Copy Number Aberrations" (67 pages).

Breiman, "Random Forests—Random Features", Technical Report 567, Sep. 1999, Statistics Department, U.C. Berkeley, pp. 1-29.

Nancy R. Cook, "Use and Misuse of the Receiver Operating Characteristic Curve in Risk Prediction", vol. 115, Issue 7, Feb. 20, 2007, pp. 928-935.

Richard O. Duda et al., "Pattern Classification and Scene Analysis", John Wiley & Sons, Inc., New York, Published in "A Wiley-Interscience . . . ", Sep. 1, 1974, Computer Science, 8 pages.

Clark et al., Analytical Validation of a Hybrid Capture-Based Next-Generation Sequencing Clinical Assay for Genomic Profiling of Cell-Free Circulating Tumor DNA, The Journal of Molecular Diagnostics, Elsevier, 2018 20(5), pp. 686-702.

Gunasegaran et al., Evolutionary Cross Validation, 2017 8th International Conference on Information Technology (ICIT), IEEE, 2017, pp. 89-95.

Kersaudy-Kerhoas et al., Micro-scale blood plasma separation: from acoustophoresis to egg-beaters, RSC Publishing, Lab on a Chip, 2013 13(17), pp. 3323-3346.

Minarik et al., Utilization of Benchtop Next Generation Sequencing Platforms Ion Torrent PGM and MiSeq in Noninvasive Prenatal Testing for Chromosome 21 Trisomy and Testing of Impact of In Silico and Physical Size Selection on Its Analytical Performance, 2015, 12 pages, PLoS One.

Odegaard et al., Validation of a Plasma-Based Comprehensive Cancer Genotyping Assay Utilizing Orthogonal Tissue- and Plasma-Based Methodologies, 2018, pp. 3539-3549, American Association for Cancer Research.

Robinson et al., Computational Exome and Genome Analysis, First edition, Boca Raton, FL: CRC Press, 2017, 575 pages.

Xia, Ligang et al., Statistical Analysis of Mutant Allele Frequency Level of Circulating Cell-Free DNA and Blood Cells in Healthy Individuals, Scientific Reports 7.1, pp. 2017, 7526-7527.

Kang et al., "CancerLocator: non-invasive cancer diagnosis and tissue-of-origin prediction using methylation profiles of cell-free DNA," Genome Biology, 2017, vol. 18, No. 53: pp. 1-12.

Changhong Shan, U.S. Appl. No. 62/642,506, filed Mar. 13, 2018, "Single Radio Voice Call Continuity (SRVCC) Handover and Return to Next Generation Radio Access Network (NG-RAN) After SRVCC" (54 pages).

I. T. Jolliffe, "Principal Component Analysis", Springer, New York © 2002, 518 pages.

Steven Kothen-Hill et al., "Deep Learning Mutation Prediction Enables Early Stage Lung Cancer Detection in Liquid Biopsy", Workshop track—ICLR 2018, 24 pages.

Aengus S. O'Marcaigh, et al., "Estimating the Predictive Value of a Diagnostic Test: How to Prevent Misleading or Confusing Results, Clinical Pediatrics", vol. 32, Issue 8, First Published Aug. 1, 1993, 7 pages.

Margaret Sullivan Pepe, et al., "Limitations of the Odds Ration in Gauging the Performance of a Diagnostic, Prognostic, or Screening Marker", American Journal of Epidemiology, American Journal of Epidemiology, vol. 159, Issue 9, May 1, 2004, pp. 882-890.

Alkes L. Price, et al., "Principal components analysis corrects for stratification in genome-wide association studies", vol. 38 No. 8, Aug. 2006, Nature Genetics, pp. 904-909.

(56)                    References Cited

OTHER PUBLICATIONS

Swanton, et al., "Phylogenetic ctDNA analysis depicts early stage lung cancer evolution", Nature. Apr. 26, 2017, Author manuscript; available in PMC Feb. 14, 2018; 545(7655), 446-451, 47 pages.

Yuchen Yuan et al., "DeepGene: an advanced cancer type classifier based on deep learning and somatic point mutations", Dec. 2016, BMC Bioinformatics 17(Suppl 17):476, 15 pages.

Zhao, et al., "Detection of fetal subchromosomal abnormalities by sequencing circulating cell-free DNA from maternal plasma", Clinical Chemistry, vol. 61, Issue 4, Apr. 1, 2015, pp. 608-616.

International Search Report and Written Opinion for International Application No. PCT/US2019/022139, mailed Jul. 11, 2019, 18 pages.

U.S. Appl. No. 62/818,013, filed Mar. 13, 2019, and entitled "Systems and Methods for Enriching for Cancer-Derived Fragments Using Fragment Size".

U.S. Appl. No. 62/679,347, filed Jun. 1, 2018, and entitled "Models for Targeted Sequencing".

Erickson R, "Somatic gene mutation and human disease other than cancer: An update", 2010, Mutat Res.;705 (2):96-106.

Erickson, "Somatic gene mutation and human disease other than cancer", 2003, Mutat Res., 543(2): pp. 125-136.

Trevor Hastie et al., "Chapter 9: Additive Models, Trees, and Related Models", The Elements of Statistical Learning, Second Edition, Springer Science+Business Media, LLC, 2009, pp. 295-336.

Alan Agresti, "Building and Applying Logistic Regression Models", An Introduction to Categorical Data Analysis, Second Edition, 2006, pp. 137-172.

Nello Cristianini et al., "An Introduction to Support Vector Machines and other kernel-based learning methods", Cambridge University Press, First Published 2000, pp. 93-124.

Karen Simonyan et al., "Very Deep Convolutional Networks for Large-Scale Image Recognition", Published as a conference paper at ICLR 2015, pp. 1-14.

International Search Report and Written Opinion mailed Sep. 13, 2019 in International Application No. PCT/US2019/034994 (20 pages).

International Search Report and Written Opinion mailed Mar. 9, 2021 in International Application No. PCT/US2020/064577 (13 pages).

* cited by examiner

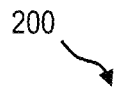
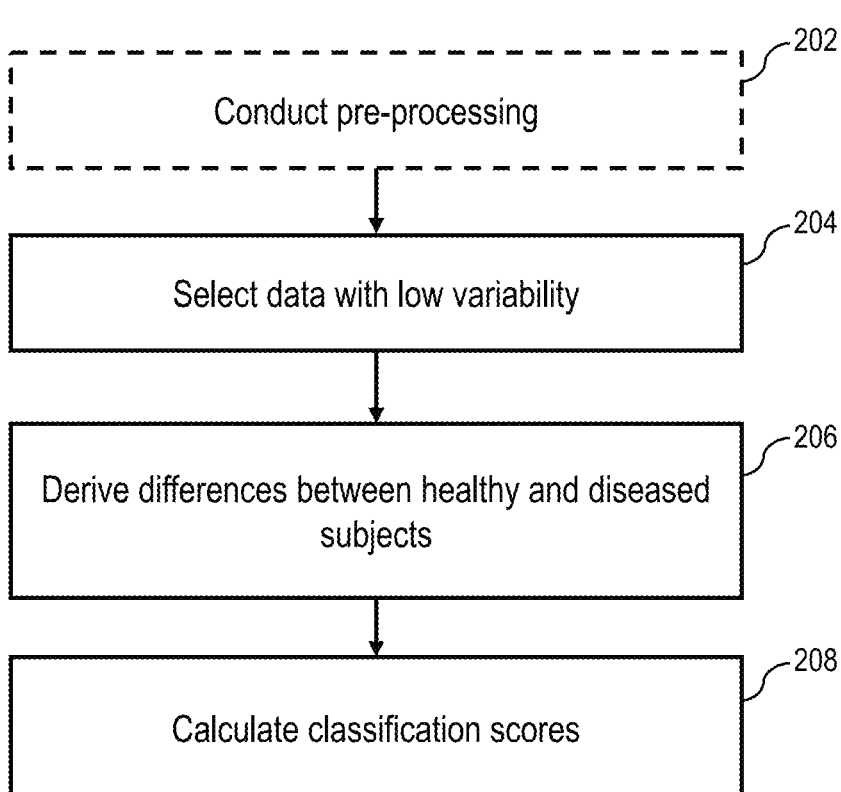
200
202
Conduct pre-processing
204
Select data with low variability
206
Derive differences between healthy and diseased subjects
208
Calculate classification scores
FIG. 2A

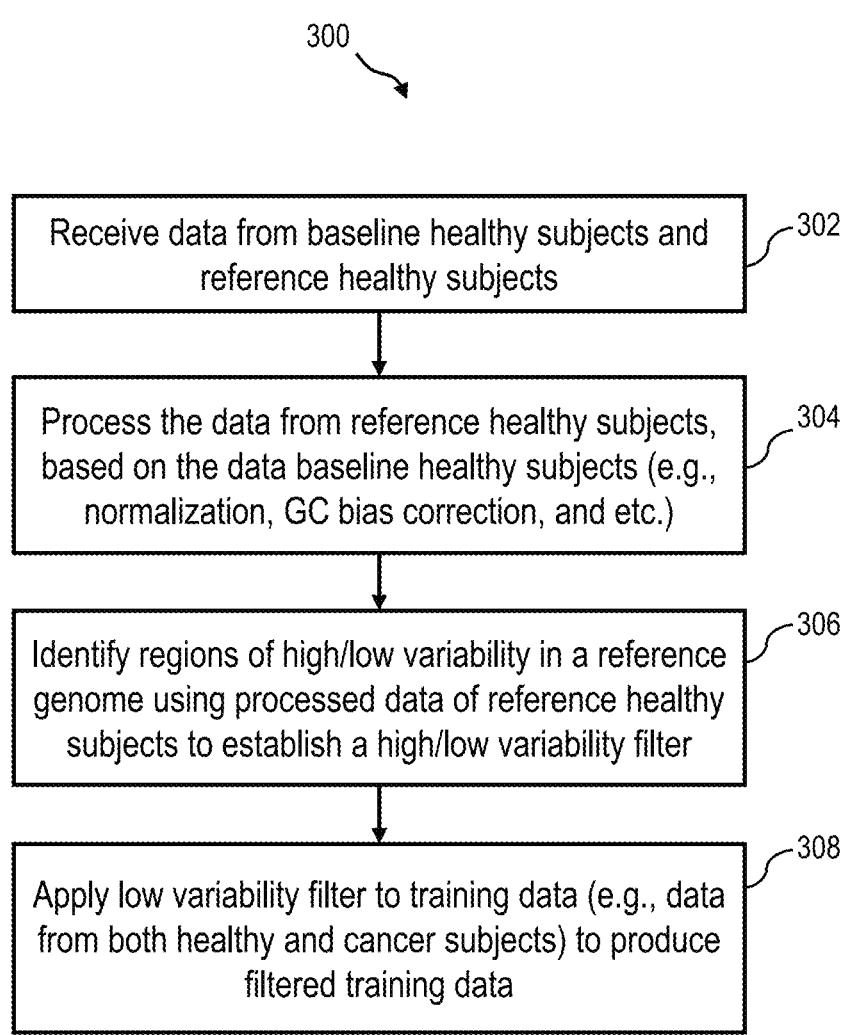

300

Receive data from baseline healthy subjects and reference healthy subjects ⌐302

Process the data from reference healthy subjects, based on the data baseline healthy subjects (e.g., normalization, GC bias correction, and etc.) ⌐304

Identify regions of high/low variability in a reference genome using processed data of reference healthy subjects to establish a high/low variability filter ⌐306

Apply low variability filter to training data (e.g., data from both healthy and cancer subjects) to produce filtered training data ⌐308

FIG. 3A

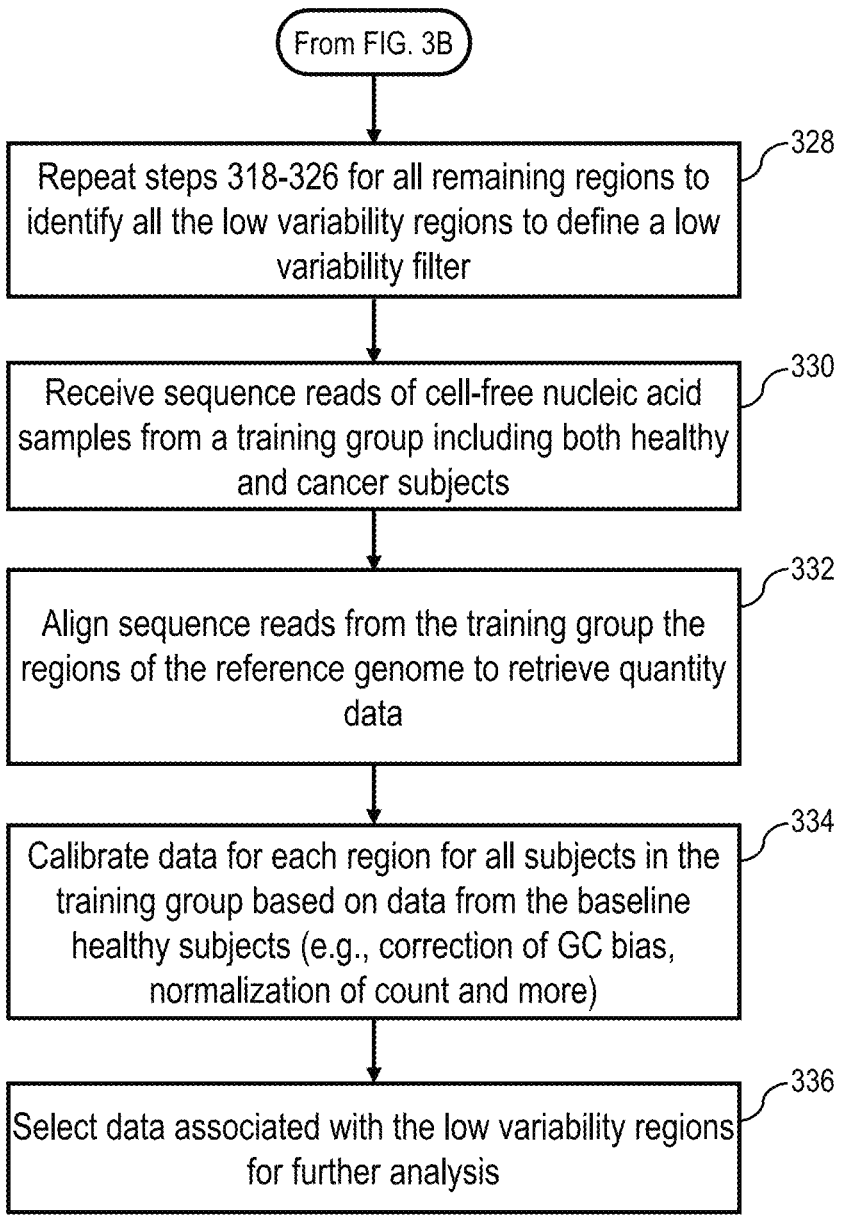

From FIG. 3B

Repeat steps 318-326 for all remaining regions to identify all the low variability regions to define a low variability filter ⟋328

Receive sequence reads of cell-free nucleic acid samples from a training group including both healthy and cancer subjects ⟋330

Align sequence reads from the training group the regions of the reference genome to retrieve quantity data ⟋332

Calibrate data for each region for all subjects in the training group based on data from the baseline healthy subjects (e.g., correction of GC bias, normalization of count and more) ⟋334

Select data associated with the low variability regions for further analysis ⟋336

FIG. 3C

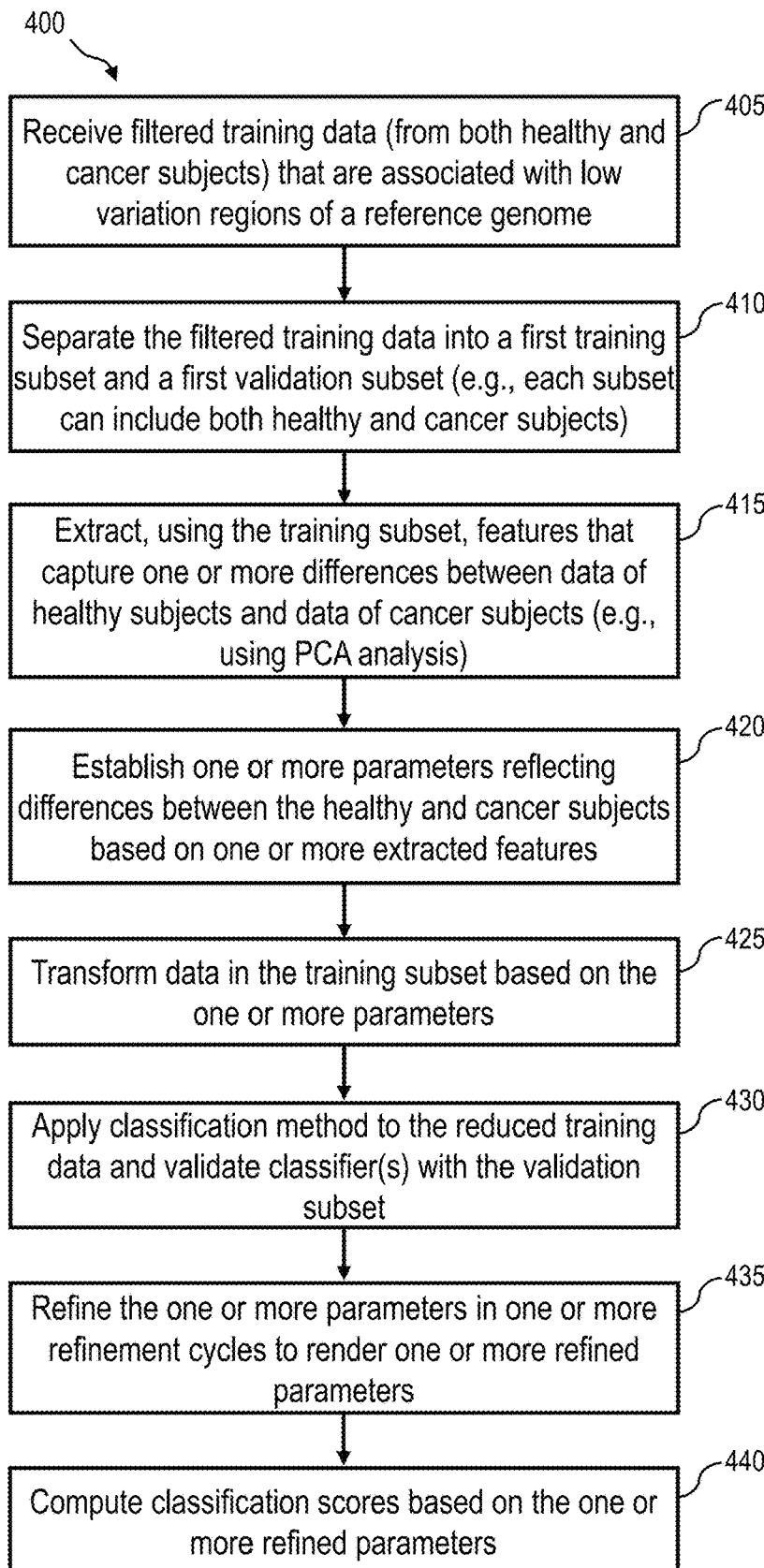

400

Receive filtered training data (from both healthy and cancer subjects) that are associated with low variation regions of a reference genome ⟋405

Separate the filtered training data into a first training subset and a first validation subset (e.g., each subset can include both healthy and cancer subjects) ⟋410

Extract, using the training subset, features that capture one or more differences between data of healthy subjects and data of cancer subjects (e.g., using PCA analysis) ⟋415

Establish one or more parameters reflecting differences between the healthy and cancer subjects based on one or more extracted features ⟋420

Transform data in the training subset based on the one or more parameters ⟋425

Apply classification method to the reduced training data and validate classifier(s) with the validation subset ⟋430

Refine the one or more parameters in one or more refinement cycles to render one or more refined parameters ⟋435

Compute classification scores based on the one or more refined parameters ⟋440

FIG. 4

| Type | Breast Cancer | | | | All |
|---|---|---|---|---|---|
| Stage | I | II | III | IV | N/A |
| Num. Samples | 86 | 82 | 28 | 5 | 359 |
| z-score<br>AUC<br>TPR @ 5% FPR<br>FPR @ 50% TPR | 0.45<br>0.04<br>0.60 | 0.56<br>0.16<br>0.48 | 0.71<br>0.47<br>0.19 | 0.94<br>0.80<br>0.01 | 0.60<br>0.21<br>0.37 |
| b-score<br>AUC<br>TPR @ 5% FPR<br>FPR @ 50% TPR | 0.57<br>0.03<br>0.37 | 0.61<br>0.19<br>0.28 | 0.80<br>0.52<br>0.03 | 0.99<br>1.00<br>0.01 | 0.68<br>0.25<br>0.25 |

FIG. 8

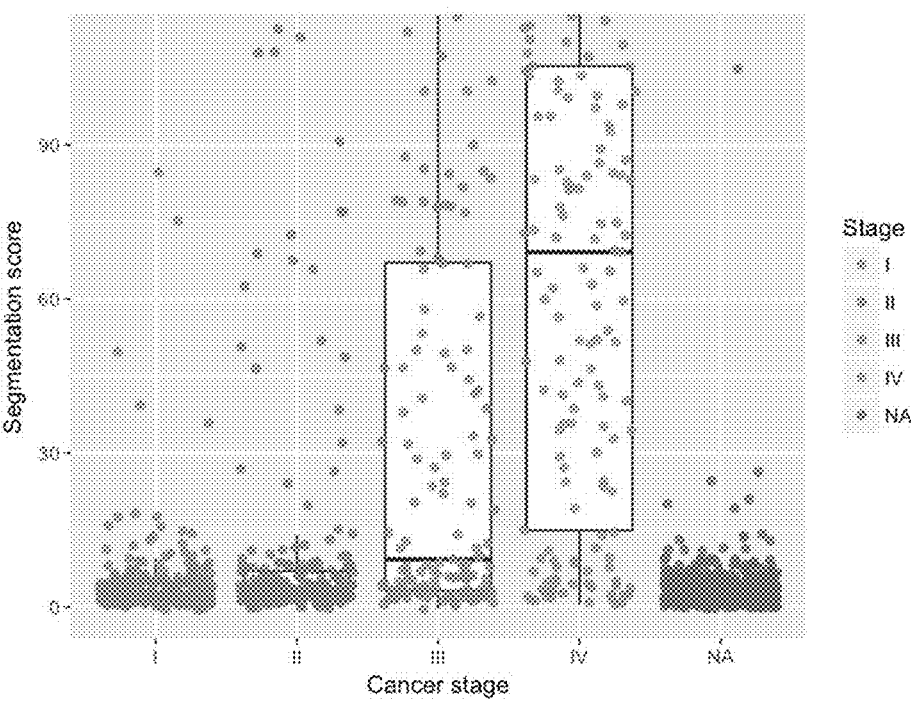
SCNA Segmentation Score/z-score vs Breast Cancer by Stage
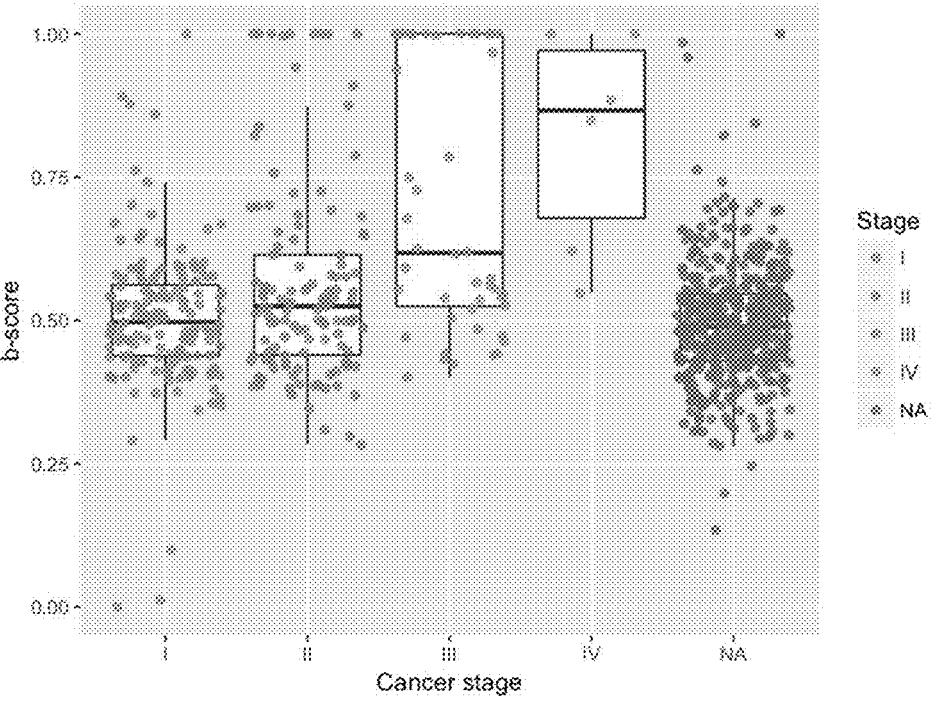
b-score performance on invasive breast cancer
FIG. 9

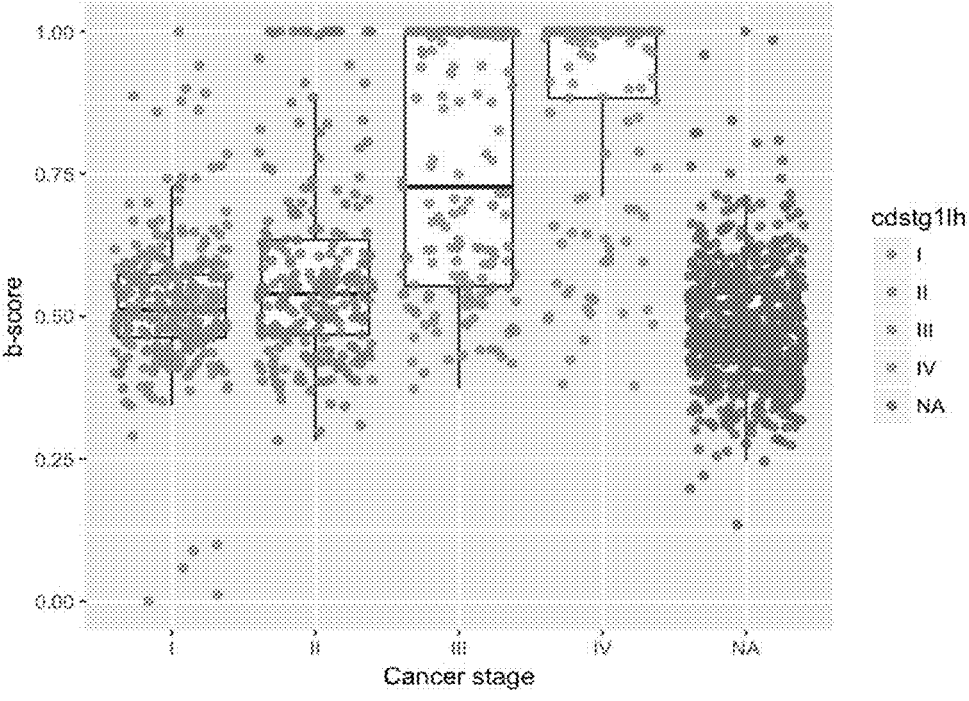
b-score performance on all cancers
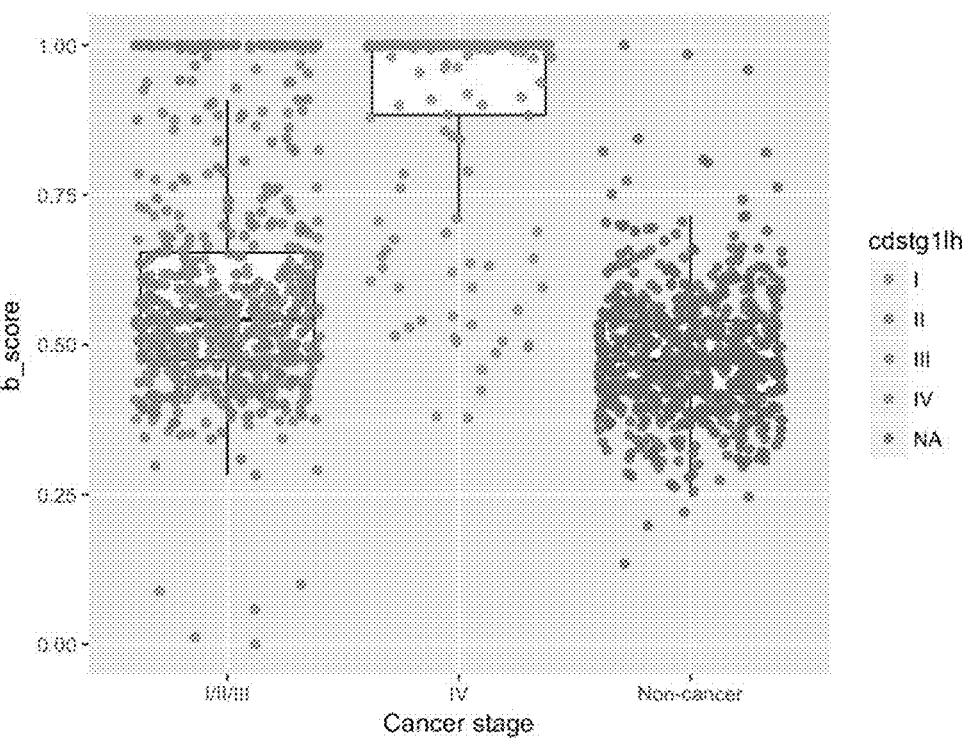
b-score performance on Stage I/II/III vs IV cancers
FIG. 10

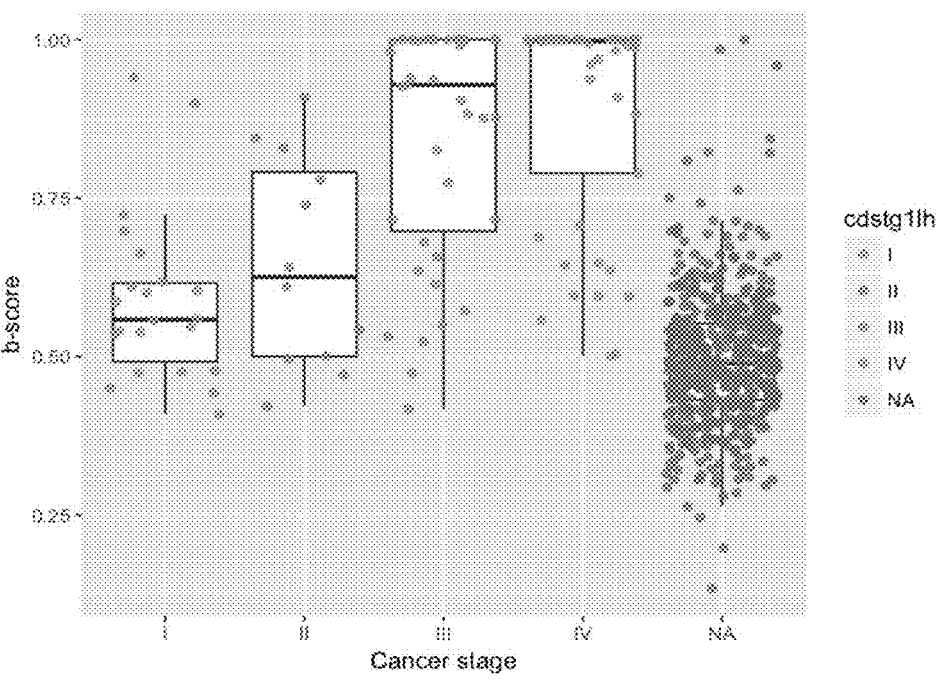
b-score performance on lung
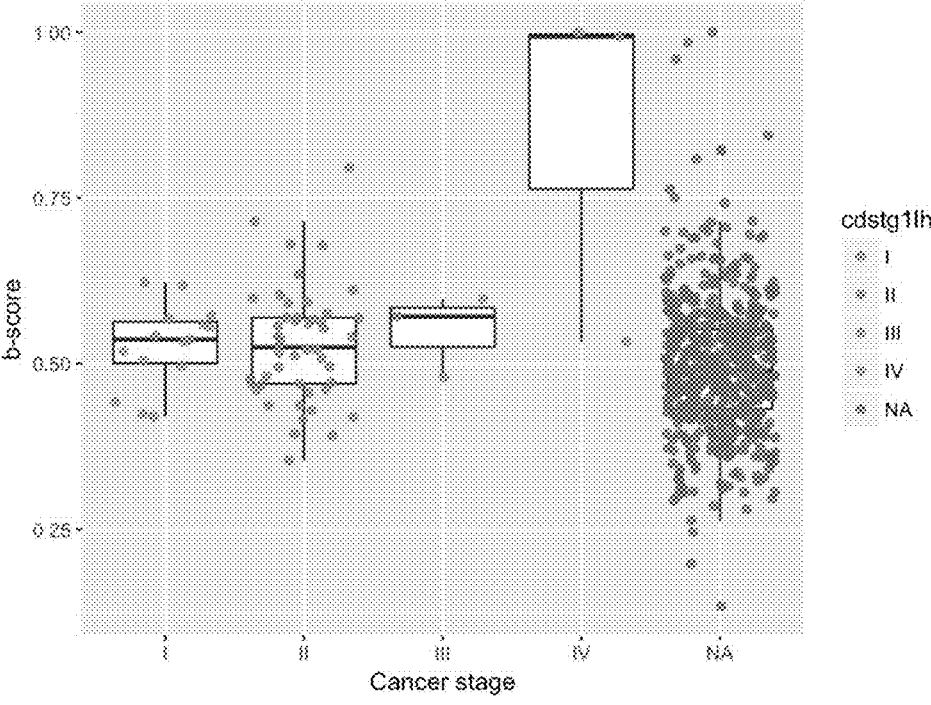
b-score performance on prostate cancer
FIG. 11A b-score performance on colorectal cancer

1300

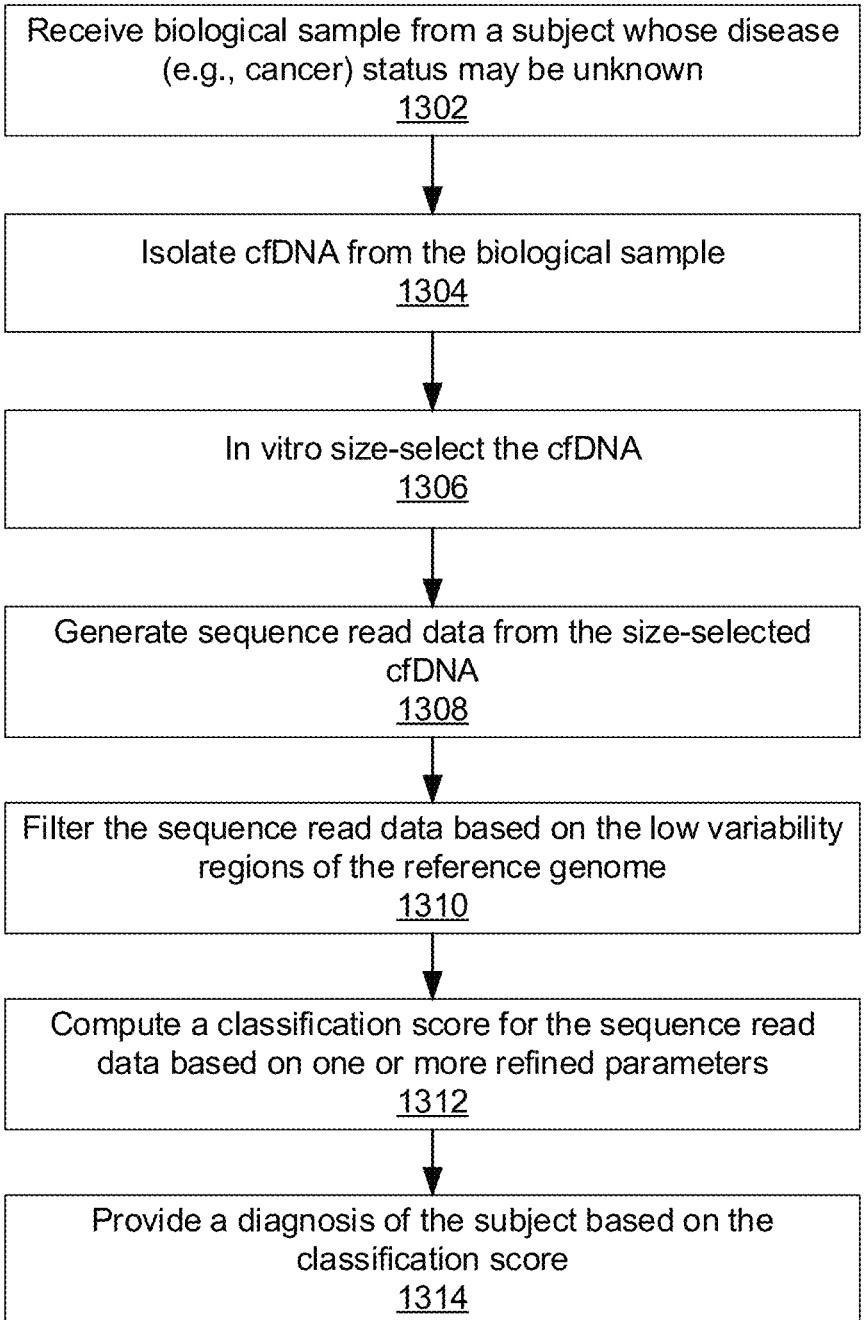

Receive biological sample from a subject whose disease
(e.g., cancer) status may be unknown
1302

Isolate cfDNA from the biological sample
1304

In vitro size-select the cfDNA
1306

Generate sequence read data from the size-selected
cfDNA
1308

Filter the sequence read data based on the low variability
regions of the reference genome
1310

Compute a classification score for the sequence read
data based on one or more refined parameters
1312

Provide a diagnosis of the subject based on the
classification score
1314

FIG. 13

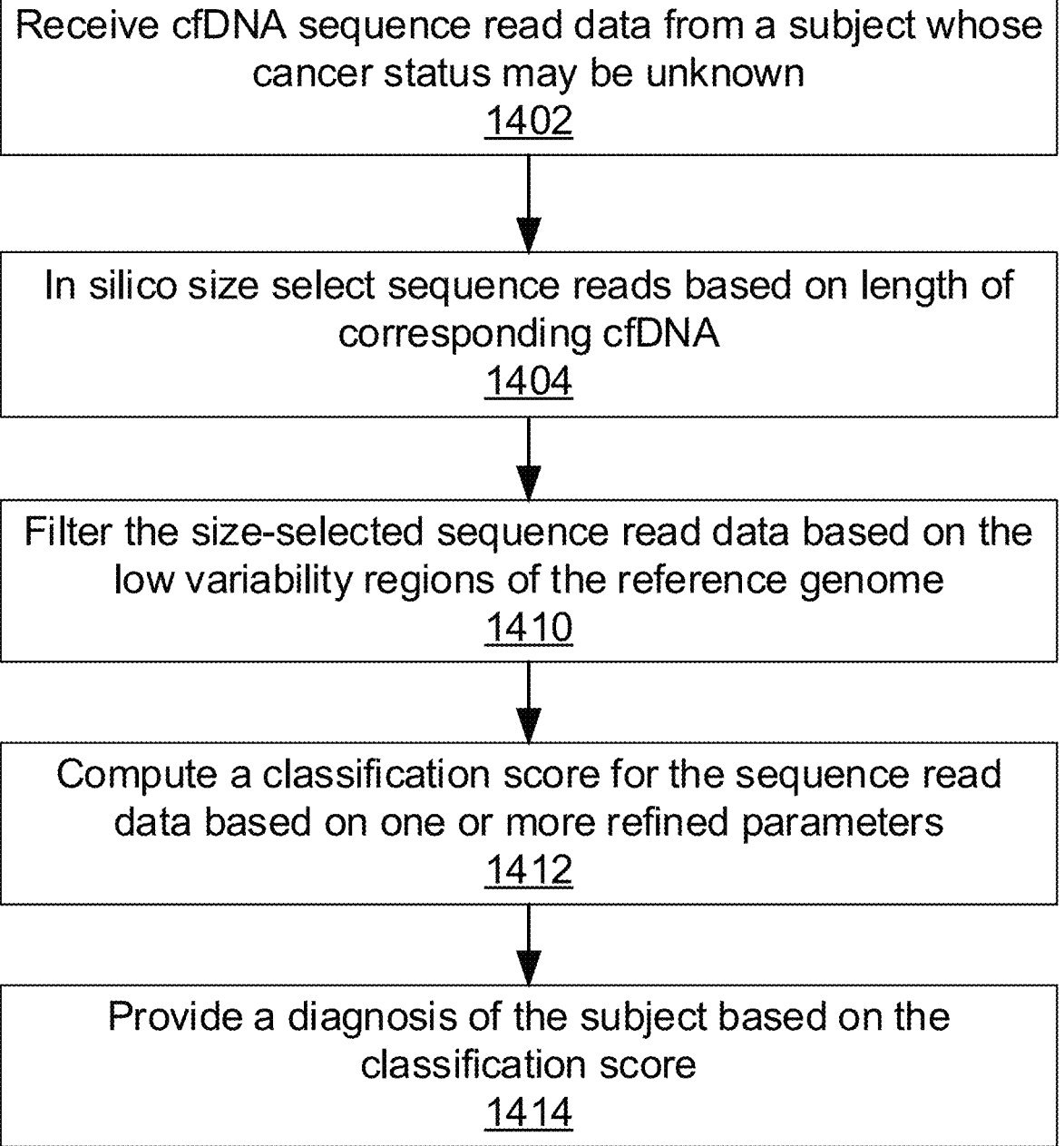

1400

Receive cfDNA sequence read data from a subject whose
cancer status may be unknown
1402

In silico size select sequence reads based on length of
corresponding cfDNA
1404

Filter the size-selected sequence read data based on the
low variability regions of the reference genome
1410

Compute a classification score for the sequence read
data based on one or more refined parameters
1412

Provide a diagnosis of the subject based on the
classification score
1414

FIG. 14 sens @ 95% spec

| Size select vs | Subsample | Full depth | Subsample | Full Depth | Subsample | Full depth | Subsample | Full depth | Subsample | Full depth |
|---|---|---|---|---|---|---|---|---|---|---|
| Stage | 0 | | I | | II | | III | | IV | |
| p-value | 0.08 | 0.01 | 0.24 | 0.85 | 2e-6 | 0.06 | 3e-7 | 8e-3 | 3e-4 | 0.5 |
| mean change (2.5%, 97.5% CI) | 0.036 (-0.005, 0.072) | 0.044 (0.010, 0.079) | 0.014 (-0.010, 0.039) | 0.002 (-0.024, 0.028) | 0.086 (0.055, 0.118) | 0.026 (-0.001, 0.055) | 0.105 (0.071, 0.141) | 0.035 (0.009, 0.061) | 0.047 (0.023, 0.071) | 0.006 (-0.012, 0.024) | sens @ 99% spec

| Size select vs | Subsample | Full depth | Subsample | Full Depth | Subsample | Full depth | Subsample | Full depth | Subsample | Full depth |
|---|---|---|---|---|---|---|---|---|---|---|
| Stage | 0 | | I | | II | | III | | IV | |
| p-value | 0.08 | 0.07 | 0.04 | 0.48 | 6e-6 | 7e-3 | 4e-8 | 6e-3 | 2e-5 | 4e-3 |
| mean change (2.5%, 97.5% CI) | 0.025 (-0.003, 0.052) | 0.025 (-0.003, 0.052) | 0.015 (0.000, 0.027) | 0.005 (-0.009, 0.018) | 0.063 (0.038, 0.087) | 0.031 (0.009, 0.053) | 0.123 (0.086, 0.160) | 0.059 (0.017, 0.099) | 0.061 (0.035, 0.087) | 0.030 (0.010, 0.051) |

FIG. 17E sens@ 95% spec

| Size select vs | Subsample | Full depth | Subsample | Full Depth | Subsample | Full depth | Subsample | Full depth | Subsample | Full depth |
|---|---|---|---|---|---|---|---|---|---|---|
| Stage | 0 | | I | | II | | III | | IV | |
| p-value | 0.34 | 0.01 | 0.15 | 0.82 | 3e-6 | 2e-3 | 1e-7 | 2e-3 | 8e-4 | 0.51 |
| mean change (2.5%, 97.5% CI) | 0.021 (-0.023, 0.065) | 0.044 (0.010, 0.079) | 0.028 (-0.010, 0.066) | 0.005 (-0.039, 0.049) | 0.144 (0.091, 0.198) | 0.070 (0.028, 0.112) | 0.115 (0.079, 0.151) | 0.043 (0.017, 0.069) | 0.047 (0.021, 0.074) | 0.006 (-0.013, 0.025) | sens@ 99% spec

| Size select vs | Subsample | Full depth | Subsample | Full Depth | Subsample | Full depth | Subsample | Full depth | Subsample | Full depth |
|---|---|---|---|---|---|---|---|---|---|---|
| Stage | 0 | | I | | II | | III | | IV | |
| p-value | 0.05 | 0.05 | 0.02 | 0.26 | 2e-5 | 2e-4 | 5e-10 | 4e-4 | 3e-5 | 2e-4 |
| mean change (2.5%, 97.5% CI) | 0.029 (0.001, 0.059) | 0.029 (0.001, 0.059) | 0.035 (0.005, 0.065) | 0.019 (-0.014, 0.052) | 0.121 (0.070, 0.171) | 0.085 (0.042, 0.128) | 0.142 (0.107, 0.178) | 0.075 (0.036, 0.114) | 0.070 (0.040, 0.100) | 0.040 (0.020, 0.059) |

METHOD AND SYSTEM FOR SELECTING, MANAGING, AND ANALYZING DATA OF HIGH DIMENSIONALITY

CROSS-REFERENCE TO RELATED APPLICATION

The present application claims the benefit of U.S. Provisional Application No. 62/642,461 filed Mar. 13, 2018, which is expressly incorporated herein by reference in its entirety for all purposes.

TECHNICAL FIELD

Disclosed herein are methods, systems and computing program products for selecting and analyzing biological data of high dimensionality, in particular, nucleic acid sequencing data obtained using next-generation sequencing technologies.

BACKGROUND

Modern development in biology, especially next-generation sequencing technologies, has generated vast amounts of data. Combing through the data for useful and helpful information, however, remains a big challenge, especially when such useful and helpful information is needed for disease diagnosis and prognosis. For example, the human genome includes over 3 billion base pairs of nucleic acid sequences. Although it is possible to obtain sequence reads of an entire human genome, much of the sequencing data encode information that is irrelevant to disease diagnosis and prognosis.

Ways of processing big data are needed in order to efficiently and accurately derive useful and relevant information.

SUMMARY

In one aspect, disclosed herein is a method of analyzing sequence reads of nucleic acid samples in connection with a disease condition. As disclosed herein, the method can comprise: identifying regions of low variability in a reference genome based on a first set of sequence reads of nucleic acid samples from each healthy subject in a reference group of healthy subjects, wherein each sequence read in the first set of sequence reads of nucleic acid samples from each healthy subject can be aligned to a region in the reference genome; selecting a training set of sequence reads from sequence reads of nucleic acid samples from subjects in a training group, wherein each sequence read in the training set aligns to a region in the regions of low variability in the reference genome, wherein the training set includes sequence reads of nucleic acid samples from healthy subjects and sequence reads of nucleic acid samples from diseased subjects who are known to have the disease condition, and wherein the nucleic acid samples from the training group are of a type that is the same as or similar to that of the nucleic acid samples from the reference group of heathy subjects; determining, using quantities derived from sequence reads of the training set, one or more parameters that reflect differences between sequence reads of nucleic acid samples from the healthy subjects and sequence reads of nucleic acid samples from the diseased subjects within the training group; receiving a test set of sequence reads associated with nucleic acid samples from a test subject whose status with respect to the disease condition is unknown; and predicting a likelihood of the test subject having the disease condition based on the one or more parameters.

In some embodiments, the nucleic acid samples comprise cell-free nucleic acid (cfNA) fragments.

In some embodiments, the disease condition is cancer.

In some embodiments, the disease condition is a cancer type selected from the group consisting of lung cancer, ovarian cancer, kidney cancer, bladder cancer, hepatobiliary caner, pancreatic cancer, upper gastrointestinal cancer, sarcoma, breast cancer, liver cancer, prostate cancer, brain cancer, and combinations thereof.

In some embodiments, the method further comprises: performing initial data processing of the first set of sequence reads of nucleic acid samples from each healthy subject in the reference group of healthy subjects based on sequence reads of nucleic acid samples from a baseline group of healthy subjects, wherein the reference group and the baseline group do not overlap, and wherein the initial data processing comprises correction of GC biases or normalization of numbers of sequence reads that align to regions of the reference genome.

In some embodiments, the method further comprises: performing initial data processing of the sequence reads of nucleic acid samples from each subject in the training group based on sequence reads of nucleic acid samples from a baseline group of healthy subjects, wherein the baseline group and the training group do not overlap, and wherein the initial data processing comprises correction of GC biases or normalization of numbers of sequence reads aligned to regions of the reference genome.

In some embodiments, the identifying regions of low variability in the reference genome further comprises: aligning sequences from the first set of sequence reads of nucleic acid samples from each healthy subject in the reference group of healthy subjects to a plurality of non-overlapping regions of the reference genome, the reference group having a first plurality of healthy subjects; deriving, for each healthy subject in the reference group, a quantity associated with sequence reads that align to a region within the plurality of non-overlapping regions of the reference genome, thereby rendering a first plurality of quantities corresponding to the region; determining a first reference quantity and a second reference quantity based on the first plurality of quantities; and identifying the region as having low variability when the first reference quantity and the second reference quantity satisfy a predetermined condition.

In some embodiments, the method further comprises: repeating the determining and identifying steps for all remaining regions in the plurality of non-overlapping regions of the reference genome, thereby identifying the regions of low variability in the reference genome.

In some embodiments, the selecting the training set of sequence reads from the sequence reads of nucleic acid samples from the training group further comprises: selecting sequence reads from the sequence reads of nucleic acid samples of the training group that align to the regions of low variability in the reference genome, thereby generating the training set of sequence reads.

In some embodiments, the determining one or more parameters comprises: deriving, for each subject in the training group and with respect to a region in the regions of low variability, one or more quantities based on the sequence reads that align to the region; repeating the deriving step for all remaining regions of low variability to render quantities corresponding to the regions of low variability for all subjects in the training group, wherein the quantities comprise a first subset of quantities relating to healthy subjects and a second subset of quantities relating to subjects known to have the disease condition; and determining the one or more parameters that reflect the differences between the first subset and second subset of quantities.

In some embodiments, the one or more quantities consist of one quantity corresponding to the total number of sequence reads that align to the region.

In some embodiments, the one or more quantities comprises multiple quantities each corresponding to a subset of the sequence reads that align to the region, wherein each sequence read within the same subset corresponds to nucleic acid samples having the same predetermined fragment size or size range, wherein sequence reads in different subsets correspond to nucleic acid samples having a different fragment size or size range.

In some embodiments, the one or more parameters are determined by principal component analysis (PCA).

In some embodiments, the method further comprises: refining the one or more parameters in a multi-fold cross-validation process by dividing the training set into a training subset and a validation subset.

In some embodiments, training and validation subsets in one fold of the multi-fold cross-validation process are different from different training and validation subsets in another fold of the multi-fold cross-validation process.

In some embodiments, the method further comprises: selecting sequence reads from sequence reads of the nucleic acid samples from the test subject that align to the regions of low variability in the reference genome, thereby generating the test set of sequence reads; and computing a classification score representing the likelihood of the test subject having the disease condition based on the test set of sequence reads and the one or more parameters.

In some embodiments, each of the regions of variability in the reference genome has a size between 10 k bp to 100 k bp. In some embodiments, each of the regions of variability in the reference genome has the same size. In some embodiments, the regions of variability in the reference genome do not have the same size.

In some embodiments, the one or more parameters are determined based on a subset of the training set of sequence reads.

In some embodiments, the sequence reads in the training set of sequence reads includes sequence reads of cell-free DNA (cfDNA) fragments in the nucleic acid samples from the subjects in the training group. The nucleic acid samples from the subjects in the training group include cfDNA fragments that are longer than a first threshold length, e.g., where the first threshold length is less than 160 nucleotides, and the sequence reads in the training set of sequence reads excludes sequence reads of cfDNA molecules that are longer than the first threshold length. In some embodiments, the first threshold length is 140 nucleotides or less.

In some embodiments, the sequence reads in the training set includes sequence reads of cfDNA fragments in the nucleic acid samples from the subjects in the training group having a length falling between a second threshold length and a third threshold length, where: the second threshold length is from 240 to 260 nucleotides, and the third threshold length is from 290 nucleotides to 310 nucleotides.

In some embodiments, the exclusion of sequence reads of cfDNA molecules that are longer than the first threshold length is achieved by physically separating cfDNA molecules from the subjects in the training group that are longer than the first threshold length from cfDNA molecules from the subjects in the training group that are shorter than the first threshold length.

In some embodiments, the exclusion of sequence reads of cfDNA molecules that are longer than the first threshold length is achieved by filtering out, in silico, sequence reads of cfDNA fragments from the nucleic acid samples from the subjects in the training group that are longer than the first threshold length.

Although described here with respect to a particular method for analyzing sequence reads of nucleic acid samples in connection with a disease condition, size selection of nucleic acid sequence reads, e.g., cfDNA sequence reads, can be applied in conjunction with any aspect of the present disclosure, e.g., with one or more of methods 200, 210, 300, 310, 400, 500, 600, 1200, 1300, and 1400. Further description of size-selection methods can be found, for example, in U.S. Provisional Application Ser. No. 62/818, 013, filed Mar. 13, 2019, and entitled SYSTEMS AND METHODS FOR ENRICHING FOR CANCER-DERIVED FRAGMENTS USING FRAGMENT SIZE, the content of which is incorporated herein by reference, in its entirety, for all purposes.

In one aspect, disclosed herein is a method of identifying regions of low variability in a reference genome based on sequencing data from healthy subjects in a reference group. For example, the method comprises: aligning sequences from a first set of sequence reads of nucleic acid samples from each healthy subject in the reference group to a plurality of non-overlapping regions of the reference genome, the reference group having a first plurality of healthy subjects; deriving, for each healthy subject in the reference group, a quantity associated with sequence reads that align to a region within the plurality of non-overlapping regions of the reference genome, thereby rendering a first plurality of quantities corresponding to the region; determining a first reference quantity and a second reference quantity based on the first plurality of quantities; and identifying the region of the reference genome as having low variability when the first reference quantity and the second reference quantity satisfy a predetermined condition.

In some embodiments, the method further comprises repeating the determining and identifying steps for all remaining regions in the plurality of non-overlapping regions of the reference genome, thereby identifying regions of low variability in the reference genome.

In some embodiments, the quantity corresponds to a total count of sequence reads of a healthy subject that align to the region.

In some embodiments, each of the sequence reads that align to the region further includes a predetermined genetic variation.

In some embodiments, each of the sequence reads that align to the region further includes an epigenetic modification. In some embodiments, the epigenetic modification includes methylation.

In some embodiments, the first reference quantity is selected from the group consisting of an average, a mean, a medium, a normalized average, a normalized mean, a normalized medium, and combinations thereof.

In some embodiments, the second reference quantity is selected from the group consisting of an interquartile range, a medium absolute deviation, a standard deviation, and combinations thereof.

In some embodiments, the predetermined condition comprises a difference between the first and second reference quantity being below a threshold value reflecting.

In one aspect, disclosed herein is a method of analyzing sequence reads of nucleic acid samples in connection with a disease condition. For example, the method comprises:

selecting a training set of sequence reads from sequence reads of nucleic acid samples from subjects in a training group, wherein each sequence read in the training set aligns to a region in a plurality of regions of low variability in a reference genome, wherein the training set includes sequence reads of healthy subjects and sequence reads of diseased subjects who are known to have the disease condition, and wherein the nucleic acid samples from the training group are of a type that is the same as or similar to that of the nucleic acid samples from the reference group of heathy subjects; determining, using quantities derived from sequence reads of the training set, one or more parameters that reflect differences between sequence reads of the healthy subjects and sequence reads of the diseased subjects within the training group; receiving a test set of sequence reads associated with a nucleic acid sample from a test subject whose status with respect to the disease condition is unknown; and predicting a likelihood of the test subject having the disease condition based on the one or more parameters.

In some embodiments, the sequence reads in the test set of sequence reads include sequence reads of cell-free DNA (cfDNA) fragments in the nucleic acid sample from the test subject. The nucleic acid sample from the test subject includes cfDNA fragments that are longer than a first threshold length, where the first threshold length is less than 160 nucleotides, and the sequence reads in the training set of sequence reads excludes sequence reads of cfDNA molecules that are longer than the first threshold length. In some embodiments, the first threshold length is 140 nucleotides.

In some embodiments, the sequence reads in the test set of sequence reads include sequence reads of cfDNA fragments in the nucleic acid sample from the test subject having a length falling between a second threshold length and a third threshold length, where: the second threshold length is from 240 to 260 nucleotides, and the third threshold length is from 290 nucleotides to 310 nucleotides.

In some embodiments, the exclusion of sequence reads of cfDNA molecules that are longer than the first threshold length is achieved by physically separating cfDNA molecules from the test subject that are longer than the first threshold length from cfDNA molecules from the test subject that are shorter than the first threshold length.

In some embodiments, exclusion of sequence reads of cfDNA molecules that are longer than the first threshold length is achieved by filtering out, in silico, sequence reads of cfDNA fragments from the nucleic acid sample from the test subject that are longer than the first threshold length.

Although described here with respect to a particular method for analyzing sequence reads of nucleic acid samples in connection with a disease condition, size selection of nucleic acid sequence reads, e.g., cfDNA sequence reads, can be applied in conjunction with any aspect of the present disclosure, e.g., with one or more of methods 200, 210, 300, 310, 400, 500, 600, 1200, 1300, and 1400.

In one aspect, disclosed herein is a method of analyzing sequence reads of nucleic acid samples in connection with a disease condition. For example, the method comprises: identifying regions of low variability in a reference genome based on a first set of sequence reads of nucleic acid samples from each healthy subject in a reference group of healthy subjects, wherein each sequence read in the first set of sequence reads of each healthy subject can be aligned to a region in the reference genome; selecting a training set of sequence reads from sequence reads of nucleic acid samples from subjects in a training group, wherein each sequence read in the training set aligns to a region in the regions of low variability in the reference genome, wherein the training set includes sequence reads of healthy subjects and sequence reads of diseased subjects who are known to have the disease condition, and wherein the nucleic acid samples from the training group are of a type that is the same as or similar to that of the nucleic acid samples from the reference group of heathy subjects; and determining, using quantities derived from sequence reads of the training set, one or more parameters that reflect differences between sequence reads of the healthy subjects and sequence reads of the diseased subjects within the training group.

In some embodiments, the sequence reads in the training set of sequence reads include sequence reads of cell-free DNA (cfDNA) fragments in the nucleic acid samples from the subjects in the training group. The nucleic acid samples from the subjects in the training group include cfDNA fragments that are longer than a first threshold length, where the first threshold length is less than 160 nucleotides, and the sequence reads in the training set of sequence reads excludes sequence reads of cfDNA molecules that are longer than the first threshold length. In some embodiments, the first threshold length is 140 nucleotides or less.

In some embodiments, the sequence reads in the training set includes sequence reads of cfDNA fragments in the nucleic acid samples from the subjects in the training group having a length falling between a second threshold length and a third threshold length, where: the second threshold length is from 240 to 260 nucleotides, and the third threshold length is from 290 nucleotides to 310 nucleotides.

In some embodiments, the exclusion of sequence reads of cfDNA molecules that are longer than the first threshold length is achieved by physically separating cfDNA molecules from the subjects in the training group that are longer than the first threshold length from cfDNA molecules from the subjects in the training group that are shorter than the first threshold length.

In some embodiments, exclusion of sequence reads of cfDNA molecules that are longer than the first threshold length is achieved by filtering out, in silico, sequence reads of cfDNA fragments from the nucleic acid samples from the subjects in the training group that are longer than the first threshold length.

Although described here with respect to a particular method for analyzing sequence reads of nucleic acid samples in connection with a disease condition, size selection of nucleic acid sequence reads, e.g., cfDNA sequence reads, can be applied in conjunction with any aspect of the present disclosure, e.g., with one or more of methods 200, 210, 300, 310, 400, 500, 600, 1200, 1300, and 1400.

In one aspect, disclosed herein is a computer system comprising: one or more processors; and a non-transitory computer-readable medium including one or more sequences of instructions. The sequences of instructions, that, when executed by the one or more processors, cause the processors to: identify regions of low variability in a reference genome based on a first set of sequence reads of nucleic acid samples from each healthy subject in a reference group of healthy subjects, wherein each sequence read in the first set of sequence reads of nucleic acid samples from each healthy subject can be aligned to a region in the reference genome; select a training set of sequence reads from sequence reads of nucleic acid samples from subjects in a training group, wherein each sequence read in the training set aligns to a region in the regions of low variability in the reference genome, wherein the training set includes sequence reads of nucleic acid samples from healthy subjects and sequence reads of nucleic acid samples from diseased subjects who are known to have the disease condition, and wherein the nucleic acid samples from the training group are of a type that is the same as or similar to that of the nucleic acid samples from the reference group of heathy subjects; determine, using quantities derived from sequence reads of the training set, one or more parameters that reflect differences between sequence reads of nucleic acid samples from the healthy subjects and sequence reads of nucleic acid samples from the diseased subjects within the training group; receive a test set of sequence reads associated with nucleic acid samples from a test subject whose status with respect to the disease condition is unknown; and predict a likelihood of the test subject having the disease condition based on the one or more parameters.

In one aspect, disclosed herein is a non-transitory computer-readable storage medium having stored thereon program code instructions that, when executed by a processor of a message management service, cause the message management service to perform a method that comprises: identifying regions of low variability in a reference genome based on a first set of sequence reads of nucleic acid samples from each healthy subject in a reference group of healthy subjects, wherein each sequence read in the first set of sequence reads of nucleic acid samples from each healthy subject can be aligned to a region in the reference genome; selecting a training set of sequence reads from sequence reads of nucleic acid samples from subjects in a training group, wherein each sequence read in the training set aligns to a region in the regions of low variability in the reference genome, wherein the training set includes sequence reads of nucleic acid samples from healthy subjects and sequence reads of nucleic acid samples from diseased subjects who are known to have the disease condition, and wherein the nucleic acid samples from the training group are of a type that is the same as or similar to that of the nucleic acid samples from the reference group of heathy subjects; determining, using quantities derived from sequence reads of the training set, one or more parameters that reflect differences between sequence reads of nucleic acid samples from the healthy subjects and sequence reads of nucleic acid samples from the diseased subjects within the training group; receiving a test set of sequence reads associated with nucleic acid samples from a test subject whose status with respect to the disease condition is unknown; and predicting a likelihood of the test subject having the disease condition based on the one or more parameters.

In one aspect, disclosed herein is a computer system comprising: one or more processors; and a non-transitory computer-readable medium including one or more sequences of instructions. The sequences of instructions, that, when executed by the one or more processors, cause the processors to: align sequences from a first set of sequence reads of nucleic acid samples from each healthy subject in the reference group to a plurality of non-overlapping regions of the reference genome, the reference group having a first plurality of healthy subjects; derive, for each healthy subject in the reference group, a quantity associated with sequence reads that align to a region within the plurality of non-overlapping regions of the reference genome, thereby rendering a first plurality of quantities corresponding to the region; determine a first reference quantity and a second reference quantity based on the first plurality of quantities; and identify the region of the reference genome as having low variability when the first reference quantity and the second reference quantity satisfy a predetermined condition.

In one aspect, disclosed herein is a non-transitory computer-readable storage medium having stored thereon program code instructions that, when executed by a processor of a message management service, cause the message management service to perform a method that comprises: aligning sequences from a first set of sequence reads of nucleic acid samples from each healthy subject in the reference group to a plurality of non-overlapping regions of the reference genome, the reference group having a first plurality of healthy subjects; deriving, for each healthy subject in the reference group, a quantity associated with sequence reads that align to a region within the plurality of non-overlapping regions of the reference genome, thereby rendering a first plurality of quantities corresponding to the region; determining a first reference quantity and a second reference quantity based on the first plurality of quantities; and identifying the region of the reference genome as having low variability when the first reference quantity and the second reference quantity satisfy a predetermined condition.

In one aspect, disclosed herein is a computer system comprising: one or more processors; and a non-transitory computer-readable medium including one or more sequences of instructions. The sequences of instructions, that, when executed by the one or more processors, cause the processors to: select a training set of sequence reads from sequence reads of nucleic acid samples from subjects in a training group, wherein each sequence read in the training set aligns to a region in a plurality of regions of low variability in a reference genome, wherein the training set includes sequence reads of healthy subjects and sequence reads of diseased subjects who are known to have the disease condition, and wherein the nucleic acid samples from the training group are of a type that is the same as or similar to that of the nucleic acid samples from the reference group of heathy subjects; determine, using quantities derived from sequence reads of the training set, one or more parameters that reflect differences between sequence reads of the healthy subjects and sequence reads of the diseased subjects within the training group; receive a test set of sequence reads associated with a nucleic acid sample from a test subject whose status with respect to the disease condition is unknown; and predict a likelihood of the test subject having the disease condition based on the one or more parameters.

In one aspect, disclosed herein is a non-transitory computer-readable storage medium having stored thereon program code instructions that, when executed by a processor of a message management service, cause the message management service to perform a method that comprises: selecting a training set of sequence reads from sequence reads of nucleic acid samples from subjects in a training group, wherein each sequence read in the training set aligns to a region in a plurality of regions of low variability in a reference genome, wherein the training set includes sequence reads of healthy subjects and sequence reads of diseased subjects who are known to have the disease condition, and wherein the nucleic acid samples from the training group are of a type that is the same as or similar to that of the nucleic acid samples from the reference group of heathy subjects; determining, using quantities derived from sequence reads of the training set, one or more parameters that reflect differences between sequence reads of the healthy subjects and sequence reads of the diseased subjects within the training group; receiving a test set of sequence reads associated with a nucleic acid sample from a test subject whose status with respect to the disease condition is unknown; and predicting a likelihood of the test subject having the disease condition based on the one or more parameters.

In one aspect, disclosed herein is a computer system comprising: one or more processors; and a non-transitory computer-readable medium including one or more sequences of instructions. The sequences of instructions, that, when executed by the one or more processors, cause the processors to: identify regions of low variability in a reference genome based on a first set of sequence reads of nucleic acid samples from each healthy subject in a reference group of healthy subjects, wherein each sequence read in the first set of sequence reads of each healthy subject can be aligned to a region in the reference genome; select a training set of sequence reads from sequence reads of nucleic acid samples from subjects in a training group, wherein each sequence read in the training set aligns to a region in the regions of low variability in the reference genome, wherein the training set includes sequence reads of healthy subjects and sequence reads of diseased subjects who are known to have the disease condition, and wherein the nucleic acid samples from the training group are of a type that is the same as or similar to that of the nucleic acid samples from the reference group of heathy subjects; and determine, using quantities derived from sequence reads of the training set, one or more parameters that reflect differences between sequence reads of the healthy subjects and sequence reads of the diseased subjects within the training group.

In one aspect, disclosed herein is a non-transitory computer-readable storage medium having stored thereon program code instructions that, when executed by a processor of a message management service, cause the message management service to perform a method that comprises: identifying regions of low variability in a reference genome based on a first set of sequence reads of nucleic acid samples from each healthy subject in a reference group of healthy subjects, wherein each sequence read in the first set of sequence reads of each healthy subject can be aligned to a region in the reference genome; selecting a training set of sequence reads from sequence reads of nucleic acid samples from subjects in a training group, wherein each sequence read in the training set aligns to a region in the regions of low variability in the reference genome, wherein the training set includes sequence reads of healthy subjects and sequence reads of diseased subjects who are known to have the disease condition, and wherein the nucleic acid samples from the training group are of a type that is the same as or similar to that of the nucleic acid samples from the reference group of heathy subjects; and determining, using quantities derived from sequence reads of the training set, one or more parameters that reflect differences between sequence reads of the healthy subjects and sequence reads of the diseased subjects within the training group.

In one aspect, one or more noise models are used to identify and exclude sequence reads that are noises; for example, sequence reads that may have resulted from a non-cancerous source. For example, copy number events can arise due to clonal hematopoiesis in white blood cells instead of resulting from somatic tumor cells. In some embodiments, copy number aberrations in cfNA samples are identified based on one or more noise models that are constructed using sequencing data from genomic nucleic acid samples; e.g., genomic DNA: (gDNA) obtained from white blood cells (WBCs) in the buffy coat.

In some embodiments, a WBC-based noise model is applied to further eliminate copy number events that are unrelated to somatic tumor cells. In some embodiments, the WBC-based noise model is applied as a part of the data pre-processing at step 202 in FIG. 2A. In some embodiments, the WBC-based noise model is applied after the data pre-processing step 202. In some embodiments, the WBC-based noise model is applied after the data selecting step 204 in FIG. 2A.

In one aspect, provided herein is a computer program product that comprises: a non-transitory computer-readable medium storing instructions for executing any method disclosed herein.

It will be understood that any one of the embodiments disclosed herein can be used in connection with any aspect of the disclosure, alone or in combination with one or more other embodiments.

It would be understood that any embodiments disclosed herein can be applied, when applicable, in any aspect of the invention, alone or in any combination.

Details of one or more implementations are set forth in the accompanying drawings and the description below. Other features, aspects, and potential advantages will be apparent from the description and drawings, and from the claims.

DESCRIPTION OF DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 2A depicts an example process, illustrating the overall method flow for processing data of high dimensionality.

FIG. 3A depicts a sample process for data selection.

FIG. 3C depicts a sample process for data selection.

FIG. 4 depicts a sample process for analyzing data to reduce data dimensionality.

FIG. 8 depicts exemplary results of the current method.

FIG. 9 depicts exemplary results of the current method.

FIG. 10 depicts exemplary results of the current method.

FIG. 11A depicts exemplary results of the current method.

FIG. 13 provides a flow chart for a method of determining a cancer status of a subject using in vitro size-selected cell-free DNA from a biological sample of the subject, in accordance with various embodiments of the present disclosure.

FIG. 14 provides a flow chart for a method of determining a cancer status of a subject using in silico size-selected sequence reads of cell-free DNA from a biological sample of the subject, in accordance with various embodiments of the present disclosure.

FIG. 17E shows cancer-stage dependent statistics for the classifications shown in FIGS. 16C and 16D using in silico size-selected sequence reads, as described in Example 7.

FIG. 17H shows cancer-stage dependent statistics for classifications shown in FIGS. 17F and 17G using in silico size-selected sequence reads, as described in Example 7.

Like reference symbols in the various drawings indicate like elements.

DETAILED DESCRIPTION

Definitions

Figure 1A:
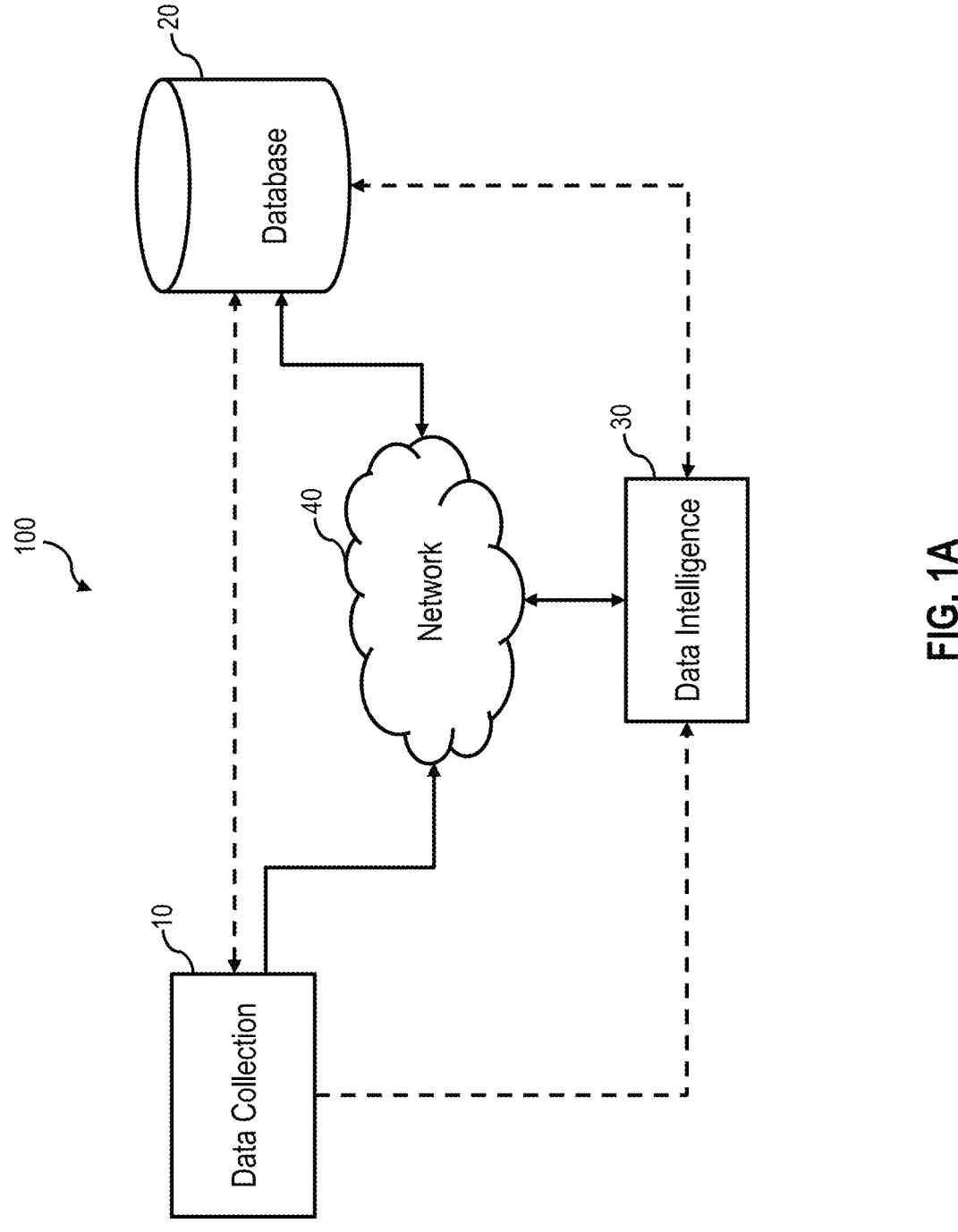
FIG. 1A depicts a sample system for processing data of high dimensionality.

As disclosed herein, the term "data of high dimensionality" refers to data sets that are so voluminous and complex that traditional data processing application software are inadequate to deal with them. For example, an average human genome includes about 20,000 genes, which are encoded in over 3.2 billion base pair of nucleic acid sequences per haploid genome and about 6.5 billion base pair of nucleic acid sequences per diploid genome. In some embodiments, a large number of samples can also lead to high data dimensionality even though the data collected from each sample may be limited. As disclosed herein, "data of high dimensionality" can include targeted sequencing data, whole genome sequencing data, sequencing data revealing epigenetic modifications (e.g., methylation), and combinations thereof. In some embodiments, "data of high dimensionality" can include nucleic acid sequencing data and protein sequencing data. In some embodiments, "data of high dimensionality" can include non-biological data. Nucleic acid sequencing data are used as illustration throughout the disclosure, which should not be construed as a limitation of the scope of the disclosure.

As disclosed herein, the term "subject" refers to any living or non-living organism, including but not limited to a human (e.g., a male human, female human, fetus, pregnant female, child, or the like), a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female of any stage (e.g., a man, a women or a child).

As disclosed herein, the term "biological sample" refers to any sample taken from a subject, which can reflect a biological state associated with the subject. Examples of biological samples include but are not limited to a tissue sample, a hair sample, a blood sample, a serum sample, a plasma sample, a tear sample, a sweat sample, a urine sample, a saliva sample, and etc. In some embodiments, a biological sample includes nucleic acid molecules such as DNA or RNA. In some embodiments, a biological sample includes protein molecules.

As used herein, the terms "nucleic acid" and "nucleic acid molecule" are used interchangeably. The terms refer to nucleic acids of any composition form, such as deoxyribo-nucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, super- coiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome or fragment thereof (e.g., a nucleic acid sample may be from one chromosome of a sample obtained from a diploid organism). In certain embodiments nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. A nucleic acid may be prepared using a nucleic acid obtained from a subject as a template.

As disclosed herein, the term "cell-free nucleic acids" refers to nucleic acid molecules that can be found outside cells, in bodily fluids such blood, sweat, urine, or saliva. Cell-free nucleic acids are used interchangeably as circulating nucleic acids. Examples of the cell-free nucleic acids include but are not limited to RNA, mitochondrial DNA, or genomic DNA.

As disclosed herein, the terms "sequencing", "sequence determination" and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment or an RNA fragment.

As disclosed herein, the term "sequencing data" refers to any data where sequence information is determined. Sequencing data can be obtained by a variety of technologies, including but not limited to high-throughput sequencing systems such as the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used in high-throughput sequencing approaches. For example, nucleic acid sequencing technology that may be used in a method described herein is sequencing-by-synthesis and reversible terminator-based sequencing (e.g., Illumina's Genome Analyzer; Genome Analyzer II; HISEQ 2000; HISEQ 2500 (Illumina, San Diego Calif.)). With this technology, millions of nucleic acid (e.g., DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments, a nucleic acid sample can include a signal or tag that facilitate detection. Sequencing data include quantification information of the signal or tag via a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

As disclosed herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp.

As disclosed herein, the term "fragment size" refers to the size of a nucleic acid molecule within a biological sample. In nucleic acid samples derived from cellular material, nucleic acid molecules have larger sizes. Sometimes, methods such as sonication need to be applied to break down the nucleic acid molecules into smaller fragments. In cell-free biological samples, nucleic acid molecules tend to be smaller in size.

As disclosed herein, the term "reference genome" refers to to any particular known, sequenced or characterized genome, whether partial or complete, of any organism or virus which may be used to reference identified sequences from a subject. For example, a reference genome used for human subjects as well as many other organisms can be found in on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As disclosed herein, the term "regions of a reference genome," "genomic region," or "chromosomal region" refers to any portion of a reference genome, contiguous or non-contiguous. It can also be referred to, for example, as a bin, a partition, a genomic portion, a portion of a reference genome, a portion of a chromosome and the like. In some embodiments, a genomic section is based on a particular length of genomic sequence. In some embodiments, a method can include analysis of multiple mapped sequence reads to a plurality of genomic regions. Genomic regions can be approximately the same length or the genomic sections can be different lengths. In some embodiments, genomic regions are of about equal length. In some embodiments genomic regions of different lengths are adjusted or weighted. In some embodiments, a genomic region is about 10 kilobases (kb) to about 500 kb, about 20 kb to about 400 kb, about 30 kb to about 300 kb, about 40 kb to about 200 kb, and sometimes about 50 kb to about 100 kb. In some embodiments, a genomic region is about 100 kb to about 200 kb. A genomic region is not limited to contiguous runs of sequence. Thus, genomic regions can be made up of contiguous and/or non-contiguous sequences. A genomic region is not limited to a single chromosome. In some embodiments, a genomic region includes all or part of one chromosome or all or part of two or more chromosomes. In some embodiments, genomic regions may span one, two, or more entire chromosomes. In addition, the genomic regions may span joint or disjointed portions of multiple chromosomes.

As disclosed herein, the term "alignment to a region of a reference genome" refer to a process of matching sequences from one or more sequence reads to that of the reference genome based on complete or partial identity between the sequences. Alignments can be done manually or by a computer algorithm, examples including the Efficient Local Alignment of Nucleotide Data (ELAND) computer program distributed as part of the Illumina Genomics Analysis pipeline. The alignment of a sequence read can be a 100% sequence match. In some embodiments, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand. In some embodiments a nucleic acid sequence is aligned with the reverse complement of another nucleic acid sequence.

As disclosed herein, the term "copy number variation" refers to variation in the number of copies of a nucleic acid sequence present in a test sample in comparison with the copy number of the nucleic acid sequence present in a qualified sample (e.g., a control sample with known status with respect to a certain medical condition). In certain embodiments, copy number variations occur in nucleic acid sequences of 1 kb or smaller. In certain embodiments, copy number variations occur in nucleic acid sequences of 1 kb or larger. In some cases, the nucleic acid sequence is a whole chromosome or significant portion thereof. A "copy number variant" refers to the sequence of nucleic acid in which copy-number differences are found by comparison of a sequence of interest in test sample with an expected level of the sequence of interest. For example, the level of the sequence of interest in the test sample is compared to that present in a qualified sample. Copy number variants/variations include deletions, including microdeletions, insertions, including microinsertions, duplications, multiplications, inversions, translocations and complex multi-site variants. CNVs encompass chromosomal aneuploidies and partial aneuploidies.

Additional details concerning relevant technologies and terminology can be found, for example, in U.S. Pat. Pub. No. 2013/0325360; U.S. Pat. Pub. No. 2013/0034546; U.S. Pat. No. 8,706,422; and U.S. Pat. Pub. No. 2010/0112590, each of which is incorporated herein in its entirety.

The term "individual" refers to a human individual. The term "healthy individual" refers to an individual presumed to not have a cancer or disease. The term "cancer subject" refers to an individual who is known to have, or potentially has, a cancer or disease.

The term "sequence reads" refers to nucleotide sequences read from a sample obtained from an individual. Sequence reads can be obtained through various methods known in the art.

The term "cell free nucleic acid," "cell free DNA," or "cfDNA" refers to nucleic acid fragments that circulate in an individual's body (e.g., bloodstream) and originate from one or more healthy cells and/or from one or more cancer cells.

The term "genomic nucleic acid," "genomic DNA," or "gDNA" refers to nucleic acid including chromosomal DNA that originates from one or more healthy (e.g., non-tumor) cells. In various embodiments, gDNA can be extracted from a cell derived from a blood cell lineage, such as a white blood cell.

The term "copy number aberrations" or "CNAs" refers to changes in copy number in somatic tumor cells. For example, CNAs can refer to copy number changes in a solid tumor.

The term "copy number variations" or "CNVs" refers to changes in copy number changes that derive from germline cells or from somatic copy number changes in non-tumor cells. For example, CNVs can refer to copy number changes in white blood cells that can arise due to clonal hematopoiesis.

The term "copy number event" refers to one or both of a copy number aberration and a copy number variation.

Exemplary System Embodiments

FIG. 1A depicts an exemplary system for processing data of high dimensionality. Exemplary system 100 includes a data collection component 10, a database 20 and device data intelligence component 30, connected to each other via network 40. Alternatively, or additionally, one or more of the components can be connected with another component locally without reliance on network connection; e.g., through a wired connection. Sequencing data of cell-free nucleic acids are used to illustrate the concepts. However, one of skill in the art would understand that the current method can be applied to sequencing data of other materials or non-sequencing data as well.

As disclosed herein, data collection component 10 can include a device or machine with which big data or data of high dimensionality are generated. In some embodiments, data collection component 10 can include a sequencing machine or a facility that uses a sequencing machine to generate nucleic acid sequence data of biological samples. Any applicable biological samples can be used. In some embodiments, a biological sample is cell-based; for example, one or more types of tissue. In some embodiments, a biological sample is a sample that includes cell-free nucleic acid fragments. Examples of biological samples include but are not limited to a blood sample, a serum sample, a plasma sample, a urine sample, a saliva sample, and etc.

Example of sequencing data can include but are not limited to sequence read data of targeted genomic locations, partial or whole genome sequencing data of genome represented by nucleic acid fragments in cell-free or cell-based samples, partial or whole genome sequencing data including one or more types of epigenetic modifications (e.g., methylation), or combinations thereof.

Figure 1B:
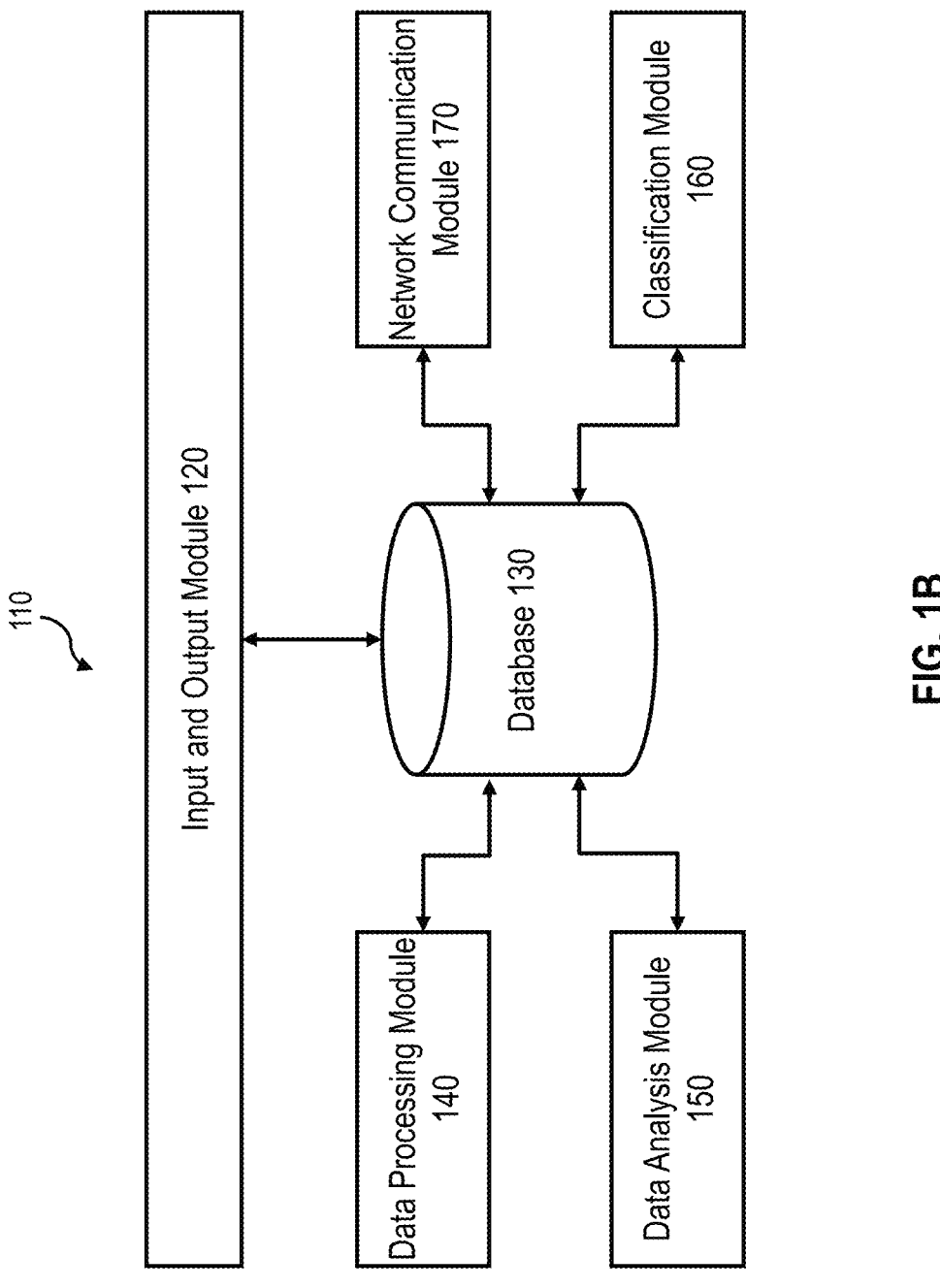
FIG. 1B depicts an example software platform for processing data of high dimensionality.

Data acquired by the data collection component 10 can be transferred to database 20, via network 40 or locally via data transfer cables. In some embodiments, the collected data can be analyzed by data intelligence component 30, via either local or network connection. FIG. 1B depicts exemplary functional modules that can be implemented to perform tasks of data intelligence component 30.

In one aspect, disclosed herein is a system for processing and analyzing data of high dimensionality by performing numerous tasks, including, for example, initial processing of raw sequence read data (e.g., via data normalization, GC content compensation, and etc.), discarding data of high variability, identifying a model representing differences between sequence reads from healthy subjects and sequence reads from cancer subjects, representing data from each subject, and communicating with a remote device (e.g., another computer or a server).

FIG. 1B depicts an exemplary computer system 110 for processing and analyzing data of high dimensionality. Exemplary embodiment 110 achieve the functionalities by implementing, on one or more computer devices, user input and output (I/O) module 120, memory or database 130, data processing module 140, data analysis module 150, classification module 160, network communication module 170, and any other functional modules that may be needed for carrying out a particular task (e.g., an error correction or compensation module, a data compression module, and etc.). As disclosed herein, user I/O module 120 can further include an input sub-module such as a keyboard and an output sub-module such as a display (e.g., a printer, a monitor, or a touchpad). In some embodiments, all functionalities are performed by one computer system. In some embodiments, the functionalities are performed by more than one computers.

Also disclosed herein, a particular task can be performed by implementing one or more functional modules. In particular, each of the enumerated modules itself can, in turn, include multiple sub-modules. For example, data processing module 140 can include a sub-module for data quality evaluation (e.g., for discarding very short sequence reads or sequence reads including obvious errors), a sub-module for normalizing numbers of sequence reads that align to different regions of a reference genome, a sub-module to compensating/correcting GC biases, and etc.

In some embodiments, a user may use I/O module 120 to manipulate data that is available either on a local device or can be obtained via a network connection from a remote service device or another user device. For example, I/O module 120 can allow a user to a keyboard or a touchpad to perform data analysis via a graphical user interface (GUI).

In some embodiments, a user can manipulate data via voice control. In some embodiments, user authentication is required before a user is granted access to the data being requested.

In some embodiments, user I/O module 120 can be used to manage various functional modules. For example, a user can request via user I/O module 120 to request input data while an existing data processing session is in process. A user can do so by selecting a menu option or type in a command discretely without interrupting the existing process.

As disclosed herein, a user can use any type of input to direct and control data processing and analysis via I/O module 120.

In some embodiments, system 110 further comprises a memory or database 130. In some embodiments, database 130 comprises a local database that can be accessed via user I/O module 120. In some embodiments, database 130 comprise a remote database that can be accessed by user I/O module 120 via network connection. In some embodiments, database 130 is a local database that stores data retrieved from another device (e.g., a user device or a server). In some embodiments, memory or database 130 can store data retrieved in real-time from internet searches.

In some embodiments, database 130 can send data to and receives data from one or more of the other functional modules, including but not limited to a data collection module (not shown), data processing module 140, data analysis module 150, classification module 160, network communication module 170, and etc.

In some embodiments, database 130 can be a database local to the other functional modules. In some embodiments, database 130 can be a remote database local that can be accessed by the other functional modules via wired or wireless network connection (e.g., via network communication module 170). In some embodiments, database 130 can include a local portion and a remote portion.

In some embodiments, system 110 comprises a data processing module 140. Data processing module 140 can receive the real-time data, from I/O module 120 or database 130. In some embodiments, data processing module 140 can perform standard data processing algorithms such as noise reduction, signal enhancement, normalization of counts of sequence reads, correction of GC bias, and etc. In some embodiments, data processing module 140 can identify global or local systematic errors. For example, sequencing data can be aligned to regions within a reference genome. The numbers of sequence reads aligned to different genomic regions can vary for the same subject. The numbers of sequence reads aligned to the same genomic regions can vary between subjects. Some of these differences, especially those observed in healthy subjects, can result from systematic errors instead of having association with one or more diseased conditions. For example, if sequencing data corresponding to a particular genomic region shows wide ranges of variation between healthy subjects, data processing module 140 can classify the particular genomic region as a high-noise region and can exclude the corresponding data from further analysis. In some embodiments, instead of exclusion, a weight can be assigned to a supposedly high-noise region to reduce. In some embodiments, the identification and treatment of possible systematic errors can be performed by data analysis module 140, as illustrated below.

In some embodiments, system 10 comprises a data analysis module 150. In some embodiments, data analysis module

150 includes identifying and treating systematic errors in sequencing data, as described in connection with data processing module 140.

In some embodiments, data analysis module 150 can apply one or more machine learning algorithms to data of high dimensionality that are associated with a single subject. This way, data dimensionality is reduced and and information embedded in the data can be simplified before data from a large number of subjects are combined for further analysis such as feature extraction or pattern recognition. In some embodiments, data analysis module 150 can implement one or more machine learning algorithms for both data dimensionality reduction and and pattern recognition at the same time.

In some embodiments, data analysis module 150 includes using reducing the dimensionality of the processed sequencing data. Methods such as Principal Component Analysis (PCA) can be applied to convert the high dimensionality data to low dimensionality data that can still represent the main characteristics of the original sequencing data. For example, about 20,000 counts of sequence reads associated with a subject, which correspond to 20,000 different chromosomal regions of low variability, can be reduced to 1,000 parameters or fewer, 500 parameters or fewer, 200 parameters or fewer, 100 parameters or fewer, 90 parameters or fewer, 80 parameters or fewer, 70 parameters or fewer, 60 parameters or fewer, 50 parameters or fewer, 40 parameters or fewer, 30 parameters or fewer, 20 parameters or fewer, 10 parameters or fewer, 8 parameters or fewer, 5 parameters or fewer, 4 parameters or fewer, 3 parameters or fewer, 2 parameters or fewer, or a single parameter. The low variability training data can be transformed based on the reduction to render a transformed dataset, which can be subject to further analysis to derive relations that illustrating the differences between the healthy subjects and diseased subjects.

In some embodiments, one or more supervised learning algorithms can be used to discover patterns or features within the transformed data set. As disclosed herein, supervised learning problems can be separated into classification and regression problems. As disclosed herein, a classification problem is when the output variable is a category, such as "red" or "blue" or "disease" and "no disease." A regression problem is when the output variable is a real value, such as "dollars" or "weight." Either approach can be adapted to determine whether a subject has a particular disease state. Example learning algorithms include but are not limited to support vector machines (SVM), linear regression, logistic regression, naive Bayes, decision trees algorithm, linear discriminant analysis, discriminant analysis, nearest neighbor analysis (kNN), feature point based approaches, neural networks analysis (multilayer perceptron), principal component analysis (PCA), linear discriminant analysis (LDA), and etc.

In some embodiments, one or more unsupervised learning algorithms can be used to discover patterns or features within the transformed data set. For example, unsupervised learning problems can be further grouped into clustering and association problems. A clustering problem is where you want to discover the inherent groupings in the data, such as grouping customers by purchasing behavior. An association rule learning problem is where you want to discover rules that describe large portions of your data, such as people that buy X also tend to buy Y. Example unsupervised learning algorithms include but are not limited to a clustering algorithm such as hierarchical clustering, k-Means clustering, Gaussian mixture models, self-organizing maps and Hidden Markov models, an algorithm for anomaly detection, a neural network based algorithm such as autoencoders, deep beliefs nets, Hebbian learning, generative adversarial networks, an algorithm for learning latent variable models such as expectation-maximization algorithm (EM), method of moments, blind signal separation techniques (e.g., principal component analysis (PCA), independent component analysis, non-negative matrix factorization, singular value decomposition, and etc.

In some embodiments, a semi-supervised machine learning algorithm can be used; for example, using any combinations of the algorithms enumerated herein or known in the art.

In some embodiments, data analysis module 150 derives, for each subject, one or more parameters based on training data, either with or without data dimensionality reduction. In some embodiments, one or more parameters are used to classify test subjects. For example, the training data can be used to calculate a binomial or multinomial probability score.

In some embodiments, system 10 comprises a classification module 160, which analyze data from a test subject whose status with respect to a medical condition is unknown and subsequently classify the unknown test subject based on the likelihood of the subject fitting into a particular category. In some embodiments, the one or more parameters include a binomial probability score that is calculated based on logistic regression analysis. As disclosed herein, the binomial probability score can correspond to the likelihood of a subject having a certain medical condition such as cancer. For example, a score of over a predefined threshold can indicate that the subject is more likely to have cancer than not having cancer. In some embodiments, the one or more parameters can include a sequencing data distribution pattern correlating with the presence of cancer. A subject with a pattern resembling the cancer pattern may be diagnosed as having cancer. In some embodiments, a sequencing data distribution pattern may be identified in connection with a specific type of cancer, thus allowing an unknown subject to be classified with further details.

As disclosed herein, network communication module 170 can be used to facilitate communications between a user device, one or more database, and any other system or device through a wired or wireless network connection. Any communication protocol/device can be used, including without limitation a modem, an Ethernet connection, a network card (wireless or wired), an infrared communication device, a wireless communication device, and/or a chipset (such as a Bluetooth™ device, an 802.11 device, a WiFi device, a WiMax device, cellular communication facilities, etc.), a near-field communication (NFC), a Zigbee communication, a radio frequency (RF) or radio-frequency identification (RFID) communication, a PLC protocol, a 3G/4G/5G/LTE based communication, and/or the like. For example, a user device having a user interface platform for processing/analyzing data of high dimensionality can communicate with another user device with the same platform, a regular user device without the same platform (e.g., a regular smartphone), a remote server, a physical device of a remote IoT local network, a wearable device, a user device communicably connected to a remote server, and etc.

The functional modules described herein are provided by way of example. It will be understood that different functional modules can be combined to create different utilities. It will also be understood that additional functional modules or sub-modules can be created to implement a certain utility.

FIG. 2A depicts an example process, depicting the overall method flow 200 for processing data of high dimensionality.

In FIG. 2A, a few key actions are highlighted, including but not limited to defining a low variability filter that can be used to identify high-quality data (e.g., step 204), establishing a difference or prediction model based on filtered data of training samples (e.g., step 206), computing classification scores based on filtered data of test samples and predicting the likelihood for a test sample to have a certain medical condition (e.g., step 208). An optional step 202 is also possible where data can be processed to improve quality. Sequencing data of cell-free nucleic acids are used to illustrate the concepts. However, one of skill in the art would understand that the current method can be applied to sequencing data of other materials or non-sequencing data as well.

At step 202, optional data processing can be performed to improve data quality. As disclosed herein, data processing can include data adjustment or calibration; for example, based on data obtained from a control group of healthy subjects. For example, biological data (e.g., sequencing data) can be pre-processed to correct biases or errors using one or more methods such as normalization, correction of GC biases, correction of biases due to PCR over-amplification, and etc.

At step 204, one or more criteria are formulated to improve the quality of data of high dimensionality by identifying and eliminating systematic errors or other types of non-disease related noises during data collection. Although data of high dimensionality can be broadly construed to cover non-biological data, the current disclosure focuses on high dimensional biological data such as sequencing data. Examples of the sequencing data include but are not limited to whole genome sequencing data, targeted sequencing data, epigenetic analytical data, and etc. As disclosed herein, sequencing can include but are not limited to nucleic acid sequencing (e.g., DNA, RNA, or hybrids or mixtures thereof), protein sequencing, sequence-based epigenetic analysis for analyzing protein-nucleic acid interactions (e.g., DNA or RNA methylation analysis, histone modification analysis, or combinations thereof), or protein-protein sequence modification analysis such as acetylation, methylation, ubiquitylation, phosphorylation, sumoylation, or combinations thereof.

In some embodiment, biological data (e.g., sequencing data) subject to the analysis at step 204 have been pre-processed to correct biases or errors using one or more methods such as normalization, correction of GC biases, correction of biases due to PCR over-amplification, and etc.

In some embodiments, one or more criteria are established to exclude nucleic acid sequencing data that likely contain systematic errors or other types of non-disease related noises during data collection. As disclosed herein, sequence data can include sequence reads of any biological samples, including but not limited to cell-free nucleic acid samples.

In some embodiments, data from only healthy subjects are used to establish the one or more criteria to avoid interferences from data associated with one or more disease conditions. In some embodiments, a criterion as disclosed herein can be established with respect to genomic or chromosomal regions. For example, nucleic acid sequence reads can be aligned to regions of a reference genome and one or more characteristics of the sequence reads can be used to determine whether data associated with a particular genomic region include more noises than useful information and thus should be excluded from subsequent analyses. Exemplary characteristics include but are not limited to, for example, number of reads, mappability of the reads, and etc.

In some embodiments, the genomic regions have the same size. In some embodiments, the genomic regions can have different sizes. In some embodiments, a genomic region can be defined by the number of nucleic acid residues within the region. In some embodiments, a genomic region can be defined by its location and the number of nucleic acids residues within the region. Any suitable size can be used to define genomic regions. For example, a genomic region can include 10 kb or fewer, 20 kb or fewer, 30 kb or fewer, 40 kb or fewer, 50 kb or fewer, 60 kb or fewer, 70 kb or fewer, 80 kb or fewer, 90 kb or fewer, 100 kb or fewer, 110 kb or fewer, 120 kb or fewer, 130 kb or fewer, 140 kb or fewer, 150 kb or fewer, 160 kb or fewer, 170 kb or fewer, 180 kb or fewer, 190 kb or fewer, 200 kb or fewer, or 250 kb or fewer.

Setting a chromosomal region to a large size allows one to scan through a target (e.g., the entire human genome) and perform analysis quickly. Setting a chromosomal region to a small size, on the other hand, allows one to more precisely pinpoint locations on a reference genome that are more likely to be the sources of systematic errors or noises. However, such a detailed analysis will be more time-consuming.

In some embodiments, a rough scan of the genome can be performed using large chromosomal regions. In some embodiments, a more refined scan can be performed over a smaller chromosomal region following a rough scan.

Step 204 is essentially a data selection step. When step 204 is completed, regions that are possibly associated with systematic errors are identified. In some embodiments, one or more criteria can be defined to reduce or eliminate data corresponding to these noisier regions. For example, a high variability filter can be created to allow one to discard data corresponding to all regions with data variations above a threshold value. In other embodiments, a low variability filter can be created to focus subsequent analysis on data with data variations below a threshold.

As an illustration, a human haploid reference genome includes over three billion bases that can be divided into about 30,000 regions (or bins). If an experimental value is observed for each bin, for example, a total number of sequence reads that align to the particular region or bin, each subject can correspond to over 30,000 measurements. After a low or high variability filter is applied, the number of measurements corresponding to a subject can be reduced by a significant portion; for example, including but not limited to about 50% or less, about 45% or less, about 40% or less, about 35% or less, about 30% or less, about 25% or less, 20% or less, 15% or less, 10% or less, or 5% or less. In some embodiments, the number of measurements corresponding to a subject can be reduced by 50% or more such as about 55%, 60%, 65%, or 70% or more. For example, a subject, which originally has over 30,000 corresponding measurements, can have over 30% fewer measurements (e.g., about 20,000) after a high or low variability filter is applied.

At step 206, the one or more criteria established from the previous step can be applied to a biological dataset of a training group (also referred to as "training data"). As disclosed herein, the training group includes both healthy subjects and subjects known to have one or more medical conditions (also referred to as "diseased subjects"). For example, for sequencing data, the one or more criteria previously determined in step 204 (e.g., a low or high variability filter) is applied to data of the training group to completely remove the portion of the data that are associated with the chromosomal regions defined in the filter. In some embodiments, the presumably noisy data are only partially removed. In some embodiments, the presumably noisy data that are not removed can be assigned a weighting factor to reduce their significance in the overall dataset.

Once data selection is performed for the biological dataset for the training group, the remaining training data, also referred to as the "selected training data" or "filtered training data," are subject to further analysis to extract features that reflect differences between healthy subjects and subjects known to have one or more medical conditions. As noted previously, the original training data include data from both healthy subjects and diseased subjects. The filtered training data constitute a part of the original training data and thus also include data from both healthy subjects and subjects known to have a medical condition. It is assumed that the largest variations among the filtered training data come from differences between data from the healthy subjects and data from the diseased subjects. In essence, it is assumed that data associated with a heathy subject should be more similar to data of another healthy subject than the data from any diseased subject; and vice versa.

Like the original training data, the filtered training data are also of high dimensionality. In some embodiments, the filtered training data are subject to further analysis to reduce data dimensionality and differences between the healthy and diseased subjects are defined based on the reduced dimensionalities. For a given subject, about 20,000 filtered measurements can be further reduced to a handful of data points. For example, the about 20,000 filtered measurements can be transformed based on a few extracted features (e.g., a number of principal components) to render a number of data points. In some embodiments, after reduction of dimensionality, there are 5 or fewer features; 6 or fewer features; 7 or fewer features; 8 or fewer features; 9 or fewer features; 10 or fewer features; 12 or fewer features; 15 or fewer features; or 20 or fewer features. In some embodiments, the filtered measurements can have more than 20 features. The filtered measurements can then be transformed based on the selected features. For example, a sample having two 20,000 filtered measurements can be transformed and reduced to five or fewer data points. In some embodiments, a sample having two 20,000 filtered measurements can be transformed and reduced to more than five data points, such as 10, 15, 20, and etc.

As disclosed herein, the transformed data points from all subjects in the filtered training dataset are subject to further analysis to extract relations or patterns that reflect the differences between the sub-groups in the filtered training dataset. In some embodiments, further analysis includes a binomial logistic regression process; for example, for determining the likelihood of a subject having cancer versus not having cancer. In some embodiments, further analysis includes a multinomial logistic regression process; for example, for determining the type of cancer in addition to the likelihood of a subject having cancer.

At step 208, a classification score is computed for each subject. In some embodiments, the classification score is a probability score representing the likelihood of a subject being classified as having a particular condition; for example, being normal versus having cancer, or having liver cancer versus having lung cancer.

Figure 2B:
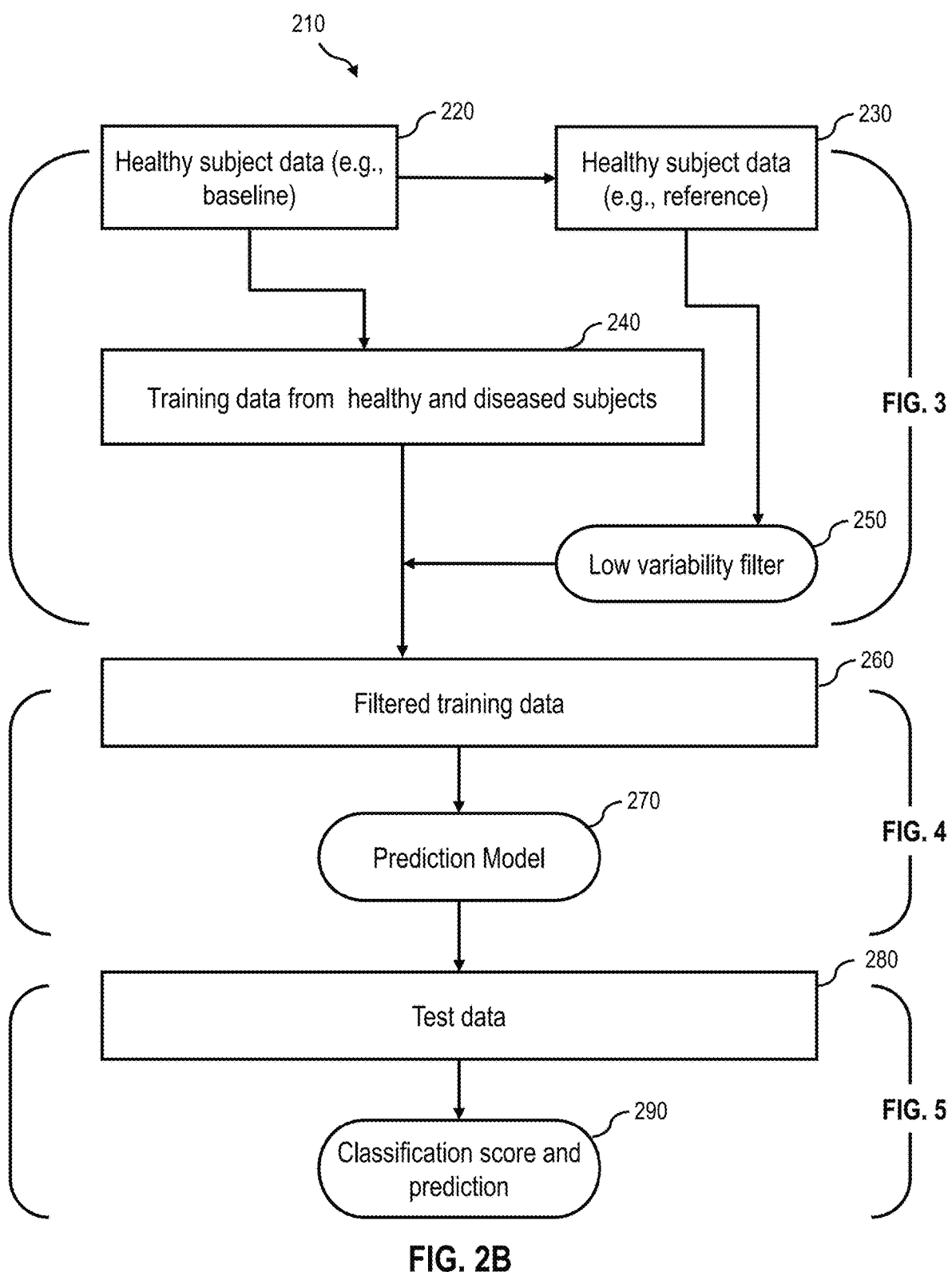
FIG. 2B depicts an example embodiment, illustrating information flow when processing data of high dimensionality.

FIG. 2B depicts an example embodiment, illustrating information flow when processing data of high dimensionality. Example embodiment 210 covers data selection (e.g., elements 220 through 250), processing and analysis of training data (e.g., elements 260 and 270), and classification of test data (e.g., elements 280 and 290). Sequencing data of cell-free nucleic acids are used to illustrate the concepts.

However, one of skill in the art would understand that the current method can be applied to sequencing data of other materials or non-sequencing data as well.

During the data selection portion, data of high dimensionality (e.g., element 220 such as sequencing reads) are initially processed to improve quality. In some embodiments, the number of sequence reads that align to a particular region of a reference genome is normalized. For example, data 220 can include sequence reads from a group of healthy subjects (also referred to as baseline subjects) and data from the baseline subjects can be used to establish the normalization standards. In some embodiments, sequence reads from the baseline subjects are aligned to a reference genome that is already divided into a plurality of regions. Assuming that there are no significant biases during the sequencing process, different regions in the genomes should be covered at roughly the same level. Consequently, the number of sequence reads that align to a particular region should be the same as those sequence reads that align to another region of the same size.

In one example, the number of sequence reads from a baseline subject across different genomic regions can be written as $$\mathrm{Read}_i^j,$$

where integer i denotes a subject and is 1 through n while integer j denotes a genomic region and has a value of 1 through m. As disclosed, a reference genome can be divided into any number of genomic regions, or genomic regions of any sizes. A reference genome can be divided into up to 1,000 regions, 2,000 regions, 4,000 regions, 6,000 regions, 8,000 regions, 10,000 regions, 12,000 regions, 14,000 regions, 16,000 regions, 18,000 regions, 20,000 regions, 22,000 regions, 24,000 regions, 26,000 regions, 28,000 regions, 30,000 regions, 32,000 regions, 34,000 regions, 36,000 regions, 38,000 regions, 40,000 regions, 42,000 regions, 44,000 regions, 46,000 regions, 48,000 regions, 50,000 regions, 55,000 regions, 60,000 regions, 65,000 regions, 70,000 regions, 80,000 regions, 90,000 regions, or up to 100,000 regions. As such, m can be an integer corresponding to the number of genomic regions. In some embodiments, m can be an integer larger than 100,000.

In some embodiments, sequence reads of a subject can be normalized to the average read count across all chromosomal regions for the subject. When i remains constant, sequence reads from genomic regions 1 through m and the corresponding sizes of the regions can be used to compute an average expected number of sequence reads for subject i, for example, based on the equation:

$$\overline{\mathrm{Read}_i} = \sum\nolimits_{j=1}^{j=m}(\mathrm{Read}_i^j/SizeRegion_i^j)/m, \qquad (1)$$

where $$SizeRegion_i^j$$

represents the size of the particular chromosomal region (e.g., in bases or kilobases) to which the sequence reads $$(Read_i^j)$$

are aligned. Here, $$Read_i^j / SizeRegion_i^j$$

is a sequence read density value. As such, for a subject i, the expected number of sequence reads that would align to a given chromosomal region j having a size of $$SizeRegion_i^j$$

can be calculated using the following:

$$\overline{Read_i} \times SizeRegion_i^j. \qquad (2)$$

As disclosed herein, data for any subject across different genomic regions can be used as a control to normalize the sequence reads of a genomic region. Here, an average read, which is used as the basis for data normalization, can be computed for a healthy control subject, a group of control subjects, or a test subject itself.

In some embodiments, sequence reads of a subject can be normalized against an overall average count from a group of subjects (e.g., a group of n healthy subjects). Additional details can be found in the description in connection with FIG. 3.

In some embodiments, sequence reads for a subject corresponding to a particular region can be normalized using multiple approaches, utilizing both data from different regions for the subject itself and cross different control subjects.

In one aspect, disclosed herein are methods for establishing a template for selecting data for further analysis, based on patterns gleaned from data from healthy subjects (e.g., baseline healthy subjects 220 and reference healthy subjects 230). In preferred embodiments, reference healthy subjects 230 do not or only have minimum overlap with baseline healthy subjects 220. Sequencing data of cell-free nucleic acids are used to illustrate the concepts. However, one of skill in the art would understand that the current method can be applied to sequencing data of other materials or non-sequencing data as well.

In some embodiments, the number of healthy subjects in a baseline or reference healthy subject group can be varied. In some embodiments, the selection criteria for healthy subjects in the baseline and reference healthy subject groups are the same. In some embodiments, the selection criteria for healthy subjects in the baseline and reference healthy subject groups are different.

In some embodiments, a high or low variability filter is established using data from healthy reference subjects (e.g., element 230). As disclosed herein, the data from healthy reference subjects 230 can be pre-processed (e.g., undergoing various normalization steps); for example, based on baseline control data from healthy subjects (e.g., element 220). For example, training data from both healthy and cancer subjects can be pre-processed. In some embodiments, raw sequence read data can be directly used to set up a high or low variability filter.

In some embodiments, sequence reads of each healthy subject (e.g., from healthy subject data 230) can be aligned to a plurality of chromosomal regions of reference genome. The variability of reach genomic region can be evaluated; for example, by comparing numbers of sequence reads for a particular genomic region across all healthy subjects in the control group. As an illustration, healthy subjects who are not expected to have cancers can be included as reference controls. The healthy subjects include but are not limited to subjects who do not have family histories of cancer or who are healthy and young (e.g. under 35 or 30-year-old). In some embodiments, healthy subjects in the reference control group may satisfy other conditions; for example, only healthy women will be included in a control group for breast cancer analysis. Only men will be included in a control group for prostate cancer analysis. In some embodiments, for diseases that are found predominantly or only in a particular ethnic group, only people from the same ethnic group are used to establish the reference control group.

For example, for a group of control healthy subjects (n), if we count the number of sequence reads that align to a genomic region, there will be n values for each genomic region. Parameters, such as a mean or medium count, standard deviation (SD), median absolute deviation (MAD), or the interquartile range (IQR), can be computed based on the n count values and used to determine whether a genomic region is considered of low or high variability. Any method for computing these parameters can be used.

For example, the sequence read numbers for region j in subjects 1 through n can be represented as $$Read_i^j,$$

where j is an integer and i is an integer between 1 and n. An average read count of region j $\overline{Read^j}$ can be calculated using $$\overline{Read^j} = \left( \sum_{i=1}^{i=n} Read_i^j / n \right).$$

In some embodiments, IQR can be computed and compared with $\overline{Read^j}$. If the difference between IQR and $\overline{Read^j}$ is above a pre-determined threshold, data from region j may be considered of high variability and will be discarded before subsequent analysis. By repeating the process for all regions in a reference genome, a genome-wide high or low variability filter (e.g., element 250) can be established. For example, for any sequencing data associated with a subject (who is preferably not in the reference control group), sequence reads that align to regions corresponding to the high variability filter will be discarded. A low variability filter would include regions whose difference between IQR and $\overline{Read^j}$ that are below a pre-determined threshold.

In some embodiments, high or low variability filters can be created for only a portion of the genome; for example, for only a particular chromosome or a portion thereof.

In some embodiments, training data 240 includes biological data (e.g., sequencing data) from both healthy subjects and subjects known to have a medical condition (also known as diseased subjects). In some embodiments, data associated healthy subjects who have previously been included in the baseline control group or reference control group will be excluded from training data 240 to possibly avoid certain biases.

In some embodiments, normalization parameters obtained using healthy subject data 220 and the low or high variability filter 250 can be applied to training data 240 to render new and filtered training data 260 for subsequent analysis.

In some embodiments, filtered training data 260 comprise balanced data for healthy and diseased subjects; for example, the numbers of healthy and diseased subjects are within about 5 to 10% of each other. In some embodiments, filtered training data 260 comprise unbalanced data for healthy and diseased subjects; for example, the numbers of healthy and diseased subjects differ more than 10% from each other. In the latter situation, methods can be applied to reduce the impact of unbalanced data.

In some embodiments, filtered training data 260 are subject to further analysis to create prediction model 270. Prediction model 270 is used to predict whether a subject has a certain medical condition.

In some embodiments, prediction model 270 reflects differences between healthy and diseased subjects. In some embodiments, the differences used in prediction model 270 can be obtained by applying, for example, logistic regression to filtered training data 260. In some embodiments, filtered training data 260 (e.g., numbers of sequence read that align to certain regions of a reference genome) can be directly used in logistic regression analysis. In some embodiments, filtered training data 260 undergoes a dimensionality reduction to reduce and possibly transform the dataset to a much smaller size. For example, Principal Component Analysis (PCA) can be used to reduce the size of a data set by about 100,000-fold or less, about 90,000-fold or less, about 80,000-fold or less, about 70,000-fold or less, about 60,000-fold or less, about 50,000-fold or less, about 40,000-fold or less, about 30,000-fold or less, about 20,000-fold or less, about 10,000-fold or less, about 9,000-fold or less, about 8,000-fold or less, about 7,000-fold or less, about 6,000-fold or less, about 5,000-fold or less, about 4,000-fold or less, about 3,000-fold or less, about 2,000-fold or less, about 1,000-fold or less, or about 500 fold or less. In some embodiments, the size of a data set can be reduced by more than 100,000-fold. In some embodiments, the size of a data set can be reduced by a couple of hundred folds or less. As disclosed herein, although the size of a data set is reduced, the number of samples can be retained. For example, after PCA, a data set of 1,000 samples can still retain 1,000 samples but the complexity of each sample is reduced (e.g., from corresponding to 25,000 features to 5 or fewer features). As such, the methods disclosed herein can improve efficiency and accuracy of data processing while greatly reduce computer storage space required.

Once a prediction model is established, it can be applied to test data 280. Test data 280 can be taken from a test subject whose status is unknown with respect to a medical condition. In some embodiments, data from test subjects of known statuses can also be used for validation purposes. Though not depicted in FIG. 2B, test data will be processed; for example, using the scheme depicted in elements 220 through 250. In some embodiments, test data 280 will be pre-processed such as going through normalization, GC content correction, and etc. In some embodiments, a high or low variability filter 250 is applied to test data 280 to remove data in chromosomal regions that likely correspond to systematic errors. In some embodiments, both pre-processing and a high or low filter can be applied to test data 280 to render filtered test data for further processing.

In some embodiments, when prediction model 260 is applied to filtered test data, a classification score can be computed as a probability score to represent the likelihood for the particular medical condition to be present in the test subject being analyzed. In some embodiments, the probability score can be a binomial classification score; for example, non-cancer versus cancer. In some embodiments, the probability score can be a multinomial classification score; for example, non-cancer, liver cancer, lung cancer, breast cancer, prostate cancer, and etc.

The methods and systems disclosed herein can be applied to provide diagnosis or prognosis of any suitable medical conditions linked to any germline or somatic mutations. In particular, the medical conditions include but are not limited to any cancer or tumor defined by the National Institutes of Cancer, including but not limited to acute lymphoblastic leukemia (ALL), acute myeloid leukemia (AML), cancer adolescents, adrenocortical carcinoma, childhood adreno-cortical carcinoma, AIDS-related cancer, kaposi sarcoma, AIDS-related lymphoma (lymphoma), anal cancer, appendix cancer—see gastrointestinal carcinoid tumors, astrocytomas, childhood (brain cancer), atypical teratoid/rhabdoid tumor, childhood, central nervous system (brain cancer), basal cell carcinoma of the skin, bile duct cancer, bladder cancer, childhood bladder cancer, bone cancer (e.g., ewing sarcoma and osteosarcoma and malignant fibrous histiocytoma), brain tumors, breast cancer, childhood breast cancer, childhood bronchial tumors, burkitt lymphoma, carcinoid tumor (gastrointestinal), childhood carcinoid tumors, carcinoma of unknown primary, childhood carcinoma of unknown primary, childhood cardiac (heart) tumors, central nervous system (e.g., brain cancer such as childhood atypical teratoid/rhabdoid tumor, childhood embryonal tumors, childhood germ cell tumor, cervical cancer, childhood cervical cancer, and etc.), cholangiocarcinoma, childhood chordoma, chronic lymphocytic leukemia (CLL), chronic myelogenous leukemia (CML), chronic myeloproliferative neoplasms, colorectal cancer, childhood colorectal cancer, childhood craniopharyngioma, cutaneous t-cell lymphoma (e.g., mycosis fungoides and Sézary syndrome), ductal carcinoma In Situ (DCIS), childhood embryonal tumors, endometrial cancer (uterine cancer), childhood ependymoma, esophageal cancer, childhood esophageal cancer, esthesioneuroblastoma (head and neck cancer), childhood extracranial germ cell tumor, extragonadal germ cell tumor, eye cancer, which includes childhood intraocular melanoma, intraocular melanoma, retinoblastoma, and etc., fallopian tube cancer, gallbladder cancer, gastric (stomach) cancer, childhood gastric (stomach) cancer, gastrointestinal carcinoid tumor, gastrointestinal stromal tumors (GIST), childhood gastrointestinal stromal tumors, germ cell tumors (e.g., childhood central nervous system germ cell tumors, childhood extracranial germ cell tumors, extragonadal germ cell tumors, ovarian germ cell tumors, or testicular cancer), gestational trophoblastic disease, hairy cell leukemia, head and neck cancer, childhood heart tumors, hepatocellular cancer (HCC), langerhans cell histiocytosis, hodgkin lymphoma, intraocular melanoma, childhood intraocular melanoma, islet cell tumors (pancreatic neuroendocrine tumors), kidney or renal cell cancer (RCC), langerhans cell histiocytosis, laryngeal cancer, leukemia, liver cancer, lung cancer (non-small cell and small cell), childhood lung cancer, lymphoma, male breast cancer, malignant fibrous histiocytoma of bone and osteosarcoma, melanoma, childhood melanoma, intraocular melanoma, childhood intraocular melanoma, merkel cell carcinoma, malignant mesothelioma, childhood mesothelioma, metastatic cancer, metastatic squamous neck cancer with occult primary, midline tract carcinoma with NUT gene changes, mouth cancer (head and neck cancer), multiple endocrine neoplasia syndromes, multiple myeloma/plasma cell neoplasms, mycosis fungoides (lymphoma), myelodysplastic syndromes, myelodysplastic/myeloproliferative neoplasms, chronic myeloproliferative neoplasms, nasal cavity and paranasal sinus cancer, nasopharyngeal cancer (NPC), neuroblastoma, Non-Hodgkin lymphoma, non-small cell lung cancer, oral cancer, lip and oral cavity cancer and oropharyngeal cancer, osteosarcoma and malignant fibrous histiocytoma of bone, ovarian cancer, childhood ovarian cancer, pancreatic cancer, childhood pancreatic cancer, papillomatosis (childhood laryngeal), paraganglioma, childhood paraganglioma, paranasal sinus and nasal cavity cancer, parathyroid cancer, penile cancer, pharyngeal cancer, pheochromocytoma, childhood pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, recurrent cancer, retinoblastoma, childhood rhabdomyosarcoma, salivary gland cancer, sarcoma (e.g., childhood vascular tumors, osteosarcoma, and uterine sarcoma), Sézary syndrome (lymphoma), skin cancer, childhood skin cancer, small cell lung cancer, small intestine cancer, squamous cell carcinoma of the skin, squamous neck cancer with occult primary, metastatic (head and neck cancer), stomach (gastric) cancer, childhood stomach (gastric) cancer, cutaneous t-cell lymphoma, testicular cancer, childhood testicular cancer, throat cancer (e.g., nasopharyngeal cancer, oropharyngeal cancer, hypopharyngeal cancer), thymoma and thymic carcinoma, thyroid cancer, transitional cell cancer of the renal pelvis and ureter, unknown primary carcinoma, unusual cancers of childhood, ureter and renal pelvis, transitional cell cancer (kidney (renal cell) cancer, urethral cancer, endometrial uterine cancer, uterine sarcoma, vaginal cancer, childhood vaginal cancer, vascular tumors, vulvar cancer, Wilms tumor and other childhood kidney tumors, cancer in young adults, and etc.

In some embodiments, the methods disclosed herein can be applied to detect genetic variations relating to non-cancerous conditions, including but not limited to, for example, Alzheimer disease, Androgen insensitivity, Campomelic dysplasia, Chronic infantile neurologic cutaneous articular (CINCA), Cleidocranial dysplasia, CHARGE syndrome, Congenital central hypoventilation, Costello syndrome, Duchenne muscular dystrophy, EEC (ectrodactyly, ectodermal dysplasia, and orofacial clefts), Epidermolysis bullosa simplex, Fascioscapular humeral muscular dystrophy, Hemphilia A, Hemophilia B, Hereditary spastic paraplegia, Hunter's syndrome, Hypocalcemia, Infantile spinal muscular atrophy, Lesch-Nyhan, Loeys-Dietz, Marfans, MYH9 disorders, Myoclonic epilepsy, Neonatal diabetes, Ornithine transcarbamylase deficiency, Osteogenesis imperfecta, Otopalato digital syndrome, Phenylketonuria, Progeria, Retinitis pigmentosa RPGR or RP2, Retinoblastoma, Rett syndrome, Rubinstein-Taybi, Thanatophoric dysplasia, Von Hippel-Lindou, X-linked dyskeratosis congenital, X-linked hypophosphatemia, X-linked mental retardation (ARX or SLC6A8), Trisomy 1q, Monosomy 7, Ring 7, Ring 8, Tetrasomy 9p, Ring 17, Isodicentric Y, XXY, neurofibromatosis, McCune-Albright syndrome, incontinentia pigmenti, Paroxysmal nocturnal hemoglobinuria, Proteus syndrome, proteus (Klippel-Trenaunay and Maffuci), Duchenne Muscular Dystrophy, and etc. Additional information can be found in for example, Erickson R., 2003, *Mutat Res.,* 543(2): Pages 87-180; Erickson R, 2010, *Mutat Res.;*705 (2):96-106; each of which is hereby incorporated by reference in its entirety.

In one aspect, disclosed herein are efficient methods for selecting data for subsequent analysis from data of high dimensionality. FIG. 3A depicts a sample process for data selection. In essence, process 300 illustrates exemplary steps for facilitating data conversion and processing between elements 210, 220, 230 and 240. In particular, data from two groups of healthy subjects (e.g., step 302) are used to derive general processing criteria (e.g., step 304) and a set of systematic data filter criteria (e.g., step 306) before both sets of criteria are applied to training data to create processed and filtered training data for subsequent analysis (e.g., step 308).

At step 302, biological data such as sequencing data are obtained from two groups of healthy subjects: baseline healthy subjects and reference healthy subjects. In some embodiments, the baseline healthy subjects are used to adjust or calibrate the data. For example, in the case of sequencing data, baseline healthy subjects are used to improve overall data quality in a macroscopic sense. In some embodiments, the reference healthy subjects are used to define systematic errors and allowing an systematic exclusion of data likely corresponding to such errors.

At step 304, data from the reference healthy subjects are pre-processed to improve data quality. For example, the data can be normalized or corrected for GC biases, using parameters established by analyzing the data from the baseline healthy subjects. In some embodiments, data from each reference healthy subject can be pre-processed based on parameters set up using data from all reference healthy subjects.

At step 306, the processed data from reference healthy subjects are then subject to further analysis to define a high or low variability filter. As disclosed herein, the processed data will be sub-divided into non-overlapping groups. For example, sequencing data can be divided into groups based on how the sequence data align to regions in a reference genome. A variability filter defines the likely "noisy" genomic regions in a reference genome; i.e., the regions that tend to be associated with systematic errors. As noted above, the systematic errors are identified using reference healthy subjects. For example, a high variability filter specifies that any region with errors above a set threshold will be excluded from further analysis. A low variability filter, on the other hand, specifies that any region with errors below a set threshold will be selected for further analysis.

At step 308, the high or low variability filter from step 306 will be applied to data associated with a training group. As disclosed herein, training data include data from both healthy subjects and subjects who are known to have a medical condition (also referred to as "diseased subjects"). Training data will be divided into non-overlapping groups; e.g., the same as those defined in connection with the data from reference healthy subjects. For example, for sequence data, data corresponding to those are associated with the "noisy" genomic regions (e.g., specified in a high variability filter) will be discarded. The resulting filtered data will be subject to further analysis.

Figure 3B:
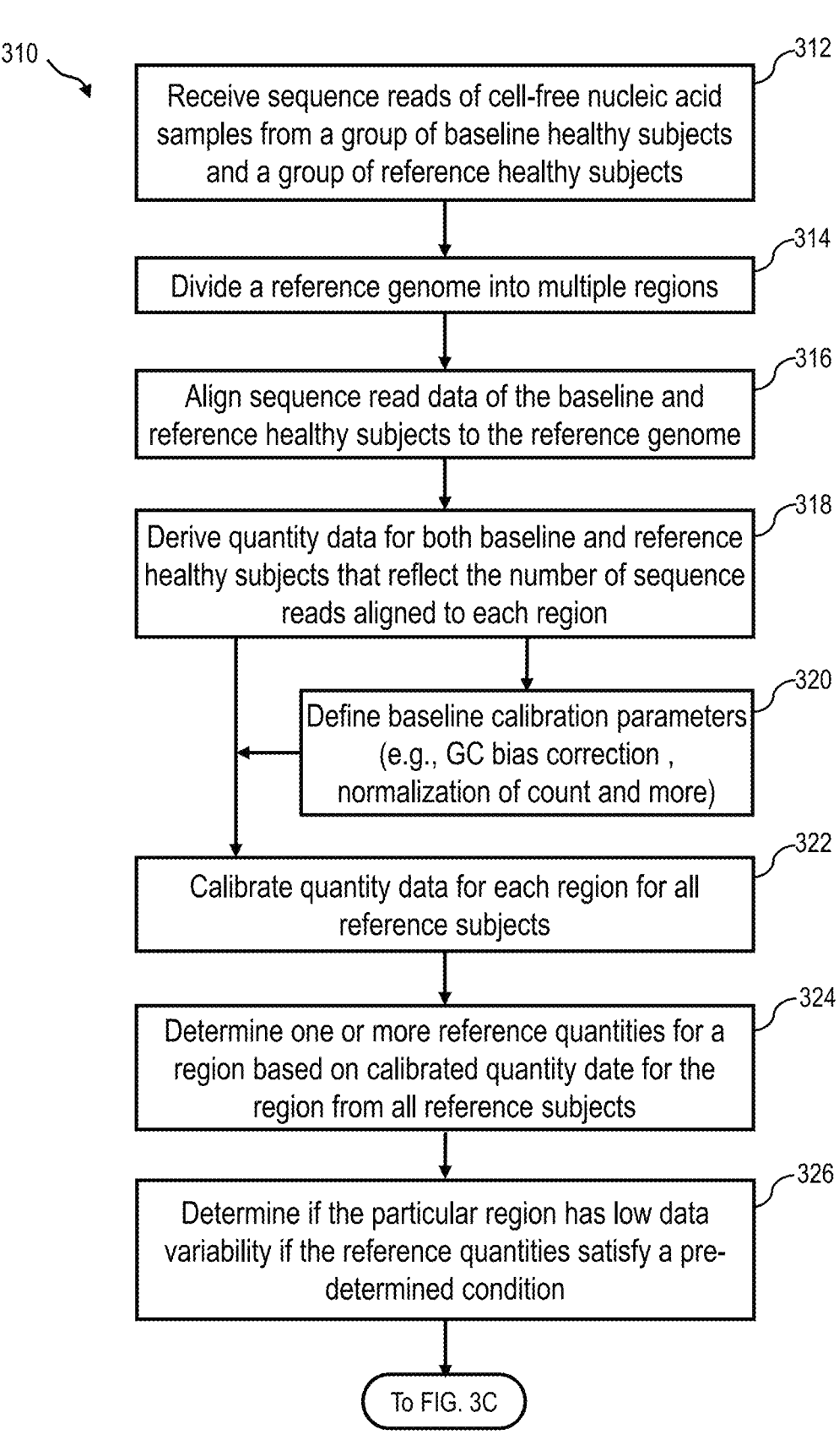
FIG. 3B depicts a sample process for data selection.

FIGS. 3B and 3C depict a sample process for data selection. Again, sequencing data from cell-free nucleic acid samples are used to illustrate sample process 310 and provide more details in comparison to the general steps outlined in sample process 300 (FIG. 3A). However, one of skill in the art would understand that the current method can be applied to sequencing data of other materials or non-sequencing data as well.

At step 312, sequence reads of cell-free nucleic acid samples from baseline healthy subjects and from reference healthy subjects are received. As disclosed herein, the healthy subjects are subjects who have not been diagnosed with a medical condition that is being analyzed. As disclosed herein, the healthy subjects are subjects who have no immediate family members who have been diagnosed with the medical condition that is being analyzed. As disclosed herein, the healthy subjects are subjects who have not been diagnosed with a medical condition that is being analyzed and are under a pre-determined age limit; for example, under about 40 years old, under about 35 years old, or under about 30 years old. In some embodiments, the healthy subjects are above a pre-determined age limit, such as about 15 years or older, about 18 years or older, or about 21 years or older. In preferred embodiments, subjects in the baseline healthy group and reference healthy group do not overlap. In some embodiments, one or more healthy subjects may be used included in both groups. In some embodiments, the criteria for defining healthy subjects are the same for both groups. In some embodiments, the criteria for defining healthy subjects are different for the two groups.

At step 314, a reference genome is divided into multiple genomic regions. Here, the reference genome includes all sequence information of a subject that is representative of the organism. As disclosed herein, the reference subject, healthy subjects, and subjects in the training group are all of the same organism. In some embodiments, the multiple regions are of the same size. In some embodiments, the multiple regions can have different sizes. In some embodiments, a genomic region can be defined by the number of nucleic acid residues within the region. In some embodiments, a reference genome can be divided multiple times. For example, a wider or bigger genomic region allows the entire genome to be scanned or analyzed quickly. In some embodiments, if a region is of interest but seems to correspond to high systematic errors (hence should be discarded from further analysis), the region (and sometimes adjustment regions) can be re-grouped and re-divided into smaller genomic regions. This way, the presumed systematic errors can be more precisely characterized; for example, a portion of the original region may have low variability and can be preserved for further analysis.

Any suitable size can be used to define genomic regions. For example, a genomic region can include 10,000 bases or fewer, 20,000 bases or fewer, 30,000 bases or fewer, 40,000 bases or fewer, 50,000 bases or fewer, 60,000 bases or fewer, 70,000 bases or fewer, 80,000 bases or fewer, 90,000 bases or fewer, 100,000 bases or fewer, 110,000 bases or fewer, 120,000 bases or fewer, 130,000 bases or fewer, 140,000 bases or fewer, 150,000 bases or fewer, 160,000 bases or fewer, 170,000 bases or fewer, 180,000 bases or fewer, 190,000 bases or fewer, 200,000 bases or fewer, 220,000 bases or fewer, 250,000 bases or fewer, 270,000 bases or fewer, 300,000 bases or fewer, 350,000 bases or fewer, 400,000 bases or fewer, 500,000 bases or fewer, 600,000 bases or fewer, 700,000 bases or fewer, 800,000 bases or fewer, 900,000 bases or fewer, or 1,000,000 bases or fewer. In some embodiments, a genomic region can include more than 1,000,000 bases.

At step 316, sequencing data (e.g., sequence reads) from the baseline healthy subjects and reference healthy subjects are aligned to the reference genome.

At step 318, a pre-designated genomic region can be characterized by its location on the reference genome and a quantity reflecting, the number of the sequence reads that align to the region. In some embodiments, the characteristic can be a quantity. For example, the characteristic can be a count number of sequence reads that are associated with a particular region on a reference genome. For example, sequencing data corresponding to the particular region can be reduced to a single quantity such as the total number of sequence reads that aligned to the region or a sequence read density value (e.g., the total number of sequence reads divided by the size of the region). In some embodiments, count numbers can be further broken down by the fragment size to which the sequence reads correspond. Instead of a single quantity representing the total number of sequence reads aligned to a particular region, sequencing data data associated the particular region can be represented by multiple quantities each corresponding to a length or length range of target fragments. For example, sequence reads corresponding to target fragments of 150 to 155 bases will be characterized as one count number while sequence reads corresponding to target fragments of 155 to 160 bases will be characterized as another count number. In some embodiments, an amount reflecting a characteristic of a particular genomic region can be used. For example, the number of sequence reads that indicate a level of methylation for the particular region can be used. In some embodiments, among all the sequence reads that align to a particular genomic region, only those sequence reads that reveal one or more methylation sites are counted to represent the particular genomic region. In some embodiments, the total number of methylation sites revealed by the sequence reads will be used to represent the particular genomic region. In some embodiments, a methylati on density value (e.g., total number of methylation sites divided by size of the particular genomic region) can be used. In some embodiments, it is possible to formulate a parameter that can represent one or more characteristics associated with a particular genomic region.

At step 320, calibration parameters can be defined using data from control healthy subjects. In some embodiments, sequence reads of a subject can be normalized against an overall average count from a group of subjects (e.g., a group of n baseline healthy subjects). For example, an overall average $\overline{Read}$ can be computed based on the average of every subject in the baseline control group, using the equation:

$$\overline{Read} = \sum_{i=1}^{i=n} \overline{Read}_{i/n}, \tag{3}$$

Here, $\overline{Read}_i$ is the average of a baseline healthy subject across different genomic regions, where integer i denotes a subject and is 1 through n. $\overline{Read}_i$ can be determined, for example, using equation (1).

In some embodiments, the overall average $\overline{Read}$ can be used to normalize the number of sequence reads bound to a particular region (x) for any future subject, for example, using the equation:

$$NormalizedRead = \overline{Read} \times SizeRegion(x) = w_x \times ActuralRead(x), \tag{4}$$

where ActuralRead(x) is the actual number of sequence reads aligned to region x, and $w_x$ is a weight assigned to the region to normalize the sequence reads to an expected value that can be obtained using an overall average.

In some embodiments, sequence reads for a subject corresponding to a particular region can be normalized against an averaged number of sequence reads for the same region across a group of healthy subjects (e.g., baseline healthy subjects of element 220). As an illustration, the sequence reads for region (j) for a subject i can be represented as $$Read_i^j,$$

where a subject i can be an integer from 1 to n. The average number of sequence reads for region (j) cross all subjects can be computed based on the following:

$$\overline{Read}^J = \sum_{i=1}^{i=n} Read_i^j / n. \tag{5}$$

Using this cross-subject average as a reference, the sequence reads for region (j) for any subject can be computed as:

$$NormalizedRead = \overline{Read}^J = w_j \times ActuralRead(j), \tag{6}$$

where ActuralRead(j) is the actual number of sequence reads aligned to region j, and $w_j$ is a weight assigned to the region to normalize the sequence reads to an expected value that can be obtained using average read $\overline{Read}^J$.

In some embodiments, sequence reads for a subject corresponding to a particular region can be calibrated any available methods, including using multiple approaches, utilizing both data from different regions for the subject itself and cross different control subjects. In some embodiments, a relative sequence read quantity can be used in the computation. For example, instead of the sequence reads $$\left(Read_i^j\right)$$

value observed, $$Read_i^j / \overline{Read}_t$$

will be used in subsequent analysis. Exemplary calibration methods further include but not limited to GC bias correction, correction of biases due to PCR over-amplification, and etc.

At step 322, quantities derived for each genomic region for each reference healthy subject can be calibrated using the parameters developed based on baseline healthy subjects; for example, those illustrated in the description for step 320. In some embodiments, calibrated data for the reference healthy subjects will be subject, to further analysis. In some embodiments, data for the reference healthy subjects may be further analysis without calibration based on baseline healthy subjects.

At step 324, one or more reference quantities can be computed for a genomic region of the reference genome based on the calibrated quantity data of all the reference healthy subjects for the particular genomic region. As disclosed herein, the reference quantities can be used to assess variability among the quantity data across all the reference healthy subjects for the particular genomic region. For example, for n quantities representing n reference healthy subjects, a first reference quantity representing all quantity data (e.g., an average, mean or medium) can be compared with a second reference quantity that reflect at least a characteristic of all quantity data being analyzed (e.g., a standard deviation (SD), median absolute deviation (MAD), or the interquartile range (IQR). For example, high variability may be indicated if the average of a reference quantity dataset differs drastically from the IQR of the same dataset.

At step 326, by specifying a condition between the first and second reference quantities, it is possible to determine whether data corresponding to a region has high or low variability. For example, this can be done by establishing a threshold value and compare it to the difference between the first and second reference quantities.

At step 328, the process of steps 318 to 326 is repeated for all genomic regions within the reference genome to identify genomic regions that are possibly associated with high variability. A high variability filter can be defined such that, when the filter is applied to test data, sequence reads that aligned to the high variability regions will be identified and excluded from further analysis. On the other hand, a low variability filter specifies genomic regions that exhibit low variability. When a low variability filter is applied to test data, sequence reads that aligned to the low variability regions will be identified and selected from further analysis.

The rationale behind the analysis is the hypothesis that normal variations between biological data of healthy subjects would tend to be smaller than systematic errors that occur during the processes of generating the biological data. In some embodiments, in order to avoid or reduce possible age-related variations, the healthy subjects in the reference control group are healthy young subjects of 35 or younger. As such, by locating those regions that may be associated with the most significant variations, one may eliminate the corresponding data from subsequent analysis to avoid or reduce systematic error, as indicated in step 308. As noted previously, the filter can be established in different ways to either allow exclusion of highly variable data or inclusion of data of low variability. In some embodiments, it is possible to adjust one or more threshold values in a filter to change the amount of the data that will be further analyzed.

In some embodiments, regions that will be removed from subsequent analysis include genomic regions that with GC content that is above a threshold value. In some embodiments, regions that will be removed from subsequent analysis include genomic regions that with GC content that is below a threshold value.

In some embodiments, a global high or low variability filter can be identified and applied, for example, across the entire genomic region. In some embodiments, a more refined filter can be determined for a more specific and smaller genomic region. For example, if a suspected condition is associated with only one or chromosome or a portion thereof, it is possible to set up a filter only with respect to the particle region.

As disclosed herein, a filter can be derived using quantities directly associated with the biological data or quantities derived therefrom.

Steps 330-336 specify an example illustrating how a portion of the training data can be quickly selected for further analysis by applying a low variability filter.

At step 330, sequence reads of cell-free nucleic acid samples from a training group are provided. The training group includes both healthy subjects and subjects who are known to have a certain medical condition (also referred to as "diseased subjects").

At step 332, sequence reads of the training group are aligned to genomic regions of the same reference genome.

From each region, a quantity can be derived based on the number of sequence reads that align to the particular region. In some embodiments, the quantity can be the total number of sequence reads aligned to the region. In some embodiments, the quantity can be a sequence read density value (e.g., the total number of sequence reads divided by the size of the region). In some embodiments, a relative count value can be computed; for example, the observed sequence read numbers can be normalized to the same region size and then divided by a control average sequence read value.

At step 334, quantity data derived at step 322 can be calibrated based on data from the baseline healthy subjects (e.g., correction of GC bias, normalization of count and much more). For example, the process illustrated in steps 314 through 322 can be applied.

At step 336, apply low variability filter defined after step 328 to the calibrated data. In some embodiments, only quantity data corresponding to the low variability regions are selected for further analysis. In some embodiments, instead of being discarded completely, data corresponding to high variability regions are assigned different weights to reflect their possible significance.

As disclosed herein, the region designation previous used for the baseline and/or reference healthy subjects can be used for subjects in the train group. As disclosed herein, during calibration at step 334, genomic region designation used for the baseline healthy subjects should preferably be applied to data from the training group. Similarly, during data selection at step 336, genomic region designation used for defining the low variability filter should be applied to data from the training group. For simplicity, the same region designation can be used for data from the baseline healthy subjects, the reference healthy subjects, and the training group.

After the process illustrated in FIGS. 3B and 3C is completed, data from the training group are pre-processed (e.g., normalized), the low variability filtered, and ready for further analysis. As disclosed herein, such data are referred to as filtered training data.

In one aspect, disclosed herein are method for analyzing data of high dimensionality to establish parameters that represent one or more characteristics of the data.

FIG. 4 depicts a sample process for analyzing data to reduce data dimensionality. The sample data analysis process 400 starts step 405 with filtered training data (e.g., training data treated according to the processes depicted in FIGS. 3A-3C). For example, for sequencing data, only data corresponding to the presumably low variability genomic regions are received at step 405. As disclosed herein, training data include data from healthy and diseased subjects. After a high or low variability filter has been applied the filtered training data should still include biological data from both healthy and diseased subjects. In some embodiments, the diseased subjects are patients who have been diagnosed with at least one type of cancer.

At step 410, the filtered training data are separated using cross-validation methods. In some embodiments, the cross validation methods include but are not limited to exhaustive methods like leave-p-out cross-validation (LpO CV) where p can have any value that would create a valid partition or leave-one-out cross validation (LOOCV) where p=1. In some embodiments, the cross validation methods include but are not limited to non-exhaustive methods such as the holdout method, repeated random sub-sampling validation method, or a stratified or non-stratified k-fold cross-validation method where k can have any value that would create a valid partitioning. As disclosed herein, a cross validation procedure partitions the filtered training data into different pairs of a training subset and a validation subset at a predetermined percentage split. For example, the first training subset and first validation subset depicted at step 410 represent an 80:20 split during one fold of a k-fold cross-validation experiment. In another fold of the same k-fold cross-validation experiment, the filtered training data will be split into a different pair of training and validation subsets at the same percentage ratio. In some embodiments, multiple cross-validation experiments are applied, where the split ratio of a pair of training and validation subsets can be varied in each experiment. As disclosed herein, the subsets can be created randomly. In some embodiments, the subsets are created such that each subset include data from both healthy and diseased subjects. In some embodiments, only one of the subsets include data from both healthy and diseased subjects. For example, it is essential that the training subset include both healthy and diseased subjects.

In some embodiments, a training subset constitutes a majority of the filtered training data; for example, up to 60%, up to 65%, up to 70%, up to 75%, up to 80%, up to 85%, up to 90%, or up to 95% of the filtered training data. In some embodiments, more than 95% of a very large set of filtered training data can be used as the training subset. To avoid training biases, it is usually good practice to save at least 5% of untouched data as a test subset; i.e., as this subset will never be used as training data and will only be used to validate the resulting model.

At step 415, data from the first training subset can be used to derive key features that capture one or more differences between the data of healthy and diseased subjects. In some embodiments, the data for each subject in the first training subset (e.g., counts of sequence reads or quantities derived therefrom) can be reduced in dimensionality before the key features can be derived from a reduced dataset. For example, samples that have been identified to have about 10,000 to about 20,000 of low variability regions can have 10,000 to 20,000 corresponding count values (or derived quantities such as a relative count value, a logCount value, and etc.). By using a method such as principal component analysis (PCA), it is possible to identify and select principal components (PCs) that represent the largest variations among data in the first training subset. These principal components (PCs) can be used to reduce the 10,000 to 20,000 count data to a lower dimensionality feature space where each feature corresponds to one of the selected PCs. In some embodiments, 5 or fewer PCs are selected. In some embodiments, 10 or fewer PCs are selected. In some embodiments, 15 or fewer PCs are selected. In some embodiments, 20 or fewer PCs are selected. In some embodiments, 25 or fewer PCs are selected. In some embodiments, 30 or fewer PCs are selected. In some embodiments, 35 or fewer PCs are selected. In some embodiments, 40 or fewer PCs are selected. In some embodiments, 45 or fewer PCs are selected. In some embodiments, 50 or fewer PCs are selected. In some embodiments, 60 or fewer PCs are selected. In some embodiments, 70 or fewer PCs are selected. In some embodiments, 80 or fewer PCs are selected. In some embodiments, 90 or fewer PCs are selected. In some embodiments, 100 or fewer PCs are selected. In some embodiments, more than 100 PCs are selected.

In some embodiments, the extracted features include the selected PCs. In some embodiments, the extracted features are the selected PCs. In some embodiments, the extracted features are the selected PCs in combination with other features; for example, the PCs can be individually weighted. In some embodiments, features other than PCs are selected.

At step 420, one or more parameters can be obtained to reflect the relative contribution of each of the extracted features to the differences in data in the first training subset. For example, for each selected principal component or PC, a weight is assigned to quantity data from each low variability region to reflect the respective importance of the data. A region contributing more to the observed differences will be assigned a larger weight; and vice versa. In some embodiments, the weight is PC-specific and region-specific, but the same for all subjects, for example, $w_k{}^j$ can represent the weight associated for region j in connection with PC k, where j is an integer from 1 to m', and m' is an integer smaller than m, the original number of genomic regions designated in the reference genome. This weight value is the same for different subjects. In some embodiments, more individualized weight value can be formulated to reflect differences between the subjects. For example, the weight may differ from one cancer type to another cancer type. For the same region and same PC, the weight for people of different ethnic origins can differ.

At step 425, data in the first training subset are transformed based on the extracted features (e.g., a few selected PCs). In some embodiments, dimensionality of the transformed data is much smaller than those of the filtered training data, whose dimensionality is already reduced from the original un-filtered data. The concepts are illustrated as follows.

$$\text{Subject}_1(\text{Read}) = \left[\text{Read}_1^1, \text{Read}_1^2, \text{Read}_1^3, \dots, \text{Read}_1^m\right] \quad (7)$$

Formula (7) illustrates that the data of subject 1 before a low variability filter is applied, where m is the total number of regions.

$$\text{Subject}_1(\text{FRead}) = \left[\text{FRead}_1^1, \text{FRead}_1^2, \text{FRead}_1^3, \dots, \text{FRead}_1^{m'}\right] \quad (8)$$

Formula (8) illustrates that the data of subject 1 before a low variability filter is applied, where m' is the total number of regions. After a low variability filter is applied, the total number of genomic regions is reduced to m', which can be significantly smaller than m. For example, un-filtered data for a subject can include 30,000 components or more, each associated with a genomic region. After a low variability filter is applied, a significant portion of the genomic regions can be excluded as being having high variability; for example, filtered data for the same subject can include 20,000 components or fewer, each associated with a low variability genomic region, as illustrated in (8).

At step 425, data dimensionality of the filtered data can be further reduced based on the number of feature extracted. For example, if k principal components are selected, the dimensionality of the filtered data can be reduced to k. As described in connection with step 415, the number of selected PCs can be much smaller than the dimensionality of the filtered data. For example, when only 5 PCs are selected, the data dimensionality of filtered read data (FRead) for subject 1 can be further reduced to 5, such as the expression in (9) below:

$$FRead_{PC1} = \sum_{j=1}^{j=m'} (w_{PC1}^j \times FRead_1^j)$$

$$FRead_{PC2} = \sum_{j=1}^{j=m'} (w_{PC2}^j \times FRead_1^j)$$

$$FRead_{PC3} = \sum_{j=1}^{j=m'} (w_{PC3}^j \times FRead_1^j)$$

$$FRead_{PC4} = \sum_{j=1}^{j=m'} (w_{PC4}^j \times FRead_1^j)$$

$$FRead_{PC5} = \sum_{j=1}^{j=m'} (w_{PC5}^j \times FRead_1^j)$$

As such, quantity data (e.g., read numbers) associated with a large number of low variability regions can be reduced and transformed to a handful of numeric values. In some embodiments, a weight can be assigned to each PC. In some embodiments, a single value can be computed based on the values associated with multiple PCs.

At step 430, a classification method is applied to the transformed data of each subject to provide a classification score. Any suitable algorithm described in connection with analysis module 150 and classification module 160 can be applied. In some embodiments, the classification score can be a binomial or tnultinornial probability score. For example, in a binomial classification for cancer, logistic regression can be applied to compute a probability score, where 0 represents no likelihood of cancer while 1 represents the highest certainty of having cancer. A score of over 0.5 indicates that the subject is more likely to have cancer than not having cancer. Logistic regression generates the coefficients (and its standard errors and significance levels) of a formula to predict a logit transformation of the probability of presence of the characteristic of interest. Using the same example to illustrate probability determination by logistic regression, the probability (p) of a subject having cancer can be written as the following in equation (10):

$$\text{logit}(p) = b_0 + b_1 \times FRead_{PC1} + b_2 \times FRead_{PC2} + b_3 \times FRead_{PC3} + b_4 \times FRead_{PC4} + b_5 \times FRead_{PC5} \quad (10)$$

where each transformed and reduced data derived from PC1 is assigned a weight. The logit transformation is defined as the logged odds in equation (11):

$$\text{odds} = \frac{p}{1-p} = \frac{\text{probability of cancer being present}}{\text{probability of cancer being absent}} \quad (11)$$

and probability p in equation (12)

$$p = \frac{1}{1 + e^{-\text{logit}(p)}} \quad (12)$$

The value of p can be computed using equation (12) by plugging the value from equation (10). In some embodiments, it is possible to look up values in a logit table.

In some embodiments, a multinomial classification approach can be taken to classify subjects into different cancer type. For example, existing multinomial classification techniques can be categorized into (i) transformation to binary (ii) extension from binary and (iii) hierarchical classification. In a transformation to binary approach, a multi-class problem can be transformed into multiple binary problems based on a one-vs-rest or one-vs-one approach. Exemplary extension from binary algorithms include but are not limited to neural networks, decision trees, k-nearest neighbors, naive Bayes, support vector machines and Extreme Learning Machines, and etc. Hierarchical classification tackles the multinomial classification problem by dividing the output space i.e. into a tree. Each parent node is divided into multiple child nodes and the process is continued until each child node represents only one class. Several methods have been proposed based on hierarchical classification. In some embodiments, multinomial logistic regression can be applied. It is used to predict the probabilities of the different possible outcomes of a categorically distributed dependent variable, given a set of independent variables (which may be real-valued, binary-valued, categorical-valued, etc.).

At step 435, the filtered training data are partitioned into a second training subset and a second test/validation subset and the steps of 410 through 430 are repeated in one or more refinement cycles (also referred to as "one or more cross-validation cycles"). As disclosed herein, in the cross-validation procedure the validation subsets themselves have little (e.g., in repeated random sampling) or no overlap at all (LOOCV, LpO CV, k-fold) over different folds.

During a refinement cycle, a predetermined condition (e.g., a cost function) can be applied to optimize the classification results. In some embodiments, one or more parameters in a classification function are refined using training data subset and validated by validation or held out subset during each fold of the cross-validation procedure. In some embodiments, PC-specific weights and/or region-specific weights can be refined to optimize classification results.

In some embodiments, a small portion of the filtered training data can be kept aside, not as a part of a training subset during any fold of the cross-validation procedure to better estimate overfitting.

At step 440, the refined parameters are used to compute classification scores. As disclosed herein, the refined parameters can function as a prediction model for cancer as well as cancer types. It is possible to construct a prediction model using multiple types of biological data; including but not limited to, for example, nucleic acid sequencing data (cell-free versus non cell-free, whole genome sequencing data, whole genome methylation sequencing data, RNA sequencing data, targeted panel sequencing data), protein sequencing data, tissue pathology data, family history data, epidemiology data, and etc.

In one aspect, disclosed herein are method for classifying a subject as having a certain medical condition, based on parameters established using training data.

Figure 5:
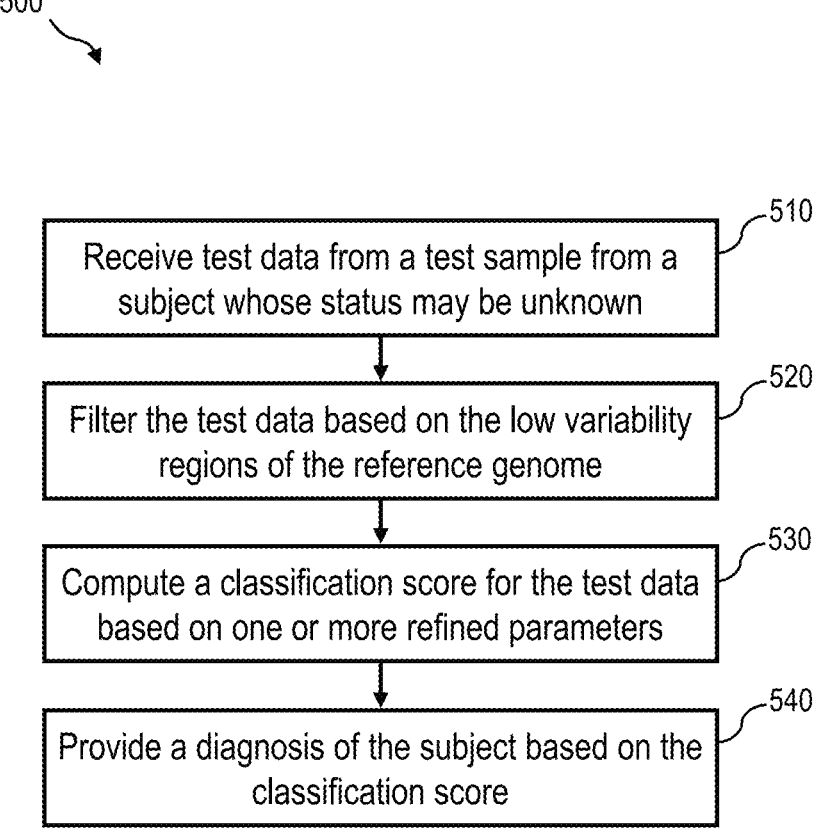
FIG. 5 depicts a sample process for analyzing data based on information learned from data with reduced dimensionality.

FIG. 5 depicts a sample process for analyzing data based on information learned from data with reduced dimensionality. Process 500 illustrates how test data from a subject, whose status with respect to a medical condition is unknown, can be used to compute a classification score and serve as a basis for diagnosing whether the subject is likely to have the condition.

At step 510, test data is received from a test sample from the subject who status is unknown. In some embodiments, the test data are of the same type as those from the baseline healthy subjects including. In some embodiments, the test data are of the same type as those from the reference healthy subjects. Sample data type includes but not limited to sequencing data for detecting targeted mutations, whole genome sequencing data, RNA sequencing data, and whole genome sequencing data for detecting methylation. In some embodiments, the test data can be calibrated and adjusted for improved quality (e.g., normalization, GC content correction and etc.).

At step 520, data selection is performed using a previously defined low variability filter. Advantageously, the filter-based approach is straight-forward and can be easily adjusted by changing the threshold value of the reference quantities computed for genomic regions in a reference genome.

At step 530, a classification score can be computed for the test subject based on the parameters previously determined based on training data (e.g., the refined parameters obtained at step 435). The previously determined parameters can form a prediction model for cancer and specific type of cancer.

At step 540, a diagnosis can be provided to the test based on the classification score. In some embodiments, the parameters are determined for cancer versus non-cancer diagnosis. In some embodiments, the parameters are determined for cancer type diagnosis.

As noted previously, the current method can be applied to any suitable biological data, especially nucleic acid sequencing data. In some embodiments, multiple types of data can be used to construct the prediction model, including but not limited to nucleic acid sequencing data (cell-free versus non cell-free, whole genome sequencing data, whole genome methylation sequencing data, RNA sequencing data, targeted panel sequencing data), protein sequencing data, tissue pathology data, family history data, epidemiology data, and etc.

In one aspect, disclosed herein are method for analyzing high dimensionality data at multiple levels and using results from such analyses to perform classification.

Figure 6:
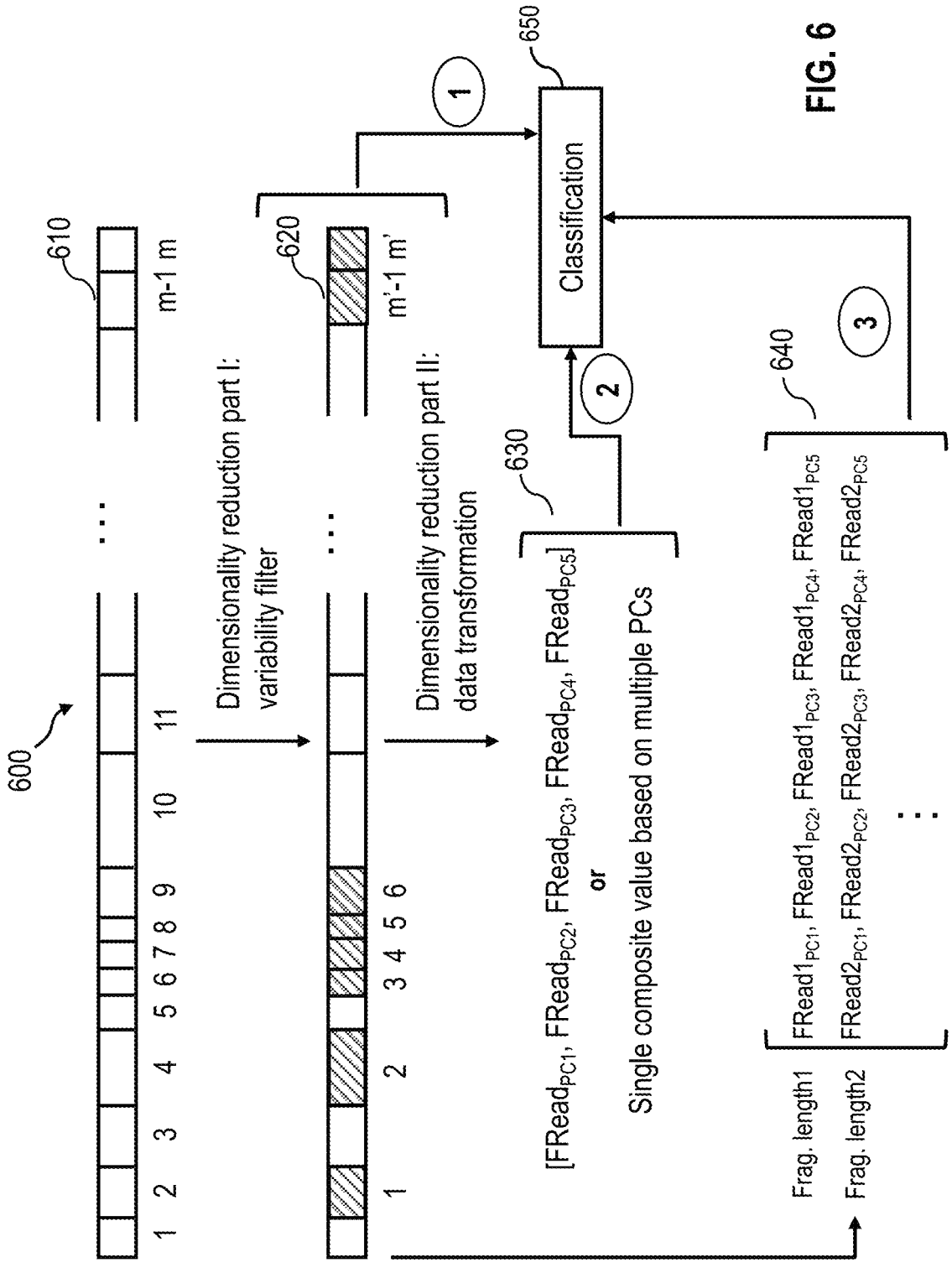
FIG. 6 depicts a sample process for data analysis in accordance with the current disclosure.

FIG. 6 depicts a sample process for data analysis in accordance with the current disclosure. As described in detail in connection with FIGS. 3 and 4, reduction of dimensionality can take place during multiple points of the data analysis.

In some embodiments, a certain level of data selection can occur during initial data processing: e.g., during normalization, GC content correction, and other initial data calibration steps, it is possible to rejects sequence reads that are clearly defective and thus reduce the number of data. As illustrated, in sample process 600, data dimensionality reduction can take place with the application of a low or high variability filter. For example, a reference genome can be divided into a number of regions. The regions can be equal or non-equal in size (e.g., element 610 in FIG. 6).

As disclosed herein, a low variability filter specifies a subset of the genomic regions from 610 that will be selected for further processing (e.g., highlighted regions in element 620). Using, the highlighted combination genomic regions, a filter allows categorical selection or rejection of data based on established analysis of possible systematic errors using reference healthy subjects.

The selected data are then transformed to further reduce data dimensionality (e.g., element 630 in FIG. 6). In some embodiments, transformed data 630 can be generated using data from all the selected genomic regions, but the dimensionality of data can be greatly reduced. For example, data from over 20,000 different genomic regions can be transformed into a handful of values. In some embodiments, a single value can be generated.

In some embodiments, selected sequencing data from element 620 can be sorted in subgroups according to the fragment size represented by the sequencing data. For example, instead of a single count for all sequence reads bound to a particular region, multiple quantiles can be derived each corresponding to a size or size range. For example, sequence reads corresponding to fragments of 140-150 bases will be separately grouped from sequence reads corresponding to fragments of 150-160 bases, as illustrated in element 640 in FIG. 6. As such, additional detail and fine tuning can be made before the data are used for classification.

As illustrated in FIG. 6, multiple types of data can be used for classification (e.g., element 650 in FIG. 6), including but not limited to data from selected/filtered genomic regions without dimensionality reduction, reduced data, reduced and sorted data, and etc.

The current method and system offer advantages over previously known methods. For example, classification is done using quantities that can be easily derived from raw sequencing data. The current does not require building chromosome-specific segmentation maps, thus eliminating the time-consuming process for generating those maps. Also, the current method permits more efficient use of computer storage space because it no longer requires storage for the large segmentation maps.

Figure 12A:
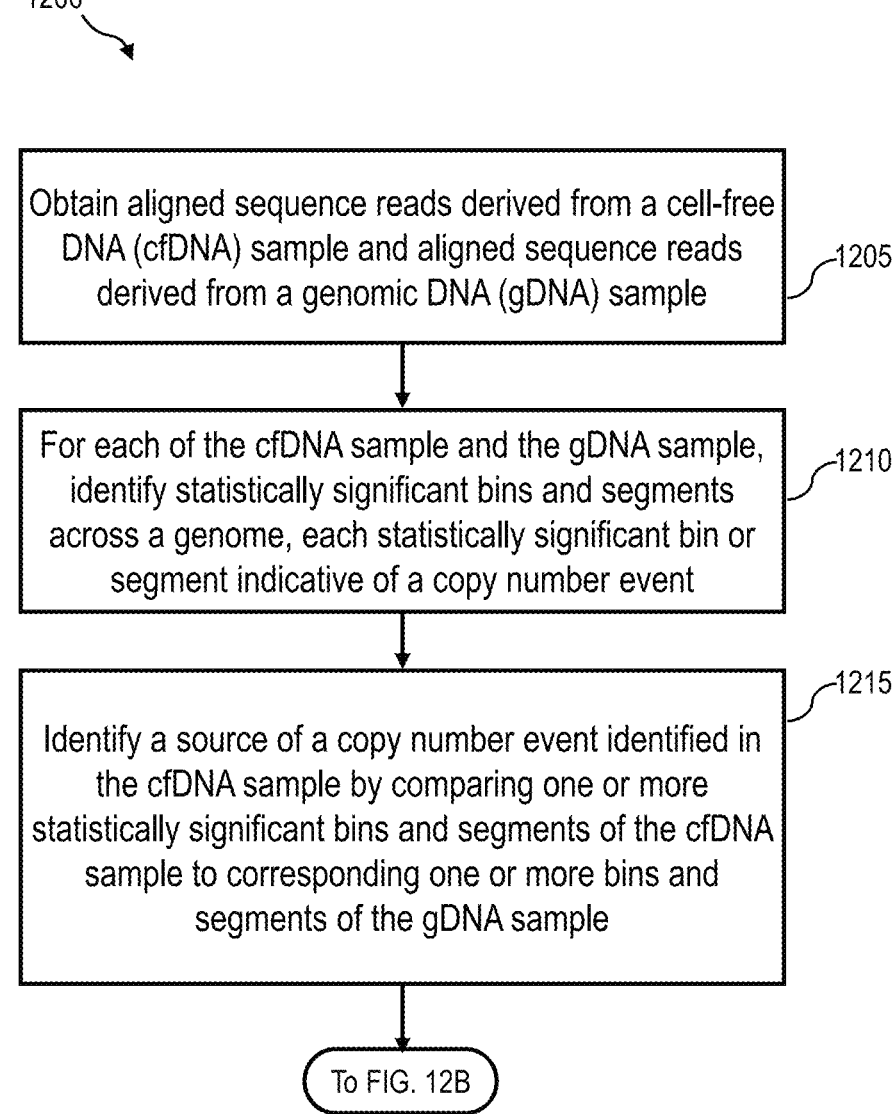
FIG. 12A depicts a sample process for identifying a source of a copy number event identified in a cfNA sample.

FIG. 12A is an example flow process 1200 for identifying a source of a copy number event identified in a cfNA sample, in accordance with an embodiment. Specifically, FIG. 12A depicts exemplary steps for detecting a CNA in an individual.

Cell-free DNA (cfDNA) and genomic DNA (gDNA) are extracted from a test sample and sequenced (e.g., using whole exome or whole genome sequencing) to obtain sequence reads. cfDNA sequence reads and gDNA sequence reads are separately analyzed to identify the possible presence of one or more copy number events in each respective sample. Here, the source of copy number events derived from cfDNA can be any one of a germline source, somatic non-tumor source, or somatic tumor source. The source of copy number events derived from gDNA can be either a germline source or a somatic non-tumor source. Therefore, copy number events detected in cfDNA but not detected in gDNA can be readily attributed to a somatic tumor source.

At step 1205, aligned sequence reads derived from a cfDNA sample (hereafter referred to as cfDNA sequence reads) and aligned sequence reads derived from a gDNA sample (hereafter referred to as gDNA sequence reads) are obtained.

At step 1210, the aligned cfDNA sequence reads and gDNA sequence reads are analyzed to identify statistically significant bins and segments across a reference genome for each of the cfDNA sample and gDNA sample, respectively. A bin includes a range of nucleotide bases of a genome. A segment refers to one or more bins. Therefore, each sequence read is categorized in bins and/or segments that include a range of nucleotide bases that corresponds to the sequence read. Each statistically significant bin or segment of the genome includes a total number of sequence reads categorized in the bin or segment that is indicative of a copy number event. Generally, a statistically significant bin or segment includes a sequence read count that significantly differs from an expected sequence read count for the bin or segment even when accounting for possibly confounding factors, examples of which includes processing biases, variance in the bin or segment, or an overall level of noise in the sample (e.g., cfDNA sample or gDNA sample). Therefore, the sequence read count of a statistically significant bin and/or a statistically significant segment likely indicates a biological anomaly such as a presence of a copy number event in the sample.

Step 1210 includes both a bin-level analysis to identify statistically significant bins as well as a segment-level analysis to identify statistically significant segments. Performing analyses at the bin and segment level enables the more accurate identification of possible copy number events. In some embodiments, solely performing an analysis at the bin level may not be sufficient to capture copy number events that span multiple bins. In other embodiments, solely performing an analysis at the segment level may yield an analysis that is not sufficiently granular enough to capture copy number events whose size are on the order of individual bins.

Figure 12B:
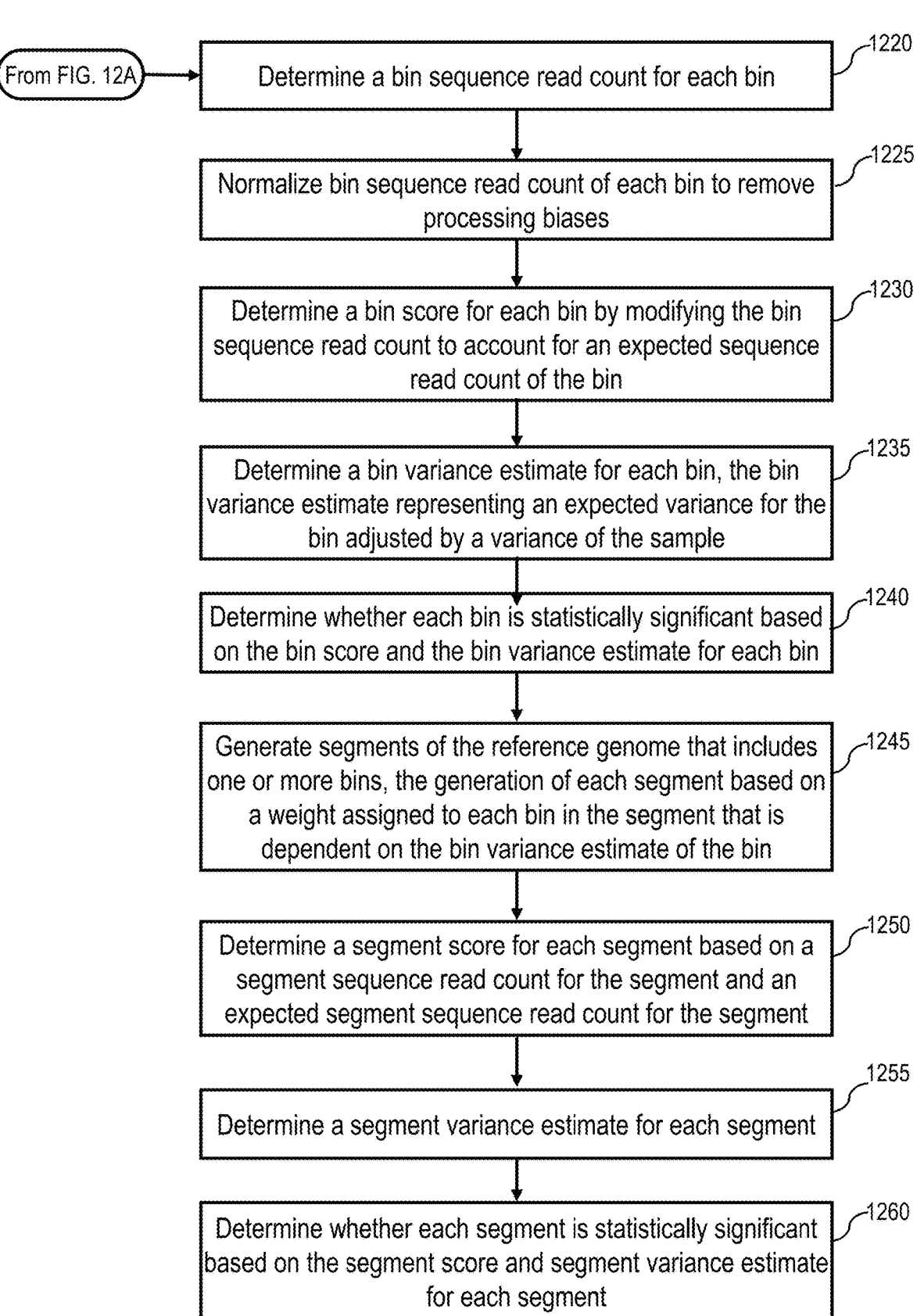
FIG. 12B depicts a sample process for identifying statistically significant bins and statistically significantly segments derived from cfDNA and gDNA samples, in accordance with an embodiment of the present disclosure.

Generally, the analysis of cfDNA sequence reads and the analysis of gDNA sequence reads are conducted independent of one another. In various embodiments, the analysis of cfDNA sequence reads and gDNA sequence reads are conducted in parallel. In some embodiments, the analysis of cfDNA sequence reads and gDNA sequence reads are conducted at separate times depending on when the sequence reads are obtained (e.g., when sequence reads are obtained in step 1205). Reference is now made to FIG. 12B, which is an example flow process that describes the analysis for identifying statistically significant bins and statistically significantly segments derived from cfDNA and gDNA samples, in accordance with an embodiment. Specifically, FIG. 12B depicts steps included in step 1210 shown in FIG. 12A. Therefore, steps 1220-1260 can be performed for a cfDNA sample and similarly, steps 1220-1260 can be separately performed for a gDNA sample.

At step 1220, a bin sequence read count is determined for each bin of a reference genome. Generally, each bin represents a number of contiguous nucleotide bases of the genome. A genome can be composed of numerous bins (e.g., hundreds or even thousands). In some embodiments, the number of nucleotide bases in each bin is constant across all bins in the genome. In some embodiments, the number of nucleotide bases in each bin differs for each bin in the genome. In one embodiment, the number of nucleotide bases in each bin is between 25 kilobases (kb) and 200 kb. In one embodiment, the number of nucleotide bases in each bin is between 40 kb and 100 kb. In one embodiment, the number of nucleotide bases in each bin is between 45 kb and 75 kb. In one embodiment, the number of nucleotide bases in each bin is 50 kb. In practice, other bin sizes may be used as well.

Returning to FIG. 12B, at step 1225, the bin sequence read count for each bin is normalized to remove one or more different processing biases. Generally, the bin sequence read count for a bin is normalized based on processing biases that were previously determined for the same bin. In one embodiment, normalizing the bin sequence read count involves dividing the bin sequence read count by a value representing the processing bias. In one embodiment, normalizing the bin sequence read count involves subtracting a value representing the processing bias from the bin sequence read count. Examples of a processing bias for a bin can include guanine-cytosine (GC) content bias, mappability bias, or other forms of bias captured through a principal component analysis. Processing biases for a bin can be accessed from the processing biases store 1270 shown in FIG. 12C.

At step 1230, a bin score for each bin is determined by modifying the bin sequence read count for the bin by the expected bin sequence read count for the bin. Step 1230 serves to normalize the observed bin sequence read count such that if the particular bin consistently has a high sequence read count (e.g., high expected bin sequence read counts) across many samples, then the normalization of the observed bin sequence read count accounts for that trend. The expected sequence read count for the bin can be accessed from the bin expected counts store 280 in the training characteristics database 1265 (see FIG. 12C). The generation of the expected sequence read count for each bin is described in further detail below.

In one embodiment, a bin score for a bin can be represented as the log of the ratio of the observed sequence read count for the bin and the expected sequence read count for the bin. For example, bin score $b_i$ for bin i can be expressed as:

$$b_i = \log\left(\frac{\text{observed bin sequence read count}}{\text{expected bin sequence read count}}\right) \quad (13)$$

In other embodiments, the bin score for the bin can be represented as the ratio between the observed sequence read count for the bin and the expected sequence read count for the bin $$\left(e.g., \frac{\text{observed}}{\text{expected}}\right),$$

the square root of the ratio $$\left(e.g., \sqrt{\frac{\text{observed}}{\text{expected}}}\right),$$

a generalized log transformation (g log) of the ratio (e.g., $\log(\text{observed} + \sqrt{\text{observed}^2 + \text{expected}})$) or other variance stabilizing transforms of the ratio.

Returning to FIG. 12B, at step 1235, a bin variance estimate is determined for each bin. Here, the bin variance estimate represents an expected variance for the bin that is further adjusted by an inflation factor that represents a level of variance in the sample. Put another way, the bin variance estimate represents a combination of the expected variance of the bin that is determined from prior training samples as well as an inflation factor of the current sample (e.g., cfDNA or gDNA sample) which is not accounted for in the expected variance of the bin.

To provide an example, a bin variance estimate ($\text{var}_i$) for a bin i can be expressed as:

$$\text{var}_i = \text{var}_{exp_i} * I_{sample} \quad (14)$$

where $\text{var}_{exp_i}$ represents the expected variance of bin i determined from prior training samples and $I_{sample}$ represents the inflation factor of the current sample. Generally, the expected variance of a bin (e.g., $\text{var}_{exp}$) is obtained by accessing the bin expected variance store 1290 shown in FIG. 12C.

Figure 12C:
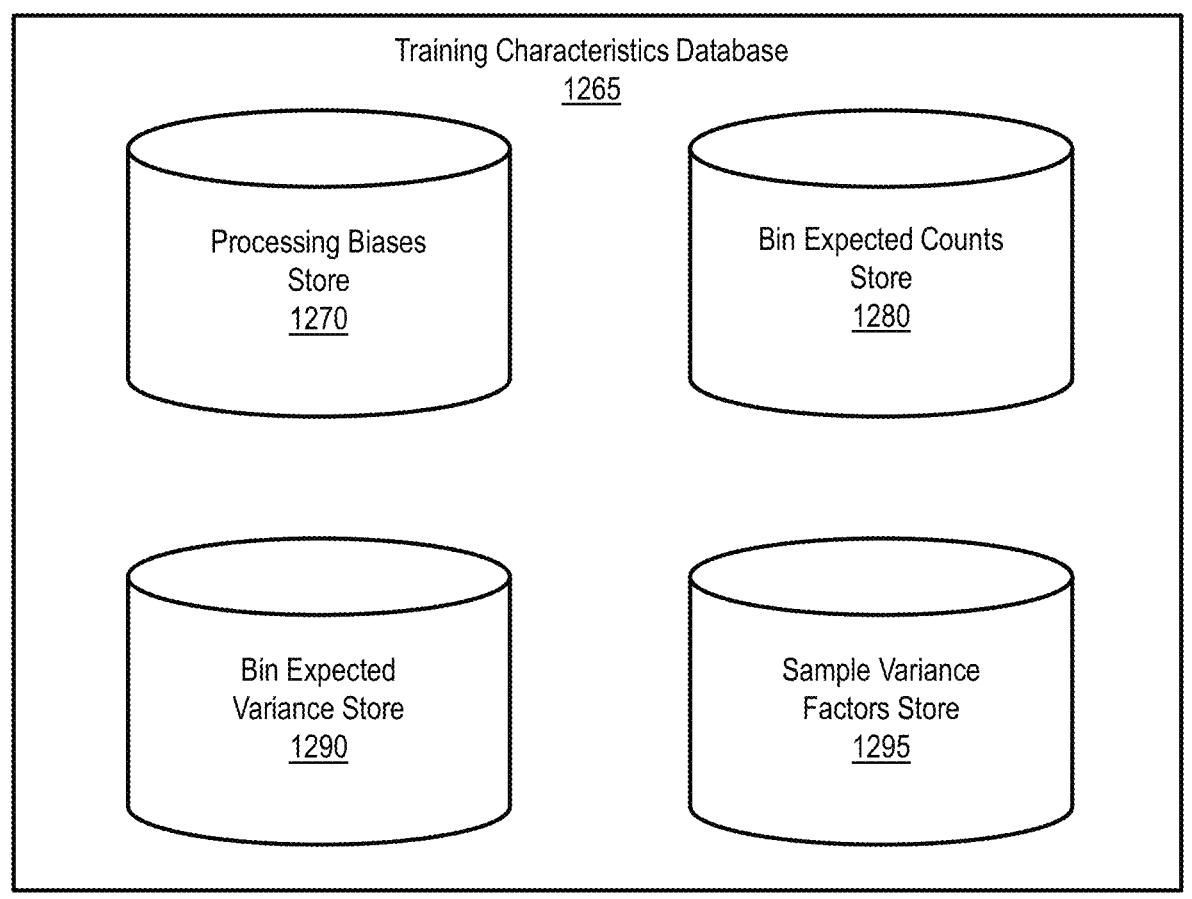
FIG. 12C depicts a diagram of an example system architecture for a training characteristics database, in accordance with an embodiment of the present disclosure.

To determine the inflation factor $I_{sample}$ of the sample, a deviation of the sample is determined and combined with sample variation factors that are retrieved from the sample variation factors store 1295 shown in FIG. 12C. Sample variation factors are coefficient values that are previously derived by performing a fit across data derived from multiple training samples. For example, if a linear fit is performed, sample variation factors can include a slope coefficient and an intercept coefficient. If higher order fits are performed, sample variation factors can include additional coefficient values.

The deviation of the sample represents a measure of variability of sequence read counts in bins across the sample. In one embodiment, the deviation of the sample is a median absolute pairwise deviation (MAPD) and can be calculated by analyzing sequence read counts of adjacent bins. Specifically, the MAPD represents the median of absolute value differences between bin scores of adjacent bins across the sample. Mathematically, the MAPD can be expressed as:

$$\forall \, (\text{bin}_i, \text{bin}_{i+1}), \, MAPD = \text{median}\{|(b_i) - (b_{i+1})|\} \quad (15)$$

where $b_i$ and $b_{i+1}$ are the bin scores for bin i and bin i+1 respectively.

The inflation factor $I_{sample}$ is determined by combining the sample variation factors and the deviation of the sample (e.g., MAPD). As an example, the inflation factor $I_{sample}$ of a sample can be expressed as:

$$I_{sample} = \text{slope} * \sigma_{sample} + \text{intercept}. \quad (16)$$

Here, each of the "slope" and "intercept" coefficients are sample variation factors accessed from the sample variation factors store 1295 whereas $\sigma_{sample}$ represents the deviation of the sample.

At step 1240, each bin is analyzed to determine whether the bin is statistically significant based on the bin score and bin variance estimate for the bin. For each bin i, the bin score ($b_i$) and the bin variance estimate ($\text{var}_i$) of the bin can be combined to generate a z-score for the bin. An example of the z-score ($z_i$) of bin i can be expressed as:

$$z_i = \frac{b_i}{\text{var}_i} \quad (17)$$

To determine whether a bin is a statistically significant bin, the z-score of the bin is compared to a threshold value. If the z-score of the bin is greater than the threshold value, the bin is deemed a statistically significant bin. Conversely, if the z-score of the bin is less than the threshold value, the bin is not deemed a statistically significant bin. In one embodiment, a bin is determined to be statistically significant if the z-score of the bin is greater than 2. In other embodiments, a bin is determined to be statistically significant if the z-score of the bin is greater than 2.5, 3, 3.5, or 4. In one embodiment, a bin is determined to be statistically significant if the z-score of the bin is less than −2. In other embodiments, a bin is determined to be statistically significant if the z-score of the bin is less than −2.5, −3, −3.5, or −4. The statistically significant bins can be indicative of one or more copy number events that are present in a sample (e.g., cfDNA or gDNA sample).

At step 1245, segments of the reference genome are generated. Each segment is composed of one or more bins of the reference genome and has a statistical sequence read count. Examples of a statistical sequence read count can be an average bin sequence read count, a median bin sequence read count, and the like. Generally, each generated segment of the reference genome possesses a statistical sequence read count that differs from a statistical sequence read count of an adjacent segment. Therefore, a first segment may have an average bin sequence read count that significantly differs from an average bin sequence read count of a second, adjacent segment.

In various embodiments, the generation of segments of the reference genome can include two separate phases. A first phase can include an initial segmentation of the reference genome into initial segments based on the difference in bin sequence read counts of the bins in each segment. The second phase can include a re-segmentation process that involves recombining one or more of the initial segments into larger segments. Here, the second phase considers the lengths of the segments created through the initial segmentation process to combine false-positive segments that were a result of over-segmentation that occurred during the initial segmentation process.

Referring more specifically to the initial segmentation process, one example of the initial segmentation process includes performing a circular binary segmentation algorithm to recursively break up portions of the reference genome into segments based on the bin sequence read counts of bins within the segments. In other embodiments, other algorithms can be used to perform an initial segmentation of the reference genome. As an example of the circular binary segmentation process, the algorithm identifies a break point within the reference genome such that a first segment formed by the break point includes a statistical bin sequence read count of bins in the first segment that significantly differs from the statistical bin sequence read count of bins in the second segment formed by the break point. Therefore, the circular binary segmentation process yields numerous segments, where the statistical bin sequence read count of bins within a first segment is significantly different from the statistical bin sequence read count of bins within a second, adjacent segment.

The initial segmentation process can further consider the bin variance estimate for each bin when generating initial segments. For example, when calculating a statistical bin sequence read count of bins in a segment, each bin i can be assigned a weight that is dependent on the bin variance estimate (e.g., $var_i$) for the bin. In one embodiment, the weight assigned to a bin is inversely related to the magnitude of the bin variance estimate for the bin. A bin that has a higher bin variance estimate is assigned a lower weight, thereby lessening the impact of the bin's sequence read count on the statistical bin sequence read count of bins in the segment. Conversely, a bin that has a lower bin variance estimate is assigned a higher weight, which increases the impact of the bin's sequence read count on the statistical bin sequence read count of bins in the segment.

Referring now to the re-segmenting process, it analyzes the segments created by the initial segmentation process and identifies pairs of falsely separated segments that are to be recombined. The re-segmentation process may account for a characteristic of segments not considered in the initial segmentation process. As an example, a characteristic of a segment may be the length of the segment. Therefore, a pair of falsely separated segments can refer to adjacent segments that, when considered in view of the lengths of the pair of segments, do not have significantly differing statistical bin sequence read counts. Longer segments are generally correlated with a higher variation of the statistical bin sequence read count. As such, adjacent segments that were initially determined to each have statistical bin sequence read counts that differed from the other can be deemed as a pair of falsely separated segments by considering the length of each segment.

Falsely separated segments in the pair are combined. Thus, performing the initial segmentation and re-segmenting processes results in generated segments of a reference genome that takes into consideration variance that arises from differing lengths of each segment.

At step 1250, a segment score is determined for each segment based on an observed segment sequence read count for the segment and an expected segment sequence read count for the segment. An observed segment sequence read count for the segment represents the total number of observed sequence reads that are categorized in the segment. Therefore, an observed segment read count for the segment can be determined by summating the observed bin read counts of bins that are included in the segment. Similarly, the expected segment sequence read count represents the expected sequence read counts across the bins included in the segment. Therefore, the expected segment sequence read count for a segment can be calculated by quantifying the expected bin sequence read counts of bins included in the segment. The expected read counts of bins included in the segment can be accessed from the bin expected counts store 1280.

The segment score for a segment can be expressed as the ratio of the segment sequence read count and the expected segment sequence read count for the segment. In one embodiment, the segment score for a segment can be represented as the log of the ratio of the observed sequence read count for the segment and the expected sequence read count for the segment. Segment score $s_k$ for segment k can be expressed as:

$$s_k = \log\left(\frac{\text{observed segment sequence read count}}{\text{expected segment sequence read count}}\right) \quad (18)$$

In other embodiments, the segment score for the segment can be represented as one of the square root of the ratio $$\left(\text{e.g., } \sqrt{\frac{\text{observed}}{\text{expected}}}\right),$$

a generalized log transformation of the ratio (e.g., log (observed+$\sqrt{\text{observed}^2+\text{expected}}$)) or other variance stabilizing transforms of the ratio.

At step 1255, a segment variance estimate is determined for each segment. Generally, the segment variance estimate represents how deviant the sequence read count of the segment is. In one embodiment, the segment variance estimate can be determined by using the bin variance estimates of bins included in the segment and further adjusting the bin variance estimates by a segment inflation factor ($I_{Segment}$). To provide an example, the segment variance estimate for a segment k can be expressed as:

$$var_k = \text{mean}(var_i) * I_{segment} \quad (19)$$

where mean(var$_i$) represents the mean of the bin variance estimates of bins i that are included in segment k. The bin variance estimates of bins can be obtained by accessing the bin expected variance store 1290.

The segment inflation factor accounts for the increased deviation at the segment level that is typically higher in comparison to the deviation at the bin level. In various embodiments, the segment inflation factor may scale according to the size of the segment. For example, a larger segment composed of a large number of bins would be assigned a segment inflation factor that is larger than a segment inflation factor assigned to a smaller segment composed of fewer bins. Thus, the segment inflation factor accounts for higher levels of deviation that arises in longer segments. In various embodiments, the segment inflation factor assigned to a segment for a first sample differs from the segment inflation factor assigned to the same segment for a second sample. In various embodiments, the segment inflation factor $I_{segment}$ for a segment with a particular length can be empirically determined in advance.

In various embodiments, the segment variance estimate for each segment can be determined by analyzing training samples. For example, once the segments are generated in step 1245, sequence reads from training samples are analyzed to determine an expected segment sequence read count for each generated segment and an expected segment variance estimate for each segment.

The segment variance estimate for each segment can be represented as the expected segment variance estimate for each segment determined using the training samples adjusted by the sample inflation factor. For example, the segment variance estimate (var$_k$) for a segment k can be expressed as:

$$var_k = var_{exp_k} * I_{sample} \tag{20}$$

where $var_{exp_k}$ is the expected segment variance estimate for segment k and $I_{sample}$ is the sample inflation factor described above in relation to step 1235 and Equation (4).

At step 1260, each segment is analyzed to determine whether the segment is statistically significant based on the segment score and segment variance estimate for the segment. For each segment k, the segment score ($s_k$) and the segment variance estimate (var$_k$) of the segment can be combined to generate a z-score for the segment. An example of the z-score ($z_k$) of segment k can be expressed as:

$$z_k = \frac{s_k}{var_k} \tag{21}$$

To determine whether a segment is a statistically significant segment, the z-score of the segment is compared to a threshold value. If the z-score of the segment is greater than the threshold value, the segment is deemed a statistically significant segment. Conversely, if the z-score of the segment is less than the threshold value, the segment is not deemed a statistically significant segment. In one embodiment, a segment is determined to be statistically significant if the z-score of the segment is greater than 2. In other embodiments, a segment is determined to be statistically significant if the z-score of the segment is greater than 2.5, 3, 3.5, or 4. In some embodiments, a segment is determined to be statistically significant if the z-score of the segment is less than −2. In other embodiments, a segment is determined to be statistically significant if the z-score of the segment is less than −2.5, −3, −3.5, or −4. The statistically significant segments can be indicative of one or more copy number events that are present in a sample (e.g., cfDNA or gDNA sample).

Returning to FIG. 12A, at step 1215, a source of a copy number event indicated by statistically significant bins (e.g., determined at step 1240) and/or statistically significant segments (e.g., determined at step 1260) derived from the cfDNA sample is determined. Specifically, statistically significant bins of the cfDNA sample are compared to corresponding bins of the gDNA sample. Additionally, statistically significant segments of the cfDNA sample are compared to corresponding segments of the gDNA sample.

The comparison between statistically significant segments and bins of the cfDNA sample and corresponding segments and bins of the gDNA sample yields a determination as to whether the statistically significant segments and bins of the cfDNA sample align with the corresponding segments and bins of the gDNA sample. As used hereafter, aligned segments or bins refers to the fact that the segments or bins are statistically significant in both the cfDNA sample and the gDNA sample. On the contrary, unaligned or not aligned segments or bins refers to the fact that the segments or bins are statistically significant in one sample (e.g., cfDNA sample), but is not statistically significant in another sample (e.g., gDNA sample).

Generally, if statistically significant bins and statistically significant segments of the cfDNA sample are aligned with corresponding bins and segments of the gDNA sample that are also statistically significant, this indicates that the same copy number event is present in both the cfDNA sample and the gDNA sample. Therefore, the source of the copy number event is likely you number event is likely a copy number variation.

Conversely, if statistically significant bins and statistically significant segments of the cfDNA sample are aligned with corresponding bins and segments of the gDNA sample that are not statistically significant, this indicates that the copy number event is present in the cfDNA sample but is absent from the gDNA sample. In this scenario, the source of the copy number event in the cfDNA sample is due to a somatic tumor event and the copy number event is a copy number aberration.

Identifying the source of a copy number event that is detected in the cfDNA sample is beneficial in filtering out copy number events that are due to a germline or somatic non-tumor event. This improves the ability to correctly identify copy number aberrations that are due to the presence of a solid tumor.

In some aspects, size-selected cell-free DNA (cfDNA) sequence reads are used in the methods for analyzing sequence reads of nucleic acid samples in connection with a disease condition disclosed herein. The size selection can be achieved by either in vitro selection of cfDNA of a particular size range, i.e., prior to generating sequencing data, or in silico filtering of sequence read data.

Advantageously, it was discovered that use of size-selected cfDNA sequencing data improved the sensitivity of disease classifiers that were based on information derived from regions of low variability in a reference genome. For instance, as described in detail below, selection of sequencing data of cfDNA fragments from cancer patients, using a ceiling cut-off value of less than 160 nucleotides, significantly increased the fraction of cancer-derived sequence reads in the data set. Further, despite that size selection significantly reduces the sequence coverage of the data set, as well as the total number of sequence reads of cancer-derived cfDNA, use of size-selected sequencing data yields higher sensitivity when applied to a cancer status classifier that was based on information derived from regions of low variability in the human genome.

Accordingly, various methodologies are described herein that improve the confidence with which a cancer classification is made. In fact, some of these methodologies not only improve the confidence with which the cancer classification is made, but also reduce the amount of DNA sequencing data required for the classification which, in turn, improves the speed of the process while reducing the cost and computational burden of the analysis.

In one aspect, the disclosure provides improved systems and methods for classifying a subject for a cancer condition based on analysis of sequence reads of cell-free DNA, from a biological sample of the subject, that are filtered in silico to enrich for sequence reads from cancer cell-derived fragments, e.g., by removing sequence reads of cell-free DNA fragments that are larger than a threshold length that is less than 160 nucleotides. Advantageously, because the filtered set of sequence reads includes fewer sequence reads than the full set of sequence reads obtained from sequencing the cell-free DNA from the sample, the computational burden of processing the data set and applying the processed data to a classifier is reduced, improving the efficiency of computer systems used to classify the cancer state of a subject and reducing the overall time. Moreover, it was unexpectedly found that the confidence with which the classifications are made were improved by using the filtered data sets, despite that a significant portion of the available data is removed through the filtration process. For instance, as described in Examples 6 and 7, the use of sequencing data that is filtered in silico to remove sequence reads from cfDNA molecules having lengths of more than 150 nucleotides improves the sensitivity of cancer detection using a classifier based on copy number variation of a predetermined number of genomic bins with low variability in a reference human genome. Specifically, FIGS. 17A-17D and 17F-17G show increased sensitivity of the classification at 95%, 98%, and 99% specificity, using sequencing data from cfDNA fragments of 1-100 nucleotides, 0-140 nucleotides, 90-140, and 90-150 nucleotides.

Figure 19:
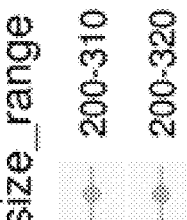
FIG. 19 illustrates the estimated fraction of cancer-derived cfDNA fragments (tumor fraction) in samples before (x-axis) and after (y-axis) in vitro size selection, as described in Example 9.

In one aspect, the disclosure provides improved systems and methods for classifying a subject for a cancer condition based on analysis of sequence reads of cell-free DNA, from a biological sample of the subject, that are size selected in vitro to remove cell-free DNA fragments that are larger than a threshold length, e.g., that is less than 160 nucleotides. Advantageously, because the cell-free DNA from the biological sample is size selected, the total amount of DNA that needs to be sequenced is reduced. In turn, more samples can be combined in a single sequencing reaction, reducing the sequencing cost and time per sample. Further, because fewer sequence reads are generated from each sample, the computational burden of processing the data set and applying the processed data to a classifier is reduced, improving the efficiency of computer systems used to classify the cancer state of a subject and reducing the overall time. Moreover, it was unexpectedly found that the confidence with which the classifications are made were improved by using the small data set, despite that a significant portion of potential sequencing data from the sample is not obtained. For instance, as described in Example 9, the fraction of sequence reads originating from cancer-derived cfDNA fragments is enriched in sequencing data generated from cfDNA samples following size selection of cfDNA fragments in the 30-140 and 30-150 nucleotide ranges. Specifically, FIG. 19 shows that in vitro size selection increases tumor fraction in almost all of the 65 samples tested from subjects diagnosed with one of ten cancers and representing a distribution of all cancer stages. Further, Example 10 suggests the use of sequencing data generated from in vitro size selected cfDNA fragments improves the sensitivity of cancer detection using a classifier based on copy number variation of a predetermined number of genomic bins with low variability in a reference human genome. Specifically, it is reported in Table 6 that in vitro size selection of the cfDNA fragments improved the sensitivity of the classifier by about 20-30% at 95%, 98%, and 95% specificity In some aspects, the disclosed methods work in conjunction with cancer classification models. For example, a machine learning or deep learning model (e.g., a disease classifier) can be used to determine a disease state based on values of one or more features determined from size-selected sequence reads generated from cfDNA fragments. In various embodiments, the output of the machine learning or deep learning model is a predictive score or probability of a disease state (e.g., a predictive cancer score). Therefore, the machine learning or deep learning model generates a disease state classification based on the predictive score or probability.

Figure 7:
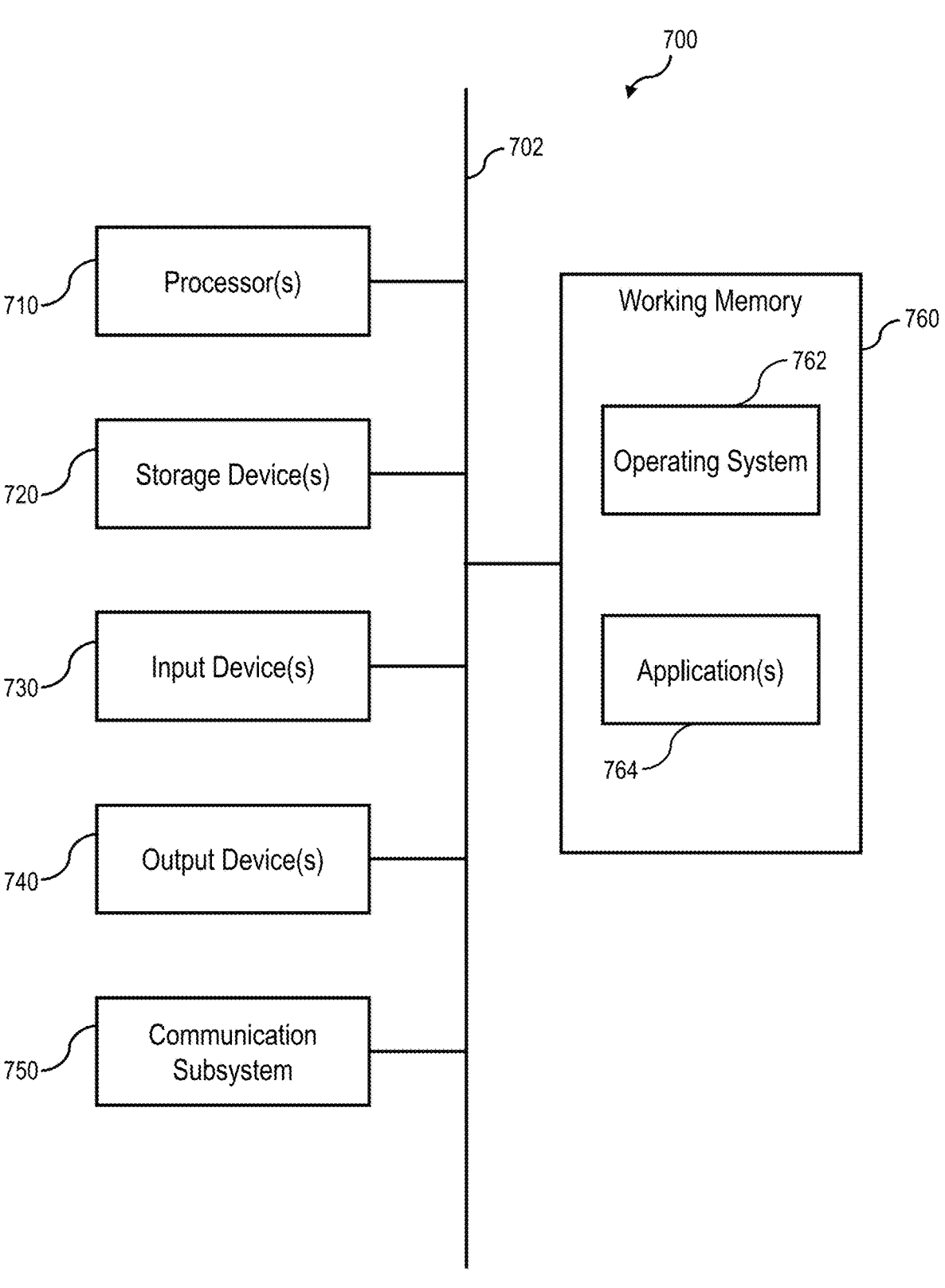
FIG. 7 depicts a diagram of an example system architecture for implementing the features and processes of FIGS. 1-6.

Details regarding the processes and features of the methods and systems, in accordance with various embodiments of the present disclosure, are disclosed with reference to FIGS. 13 and 14. In some embodiments, such processes and features of the system are carried out by the various modules described in example system 700, as illustrated in FIG. 7.

The embodiments described below relate to analyses performed using sequence reads of cell-free DNA fragments obtained from a biological sample, e.g., a blood sample. Generally, these embodiments are independent and, thus, not reliant upon any particular sequencing methodologies. However, in some embodiments, the methods described below include one or more steps of generating the sequence reads used for the analysis, and/or specify certain sequencing parameters that are advantageous for the particular type of analysis being performed. In some embodiments, the embodiments relating to size-selected sequence reads of cfDNA, as described below, are used in conjunction with any one of methods 200, 210, 300, 400, and 500 for training classifiers and/or classifying disease states, as described above.

FIG. 13 depicts a sample process for analyzing data based on information learned from in vitro size-selected cfDNA sequencing data with reduced dimensionality. Process 1300 illustrates how test data from a subject, whose status with respect to a medical condition (e.g., cancer) is unknown, can be used to compute a classification score and serve as a basis for diagnosing whether the subject is likely to have the condition.

At step 1302, a biological sample from a subject whose disease status may be unknown is obtained. In some embodiments, the sample includes a bodily fluid of the subject, e.g., blood, whole blood, plasma, serum, urine, cerebrospinal fluid, fecal, saliva, sweat, tears, pleural fluid, pericardial fluid, peritoneal fluid, other types of bodily fluids, or any combination thereof. In some embodiments, advantageously, methods for drawing a fluid sample (e.g., drawing a blood sample by syringe or finger prick) are less invasive than procedures for obtaining a tissue biopsy, which may require surgery. In some embodiments, the biological sample includes cfDNA.

In some embodiments, the blood sample is a whole blood sample, and prior to generating the plurality of sequence reads from the whole blood sample, white blood cells are removed from the whole blood sample. In some embodiments, the white blood cells are collected as a second type of sample, e.g., according to a buffy coat extraction method, from which additional sequencing data may or may not be obtained. Methods for buffy coat extraction of white blood cells are known in the art, for example, as described in U.S. Patent Application Serial No. U.S. Provisional Application No. 62/679,347, filed on Jun. 1, 2018, the content of which is incorporated herein by reference, in its entirety, for all purposes. In some embodiments, the method further includes obtaining a second plurality of sequence reads in electronic form of genomic DNA from the white blood cells removed from the whole blood sample. In some embodiments, the second plurality of sequence reads is used to identify allele variants arising from clonal hematopoiesis, as opposed to germline allele variants and/or allele variants arising from a cancer in the subject.

In some embodiments, the biological sample includes cell-free DNA molecules that are longer than a first threshold length, where the first threshold length is less than 160 nucleotides. However, in some embodiments, the sequence read data used in the classifier training, classifier validation, and disease classification methods described herein excludes sequence reads of cell-free DNA molecules longer than the first threshold length. Thus, the sequence read data used represents a reduced dimension space for the sequences of the cell-free DNA molecules in the biological sample. Analysis of this reduced set of sequence reads reduces the computational burden of processing the sequencing data, because fewer calculations are required, thereby reducing the time required and improving the efficiency of the computer system performing the analysis.

At step 1304, cfDNA, which will serve as the template for the sequencing reaction, is isolated from the sample. Methods for isolating cfDNA from biological samples are well known in the art. For a comparison of commercial cell-free DNA isolation kits see, for example, Sorber, L. et al., J Mol Diagn., 19(1):162-68 (2017). The content of which is incorporated herein by reference, in its entirety, for all purposes.

In some embodiments, a sequencing library is prepared at step 1304, e.g., prior to size-selection of the cfDNA fragments. During library preparation, unique molecular identifiers (UMIs) are added to the nucleic acid molecules (e.g., DNA molecules) through adapter ligation. In some embodiments, the UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. In some embodiments, e.g., when multiplex sequencing will be used to sequence cfDNA from a plurality of subjects in a single sequencing reaction, a patient-specific index is also added to the nucleic acid molecules. In some embodiments, the patient specific index is a short nucleic acid sequence (e.g., 3-20 nucleotides) that are added to ends of DNA fragments during library construction, that serve as a unique tag that can be used to identify sequence reads originating from a specific patient sample. During PCR amplification following adapter ligation, the UMIs are replicated along with the attached DNA fragment. This provides a way to identify sequence reads that came from the same original fragment in downstream analysis.

In some embodiments, library construction includes adding a nucleic acid fragment having a fixed length of x nucleotides to the cell-free DNA molecules of the subject, where the nucleic acid fragment includes an identifier unique to the subject. In some embodiments, nucleic acid fragments are added to both ends of the cell-free DNA molecules. Accordingly, as referred to herein, the fixed length of x nucleotides refers to the total length of all nucleic acid fragments added to either end of a cell-free DNA molecule. In some embodiments, the unique identifier encodes a unique predetermined value selected from the set $\{1, \ldots, 1024\}$, $\{1, \ldots, 4096\}$, $\{1, \ldots, 16,384\}$, $\{1, \ldots, 65,536\}$, $\{1, \ldots, 262,144\}$, $\{1, \ldots, 1,048,576\}$, $\{1, \ldots, 4,194,304\}$, $\{1, \ldots, 16,777,216\}$, $\{1, \ldots, 67,108,864\}$, $\{1, \ldots, 268,435,456\}$, $\{1, \ldots, 1,073,741,824\}$, or $\{1, \ldots, 4,294,967,296\}$. In some embodiments, the unique identifier is localized to a contiguous set of oligonucleotides within the added nucleic acid fragment. In some embodiments, the contiguous set of oligonucleotides is an N-mer, wherein N is an integer selected from the set $\{4, \ldots, 20\}$. In some embodiments, the nucleic acid fragment also includes one or more of a UMI, a primer hybridization sequence (e.g., for PCR amplification and/or sequencing), and complementary sequences used in clustering. In some embodiments, the fixed length x of the added nucleic acid fragment is from 100 nucleotides to 200 nucleotides. In other embodiments, the fixed length x of the added nucleic acid fragment is about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or more nucleotides.

In some embodiments, cfDNA sequencing libraries from a plurality of subjects, regardless of whether the libraries are prepared before or after size-selection, are pooled together prior to sequencing. Several advantages are achieved by pooling samples together for next generation sequencing. First, because of the high-throughput capacity of next generation sequencers, large amounts of template DNA are required for a single reaction. By pooling cfDNA sequencing libraries together, less cfDNA is required from each patient for the sequencing reaction. Second, because of the cost of a single sequencing reaction is essentially fixed, pooling cfDNA sequencing libraries, and sequencing them together, reduces the cost of sequencing per cfDNA library by a factor of the number of libraries pooled together.

At step 1306, cfDNA molecules are size selected, e.g., to remove molecules originating from cfDNA fragments that are longer than a threshold length (e.g., where the threshold length is less than 160 nucleotides). Methods for size selecting nucleic acid fragments are known in the art, e.g., agarose electrophoresis. In some embodiments, the size selection occurs prior to library preparation, and in other embodiments after library preparation. In some embodiments, when size selection occurs after library preparation, cfDNA fragment libraries from a plurality of subjects are pooled together prior to size selection. One advantage of pooling cfDNA libraries prior to size selection is that because the cost of size selection techniques is essentially fixed, size selecting a pool of cfDNA libraries in a single reaction (e.g., a single well of an agarose-based electrophoretic technique) reduces the cost of selection per sample.

Generally, the threshold length is set so as to increase the percentage of sequence reads that are generated for cfDNA fragments originating from cancer cells, as opposed to cfDNA fragments originating from somatic or hematopoietic cells. For instance, as can be seen by the shifting of cfDNA fragment length distribution as a function of tumor fraction in FIG. 15, cfDNA fragments originating from cancer cells have, on average, shorter lengths than cfDNA fragments originating from somatic cells or hematopoietic cells. Thus, the probability of a given fragment being derived from a cancer cell increases as the size of the fragment decreases. Accordingly, in some embodiments, the first threshold length is set to a value of less than 160 nucleotides. In some embodiments, the first threshold length is 150 nucleotides or less. In some embodiments, the first threshold length is 140 nucleotides or less. In some embodiments, the first threshold length is 130 nucleotides or less. In some embodiments, the first threshold length is 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, or fewer nucleotides. In one embodiment, the first threshold length is 140 nucleotides. In some embodiments, the first threshold length is between 130 nucleotides and 150 nucleotides. In some embodiments, the first threshold length is between 140 nucleotides and 150 nucleotides. In some embodiments, the first threshold length is between 130 nucleotides and 140 nucleotides.

As for cfDNA fragments derived from mono-nucleosome constructs, a similar size phenomenon was observed for cfDNA fragments derived from di-nucleosome fragments. That is, cell-free DNA fragments having lengths in the range of about 220 nucleotides to about 340 nucleotides are generally derived from di-nucleosome constructs. On average, cfDNA fragments from di-nucleosome constructs originating from cancer cells have shorter lengths than cfDNA fragments from di-nucleosome constructs originating from somatic or hematopoietic cells. Thus, in some embodiments, in order to provide more sequencing data from cfDNA fragments enriched in a cancerous origin, sequence reads generated from shorter cfDNA molecules derived from di-nucleosome constructs are also included in the plurality of sequence reads used to determine a cancer status of the subject.

Accordingly, in some embodiments, sequence reads of cell-free DNA fragments having a length falling between a second threshold length and a third threshold length are included in the filtered data set. In some embodiments, the second threshold length is from 240 nucleotides to 260 nucleotides and the third threshold length is from 290 nucleotides to 310 nucleotides. In some embodiments, the second threshold length is 250 nucleotides. In other embodiments, the second threshold length is 240, 241, 242, 243, 244, 245, 246, 247, 248, 249, 250, 251, 252, 253, 254, 255, 256, 257, 258, 259, or 260 nucleotides. In some embodiments, the third threshold length is 300 nucleotides (3028). In some embodiments, the third threshold length is 290, 291, 292, 293, 294, 295, 296, 297, 298, 299, 300, 301, 302, 303, 304, 305, 306, 307, 308, 309, or 310 nucleotides.

When size-selecting fragments from the pooled cfDNA sequencing library, the selected lengths are determined based on the sum of the desired range of lengths of the original cfDNA fragment (w) and the length of the adaptors (x, e.g., containing UMIs, primer sites, patient-specific indices, etc.), e.g., w+x.

At step 1308, sequence reads are generated from size-selected cfDNA libraries and/or pools. Sequencing data may be acquired by known means in the art. For example, next generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators. In some embodiments, where the sequencing reaction is a multiplex sequencing reaction of cfDNA from more than one sample and/or subject, the sequencing data is then de-multiplexed, to identify sequence reads from each sample and/or subject, based on identification of the unique UMI sequences.

In some embodiments, the average coverage rate of the sequence reads across a reference genome for the species of the subject is at least 3×. In some embodiments, the average coverage rate is at least 5×. In some embodiments, the average coverage rate is at least 10×. In some embodiments, the average coverage rate is between about 0.1× and about 35×, or between about 2× and about 20×, e.g., about 0.1×, 0.5×, 1×, 2', 3', 4×, 5×, 6×, 7×, 8×, 9×, 10×, 11×, 12×, 13×, 14×, 15×, 16×, 17×, 18×, 19×, 20×, 25×, 30×, 35×, etc. In some embodiments, where cfDNA fragments are size-selected prior to sequencing, the sequence coverage of the sequencing reaction is on the lower end of this range. For instance, it was found that size-selection of sub-sampled cfDNA data at 5× coverage resulting in an average sequence coverage of 0.09× still performed about as well as the non-size selected data at 5× coverage. Thus, if the cfDNA is size-selected prior to sequencing, much lower sequence coverage would be expected to provide the necessary diagnostic sensitivity at high specificity. Accordingly, in some embodiments, where the cfDNA fragments are size-selected prior to sequencing, the average coverage rate is between about 0.1× and about 5×, or between about 0.5× and about 3×, e.g., about or at least 0.1×, 0.2×, 0.3×, 0.4×, 0.5×, 0.6×, 0.7×, 0.8×, 0.9×, 1×, 1.25×, 1.5×, 1.75×, 2×, 2.5×, 3×, 3.5×, 4×, 4.5×, 5×, 6×, 7×, 8×, 9×, or 10×.

Steps 1310, 1312, and 1314 are then performed as described above with reference to steps 520, 530, and 540 of process 500, respectively. In fact, in some embodiments, the sequencing data generated at step 1308 is used as an input for any of processes 200, 210, 300, 400, or 500, as described above.

In some embodiments, the diagnosis provided in step 1314 is determined with a first degree of confidence, and the first degree of confidence is greater than a second degree of confidence that would have been provided had the classification score in step 1312 been computing using sequencing data that had not been size selected. In some embodiments, while the determination of disease status (e.g., cancer class) associated with a positive diagnosis for the disease (e.g., cancer) in the subject is made with a greater confidence using the size-selected sequence reads, determinations of a disease status associated with a diagnosis that the subject does not have the disease are not made with a greater confidence than if a set of non-size-selected sequence reads were used. That is, in some embodiments, the methods provided herein result in disease classification that is made with greater confidence when the subject has the disease, but with a similar or lower confidence when the subject does not have the disease. This, of course, does not require that the classification with a full set of sequence reads from a biological sample is actually performed, or that the second confidence is actually calculated. In some embodiments, however, the second classification and/or confidence is determined.

FIG. 14 depicts a sample process for analyzing data based on information learned from in silico size-selected cfDNA sequencing data with reduced dimensionality. Process 1400 illustrates how test data from a subject, whose status with respect to a medical condition (e.g., cancer) is unknown, can be used to compute a classification score and serve as a basis for diagnosing whether the subject is likely to have the condition.

At step 1402, cfDNA sequencing data from a subject whose disease status may be unknown is obtained. In some embodiments, the cfDNA was isolated from a sample including a bodily fluid of the subject, e.g., blood, whole blood, plasma, serum, urine, cerebrospinal fluid, fecal, saliva, sweat, tears, pleural fluid, pericardial fluid, peritoneal fluid, other types of bodily fluids, or any combination thereof. In some embodiments, advantageously, methods for drawing a fluid sample (e.g., drawing a blood sample by syringe or finger prick) are less invasive than procedures for obtaining a tissue biopsy, which may require surgery, e.g., as described with reference to step 1302 in process 1300. In some embodiments, the sequencing is performed after pooling cfDNA libraries, e.g., prepared as described above with reference to step 1304 in process 1300. In some embodiments, the sequencing is performed as described above with reference to step 1308 in process 1300.

In some embodiments, the average coverage rate of the sequence reads across a reference genome for the species of the subject is at least 3×. In some embodiments, the average coverage rate is at least 5×. In some embodiments, the average coverage rate is at least 10×. In some embodiments, the average coverage rate is between about 0.1× and about 35×, or between about 2× and about 20×, e.g., about 0.1×, 0.5×, 1×, 2×, 3×, 4×, 5×, 6×, 7×, 8×, 9×, 10×, 11×, 12×, 13×, 14×, 15×, 16×, 17×, 18×, 19×, 20×, 25×, 30×, 35×, etc. In some embodiments, where cfDNA fragments are not size-selected prior to sequencing, but rather the resulting sequence reads are filtered, the sequence coverage of the sequencing reaction is not on the low end of this range. For instance, it was found that in silico filtering of a sub-sampled CCGA data set having 5× sequence coverage resulted in a filtered data set having only 0.09× sequence coverage. Accordingly, in some embodiments, where the cfDNA sequence reads are size-selected after sequencing, the average coverage rate is between about 2× and about 35×, or between about 3× and about 10×, e.g., about or at least 2×, 3×, 4×, 5×, 6×, 7×, 8×, 9×, 10×, 11×, 12×, 13×, 14×, 15×, 16×, 17×, 18×, 19×, 20×, 25×, 30×, or 35×.

At step 1404, the sequencing data is filtered to select sequence reads from cfDNA fragments with lengths falling within a desired range, e.g., by applying a length filter to the precursor sequence reads obtained in step 1402. In some embodiments, this includes filtering the sequence reads to exclude sequence reads from cfDNA molecules that are longer than a threshold length, e.g., where the threshold length is less than 160 nucleotides. In some embodiments, this is accomplished by determining the length of a cfDNA corresponding to one or more sequence read, e.g., based on the positions of the beginning and ending nucleotide bases in the reference genome, and selecting only those sequence reads corresponding to cfDNA fragments with lengths falling within a desired range of lengths, such that the selected subset of sequence reads is enriched for sequence reads corresponding to cfDNA fragments derived from a cancer cell.

Generally, as described above with reference to step 1306 of process 1300, the threshold length is set so as to increase the percentage of sequence reads that are generated for cfDNA fragments originating from cancer cells, as opposed to cfDNA fragments originating from somatic or hematopoietic cells. For instance, as can be seen by the shifting of cfDNA fragment length distribution as a function of tumor fraction in FIG. 15, cfDNA fragments originating from cancer cells have, on average, shorter lengths than cfDNA fragments originating from somatic cells or hematopoietic cells. Thus, the probability of a given fragment being derived from a cancer cell increases as the size of the fragment decreases. Accordingly, in some embodiments, the first threshold length is set to a value of less than 160 nucleotides. In some embodiments, the first threshold length is 150 nucleotides or less. In some embodiments, the first threshold length is 140 nucleotides or less. In some embodiments, the first threshold length is 130 nucleotides or less. In some embodiments, the first threshold length is 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, or fewer nucleotides. In one embodiment, the first threshold length is 140 nucleotides. In some embodiments, the first threshold length is between 130 nucleotides and 150 nucleotides. In some embodiments, the first threshold length is between 140 nucleotides and 150 nucleotides. In some embodiments, the first threshold length is between 130 nucleotides and 140 nucleotides.

As for cfDNA fragments derived from mono-nucleosome constructs, a similar size phenomenon was observed for cfDNA fragments derived from di-nucleosome fragments. That is, cell-free DNA fragments having lengths in the range of about 220 nucleotides to about 340 nucleotides are generally derived from di-nucleosome constructs. On average, cfDNA fragments from di-nucleosome constructs originating from cancer cells have shorter lengths than cfDNA fragments from di-nucleosome constructs originating from somatic or hematopoietic cells. Thus, in some embodiments, in order to provide more sequencing data from cfDNA fragments enriched in a cancerous origin, sequence reads generated from shorter cfDNA molecules derived from di-nucleosome constructs are also included in the plurality of sequence reads used to determine a cancer status of the subject.

Accordingly, in some embodiments, sequence reads of cell-free DNA fragments having a length falling between a second threshold length and a third threshold length are included in the filtered data set. In some embodiments, the second threshold length is from 240 nucleotides to 260 nucleotides and the third threshold length is from 290 nucleotides to 310 nucleotides. In some embodiments, the second threshold length is 250 nucleotides. In other embodiments, the second threshold length is 240, 241, 242, 243, 244, 245, 246, 247, 248, 249, 250, 251, 252, 253, 254, 255, 256, 257, 258, 259, or 260 nucleotides. In some embodiments, the third threshold length is 300 nucleotides (3028). In some embodiments, the third threshold length is 290, 291, 292, 293, 294, 295, 296, 297, 298, 299, 300, 301, 302, 303, 304, 305, 306, 307, 308, 309, or 310 nucleotides.

Steps 1410, 1412, and 1414 are then performed as described above with reference to steps 520, 530, and 540 of process 500, respectively. In fact, in some embodiments, the filtered sequencing data generated at step 1404 is used as an input for any of processes 200, 210, 300, 400, or 500, as described above.

In some embodiments, the diagnosis provided in step 1314 is determined with a first degree of confidence, and the first degree of confidence is greater than a second degree of confidence that would have been provided had the classification score in step 1312 been computing using sequencing data that had not been size selected. In some embodiments, while the determination of disease status (e.g., cancer class) associated with a positive diagnosis for the disease (e.g., cancer) in the subject is made with a greater confidence using the size-selected sequence reads, determinations of a disease status associated with a diagnosis that the subject does not have the disease are not made with a greater confidence than if a set of non-size-selected sequence reads were used. That is, in some embodiments, the methods provided herein result in disease classification that is made with greater confidence when the subject has the disease, but with a similar or lower confidence when the subject does not have the disease. This, of course, does not require that the classification with a full set of sequence reads from a biological sample is actually performed, or that the second confidence is actually calculated. In some embodiments, however, the second classification and/or confidence is determined.

Example System Architecture

FIG. 7 depicts a diagram of an example system architecture for implementing the features and processes of FIGS. 1-6.

In one aspect, some embodiments can employ a computer system (such as the computer system 700) to perform methods in accordance with various embodiments of the invention. An exemplary embodiment of computer system 700, includes a bus 702, one or more processors 712, one or more storage devices 714, at least an input device 716, at least an output device 718, a communication subsystem 720, working memory 730 which includes an operating system 732, device drivers, executable libraries, and/or other code, such as one or more application(s) 734.

According to a set of embodiments, some or all of the procedures of such methods are performed by the computer system 700 in response to processor 712 executing one or more sequences of one or more instructions (which might be incorporated into operating system 732 and/or other code, such as an application program 734) contained in working memory 730. Such instructions can be read into the working memory 730 from another computer-readable medium, such as one or more of storage device(s) 714. Merely by way of example, execution of the sequences of instructions contained in working memory 730 might cause processor(s) 712 to perform one or more procedures of the methods described herein. Additionally, or alternatively, portions of the methods described herein can be executed through specialized hardware. Merely by way of example, a portion of one or more procedures described with respect to the method(s) discussed above, such as method 200, method 210, method 300, method 310, method 400, method 500, method 600, and any variations of those illustrated in FIGS. 2-6, might be implemented by processor 712. In some instances, processor 712 can used in connection with system 100 or system 110. In some examples, application program 734 can be an example of an application performing the iterative real-time learning method depicted in FIGS. 2-6.

In some embodiments, computer system 700 can further include (and/or be in communication with) one or more non-transitory storage devices 714, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices can be configured to implement any appropriate data stores, including without limitation, various file systems, database structures, and/or the like. In some embodiments, storage device 714 can be an example of database 130.

In some embodiments, computer system 700 can further include one or more input devices 716, which can comprise, without limitation, any input device that allows a computer device to receive information from a user, from another computer device, from the environment of the computer device, or from a functional component communicably connected with the computer device.

In some embodiments, computer system 700 can further include one or more input output devices 718, which can comprise, without limitation, any output device that can receive information from a computer device and communicate such information to a user, to another computer device, to the environment of the computer device, or to a functional component communicably connected with the computer device. Examples of input devices include but are not limited to a display, a speaker, a printer, a light, a sensor device, and etc. A sensor device can receive and exhibit data in forms that can result in sensory perception by a user. Such forms include but are not limited to heat, light, touch, pressure, motion, and etc.

It would be understood that any applicable input/output devices or components, such as those disclosed in connection with system 100 or 110, can be applied to input device 716 and output device 718.

In some embodiments, computer system 700 might also include a communications subsystem 720, which can include without limitation a modem, an Ethernet connection, a network card (wireless or wired), an infrared communication device, a wireless communication device, and/or a chipset (such as a Bluetooth™ device, an 802.11 device, a WiFi device, a WiMax device, cellular communication facilities, etc.), a near-field communication (NFC), a Zigbee communication, a radio frequency (RF) or radio-frequency identification (RFID) communication, a PLC protocol, a 3G/4G/5G/LTE based communication, and/or the like. Communications subsystem 720 can include one or more input and/or output communication interfaces to permit data to be exchanged with a network, other computer systems, and/or any other electrical devices/peripherals. In many embodiments, computer system 700 will further comprise a working memory 730, which can include a RAM or ROM device, as described above.

In some embodiments, computer system 700 also can comprise software elements, shown as being currently located within the working memory 730, including an operating system 732, device drivers, executable libraries, and/or other code, such as one or more application(s) 734, which can comprise computer programs provided by various embodiments, and/or can be designed to implement methods, and/or configure systems, provided by other embodiments, as described herein. Merely by way of example, a portion of one or more procedures described with respect to the method(s) discussed above, such as the methods described in relation to FIGS. 2-6, can be implemented as code and/or instructions executable by a computer (and/or a processing unit within a computer); in an aspect, then, such code and/or instructions can be used to configure. In some embodiment, a general purpose computer (or other device) can be adapted to perform one or more operations in accordance with the described methods. In some instances, working memory can 730 can be an example of the memory of any device used in connection with system 100 or 110.

A set of these instructions and/or code might be stored on a non-transitory computer-readable storage medium, such as storage device(s) 714 described above. In some cases, the storage medium might be incorporated within a computer system, such as computer system 600. In other embodiments, the storage medium might be separate from a computer system (e.g., a removable medium, such as an optical disc), and/or provided in an installation package, such that the storage medium can be used to program, configure, and/or adapt a general purpose computer with the instructions/code stored thereon. These instructions might take the form of executable code, which is executable by computer system 700 and/or might take the form of source and/or installable code, which, upon compilation and/or installation on the computer system 700 (e.g., using any of a variety of generally available compilers, installation programs, compression/decompression utilities, etc.), then takes the form of executable code. In some instances, storage device(s) 730 can be an example of the memory of device 102, 220 or 240.

It will be apparent to those skilled in the art that substantial variations can be made in accordance with specific requirements. For example, customized hardware might also be used, and/or particular elements might be implemented in hardware, software (including portable software, such as applets, etc.), or both. Further, connection to other computing devices such as network input/output devices can be employed.

The terms "machine-readable medium" and "computer-readable medium," as used herein, refer to any medium that participates in providing data that causes a machine to operate in a specific fashion. In an embodiment implemented using computer system 700, various computer-readable media might be involved in providing instructions/code to processor(s) 712 for execution and/or might be used to store and/or carry such instructions/code. In many implementations, a computer-readable medium is a physical and/or tangible storage medium. Such a medium can take the form of a non-volatile media or volatile media. Non-volatile media include, for example, optical and/or magnetic disks, such as storage device(s) 714. Volatile media include, without limitation, dynamic memory, such as working memory 730.

Common forms of physical and/or tangible computer-readable media include, for example, a floppy disk, a flexible disk, hard disk, magnetic tape, flash disk, flash drive, or any other magnetic medium, a CD-ROM, any other optical medium, any other physical medium with patterns of holes, a RAM, a PROM, EPROM, a FLASH-EPROM, any other memory chip or cartridge, or any other medium from which a computer can read instructions and/or code.

Various forms of computer-readable media can be involved in carrying one or more sequences of one or more instructions to processor(s) 712 for execution. Merely by way of example, the instructions can initially be carried on a magnetic disk and/or optical disc of a remote computer. A remote computer might load the instructions into its dynamic memory and send the instructions as signals over a transmission medium to be received and/or executed by computer system 700.

Communications subsystem 720 (and/or components thereof) generally will receive signals, and bus 702 then might carry the signals (and/or the data, instructions, etc. that are carried by the signals) to working memory 730, from which processor(s) 712 retrieves and executes the instructions. The instructions received by working memory 730 can optionally be stored on non-transitory storage device 714 either before or after execution by processor(s) 712.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Comparison of B-Score and Z-Score

FIG. 8 includes a table comparing the current method (b score) with a previous known segmentation method (z-score). The data showed that overall the predictive power of b score is consistently higher than that of the z-scores across all stages of breast cancer samples.

FIG. 9 provides a more detailed example comparison classification scores (z score: top; b score: bottom) of individual subjects with breast cancer. Again, using b scores, cancer status of more subjects were correctly predicted cross all different stages of invasive breast cancer.

Example 2

Different Types of Cancer

FIG. 10 shows the improved predictive power of using the b-score method can be observed for all types of cancer (top). The predictive power for early-stage cancer is improved and for late-stage cancer is especially good (bottom).

Figure 11B:
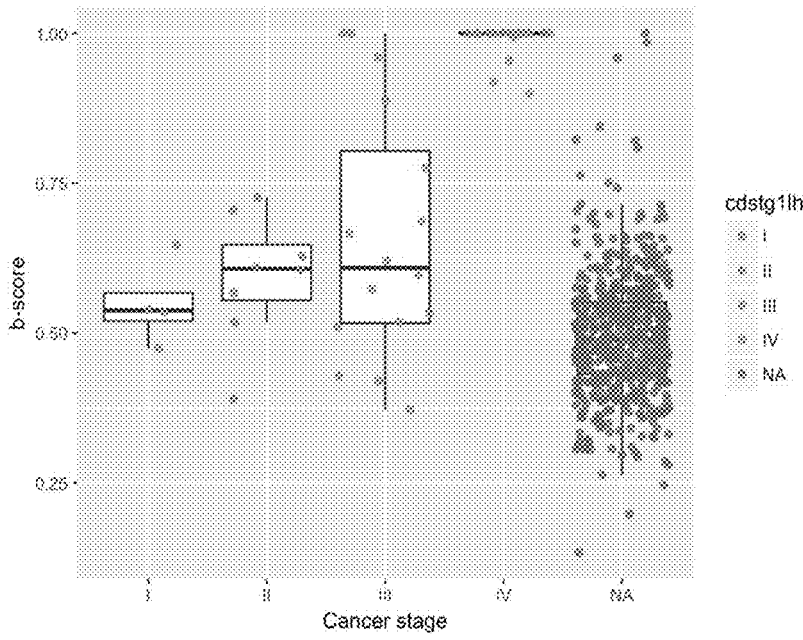
FIG. 11B depicts exemplary results of the current method.

FIG. 11A shows that improvement can be observed for subjects with lung cancer (top) and prostate cancer (bottom). FIG. 11B shows that improvement can be observed for subjects with colorectal cancers.

Example 3

Development of Plasma Cell-Free DNA (cfDNA) Assays for Early Cancer Detection: First Insights from the Circulating Cell-Free Genome Atlas Study (CCGA)

The data used in the analyses presented in Examples 4-7 below was collected in conjunction with Memorial Sloan Kettering Cancer Center (MSKCC), as part of the CCGA clinical study. CCGA [NCT02889978] is the largest study of cfDNA-based early cancer detection; the first CCGA learnings from multiple cfDNA assays are reported here. This prospective, multi-center, observational study has enrolled 9,977 of 15,000 demographically-balanced participants at 141 sites. Blood was collected from participants with newly diagnosed therapy-naive cancer (C, case) and participants without a diagnosis of cancer (noncancer [NC], control) as defined at enrollment. This preplanned substudy included 878 cases, 580 controls, and 169 assay controls (n=1627) across 20 tumor types and all clinical stages. All samples were analyzed by: 1) Paired cfDNA and white blood cell (WBC)-targeted sequencing (60,000×, 507 gene panel); a joint caller removed WBC-derived somatic variants and residual technical noise; 2) Paired cfDNA and WBC whole-genome sequencing (WGS; 35×); a novel machine learning algorithm generated cancer-related signal scores; joint analysis identified shared events; and 3) cfDNA whole-genome bisulfite sequencing (WGBS; 34×); normalized scores were generated using abnormally methylated fragments. In the targeted assay, non-tumor WBC-matched cfDNA somatic variants (SNVs/indels) accounted for 76% of all variants in NC and 65% in C. Consistent with somatic mosaicism (i.e., clonal hematopoiesis), WBC-matched variants increased with age; several were non-canonical loss-of-function mutations not previously reported. After WBC variant removal, canonical driver somatic variants were highly specific to C (e.g., in EGFR and PIK3CA, 0 NC had variants vs 11 and 30, respectively, of C). Similarly, of 8 NC with somatic copy number alterations (SCNAs) detected with WGS, 4 were derived from WBCs. WGBS data revealed informative hyper- and hypo-fragment level CpGs (1:2 ratio); a subset was used to calculate methylation scores. A consistent "cancer-like" signal was observed in <1% of NC participants across all assays (representing potential undiagnosed cancers). An increasing trend was observed in NC vs stages I-III vs stage IV (nonsyn. SNVs/indels per Mb [Mean±SD] NC: 1.01±0.86, stages I-III: 2.43±3.98; stage IV: 6.45±6.79; WGS score NC: 0.00±0.08, I-III: 0.27±0.98; IV: 1.95±2.33; methylation score NC: 0±0.50; I-III: 1.02±1.77; IV: 3.94±1.70). These data demonstrate the feasibility of achieving >99% specificity for invasive cancer, and support the promise of cfDNA assay for early cancer detection. Additional data will be presented on detected plasma:tissue variant concordance and on multi-assay modeling.

The cancer types included in the CCGA study included invasive breast cancer, lung cancer, colorectal cancer, DCIS, ovarian cancer, uterine cancer, melanoma, renal cancer, pancreatic cancer, thyroid cancer, gastric cancer, hepatobiliary cancer, esophageal cancer, prostate cancer, lymphoma, leukemia, multiple myeloma, head and neck cancer, and bladder cancer.

Example 4

Distribution of Cell-Free DNA Fragments in Cancer Patients

Figure 15:
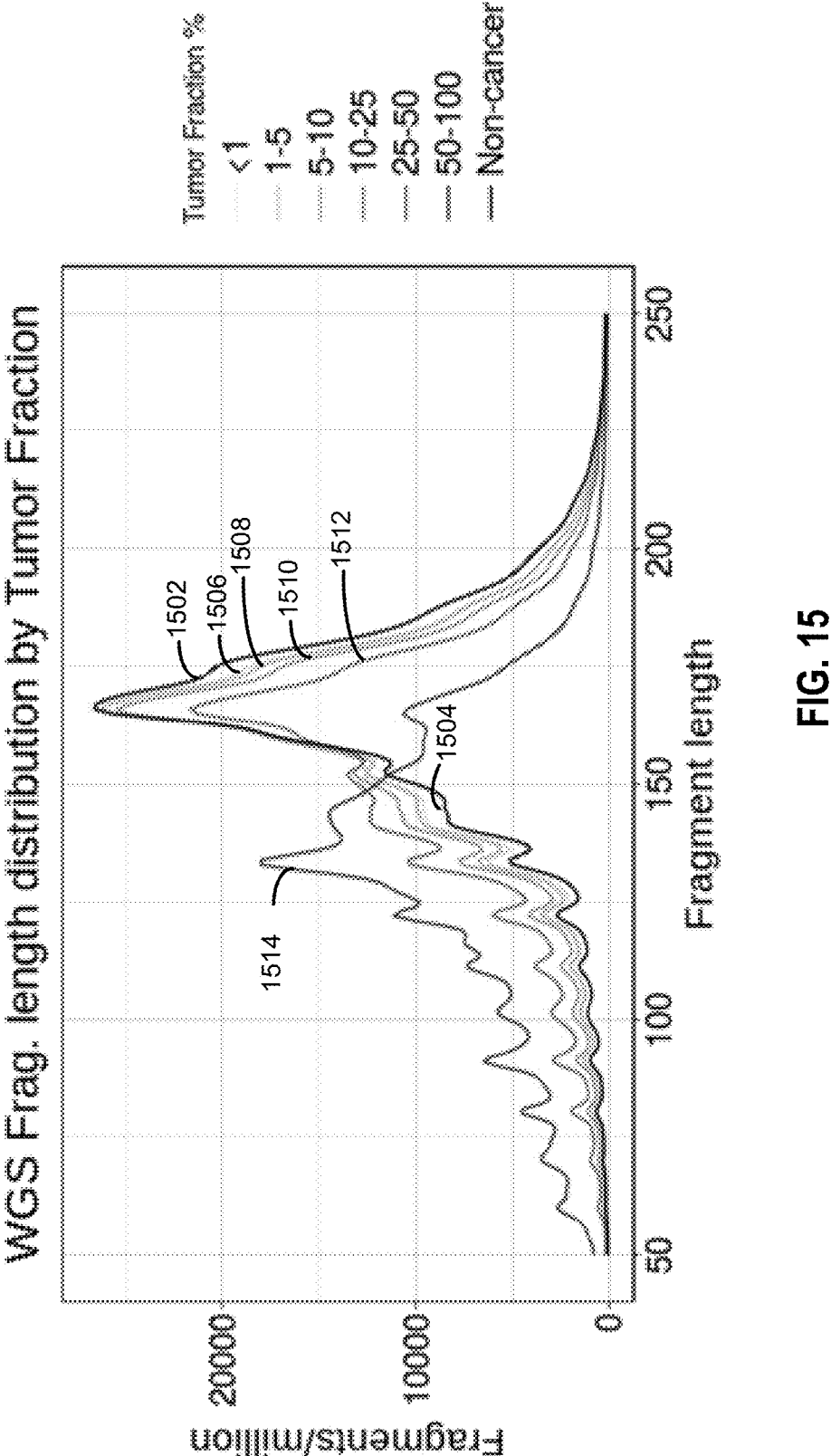
FIG. 15 illustrates the average distributions of cell-free DNA fragments lengths from subjects plotted as a function of the tumor fraction of the subject, as described in Example 4. Data for the 50-100% tumor fraction cohort was derived from a single sample from a subject with metastatic cancer.

The distribution of cell-free DNA fragment lengths, as determined by whole genome sequencing (WGS) was investigated in cell-free DNA samples from subjects having varying tumor fractions. Briefly, WGS results from 747 healthy individuals and 1001 confirmed cancer patients from the CCGA study, as described above, were plotted as a function of the tumor fraction of the subject. FIG. 15 shows average distributions of cell-free DNA fragment length from 747 healthy subjects (1502), 708 cancer patients with tumor fractions of less than 1% (1504), 136 cancer patients with tumor fractions between 1-5% (1506), 61 cancer patients with tumor fractions between 5-10% (1508), 73 cancer patients with tumor fractions between 10-25% (1510), 22 cancer patients with tumor fractions between 25-50% (1512), and 1 cancer patient with a tumor fraction between 50-100% (1514). As can be seen in FIG. 15, the distribution of lengths of cell-free DNA fragments is shifted shorter as a function of the tumor fraction of the patient. That is, the tumor fraction of the subject correlates with the magnitude of the cell-free DNA fragment length shift. This represents a difference in biology between cancer and healthy cells, in which cell-free DNA originating from cancer cells is shorter in length than cell-free DNA originating from healthy cells.

Example 5

Genomic Sequence Coverage Following In Silico Size-Selection

Figure 16A:
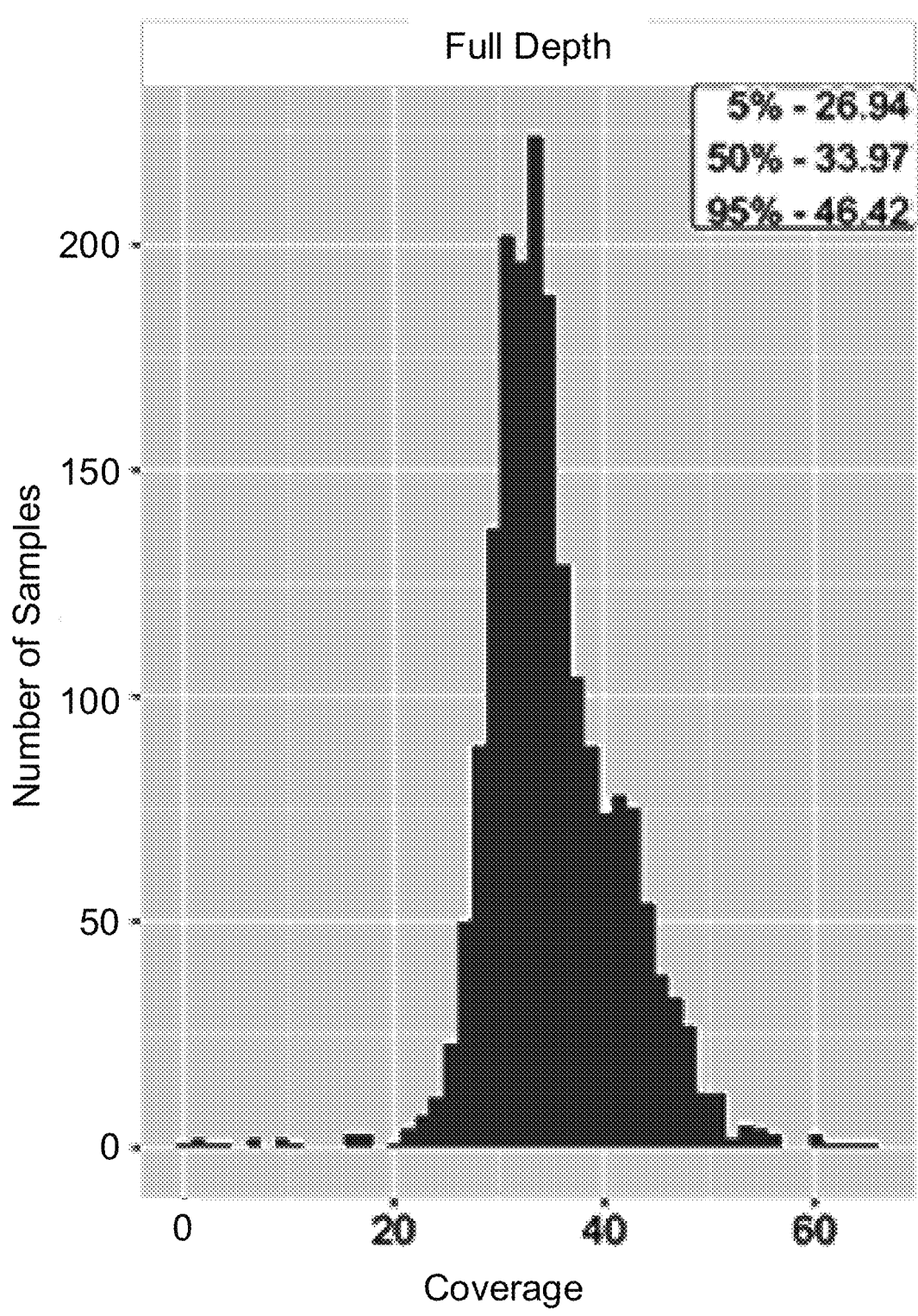
FIGS. 16A, 16B, and 16C illustrate histograms of sequencing coverage obtained from whole genome sequencing of cfDNA samples when unfiltered (FIG. 16A), filtered in silico to only include sequences from cfDNA fragments having a size of from 90 to 150 nucleotides (FIG. 16B), and filtered in silico to only include sequences from cfDNA fragments having a size of 100 nucleotides or less (FIG. 16C), as described in Example 5.
Figure 16B:
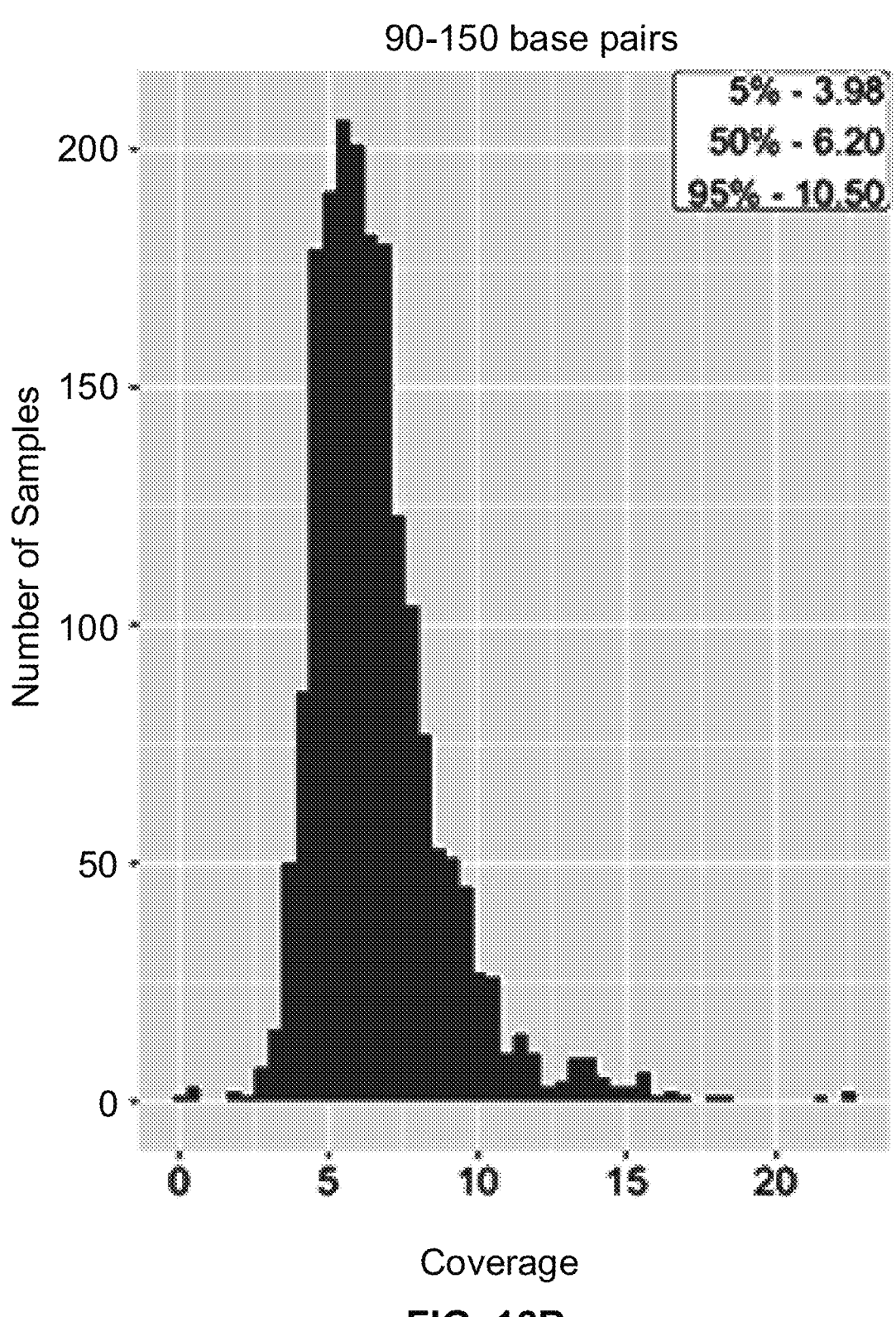
Figure 16C:
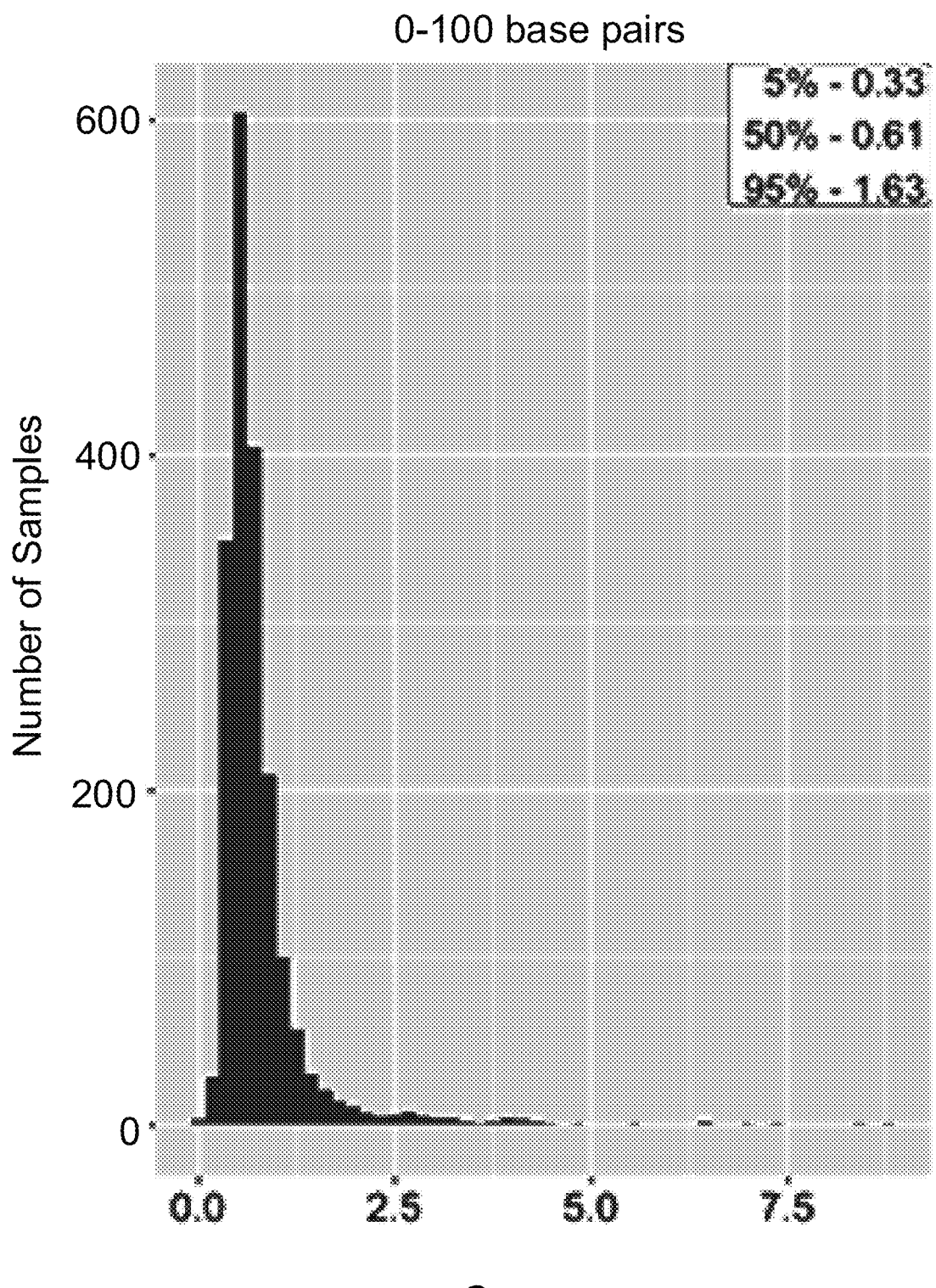

The sequence coverage obtained after size-selecting data generated by whole genome sequencing (WGS) of cell-free DNA samples was investigated. Briefly, sequencing data obtained from the CCGA study described above was filtered in silico to include only sequences obtained from cfDNA fragments having a size of from 90 to 150 nucleotides (FIG. 16B) or only sequences generated from cfDNA fragments having a size of 100 nucleotides or less (FIG. 16C). The average sequence coverage was then calculated for the unfiltered data set, the data set filtered to include only sequences from cfDNA fragments of 90 to 150 nucleotides, and the data set filtered to include only sequences from cfDNA fragments of 100 nucleotides or less. As shown by the histograms illustrated in FIG. 16, the unfiltered CCGA data sets had a median sequence coverage of about 34× (FIG. 16A), the data sets filtered to sequences from cfDNA fragments of 90 to 150 nucleotides had a median sequence coverage of about 6× (FIG. 16B), and the data sets filtered to sequences from cfDNA fragments of 100 nucleotides or less had a median sequence coverage of about 0.6× (FIG. 16C). Fifth and ninety-fifth percentiles for each distribution are also shown in FIG. 16.

Example 6

Cancer Classification Following In Silico Size-Selection

Although selection of sequence reads generated from smaller cfDNA fragments (e.g., less than 150 nucleotides) should enrich for cancer-derived fragments in samples from cancer patients, this selection will result in a net loss of information about the cancer because some of the larger cfDNA fragments that are removed will be derived from the cancer. Thus, although cancer-derived fragments are enriched relative to non-cancer derived fragments in the size-selected data set, it was theorized that the overall diagnostic power of the data set would be reduced relative to the full data set. In order to test whether this was the case, the data sets filtered as described in Example 5 were input into a cancer classifier trained against copy number variation across a plurality of predetermined genomic bins, each representing a predefined portion of the human genome, as described herein.

Briefly, CCGA data sets of sequence reads from cancer patients and healthy subjects, excluding uterine, thyroid, prostate, melanoma, renal, and HR+ stage I/II breast cancers, were filtered as described in Example 5, to either select sequence reads from cfDNA having lengths of 90-150 nucleotides or sequence reads from cfDNA having lengths of 100 nucleotides or less. The filtered data was then normalized within the filtered data sets, and the normalized data for each filtered sample input into a logistic regression classifier trained against features of low-variance genomic bin counts. To control for the difference in sequence coverage between the filtered and unfiltered data sets, as reported in Example 5, control data sets were generated by size-independently selecting sequence reads at random from the unfiltered data set to achieve the same sequence coverage as the corresponding size-selected data set, e.g., having a median sequence coverage of about 6.2× for the 150-90 nucleotide control data sets and about 0.6× median sequence coverage for the 0-100 nucleotide control data set.

Classifications were then generated for each unfiltered, control, and size-selected data sets at 95% specificity and 99% specificity. Fifty rounds of classification were performed using 90-10 splits of CCGA training data, balanced for cancer and non-cancer data sets, using a cancer classifier trained against copy number variation across a plurality of predetermined genomic bins, each representing a predefined portion of the human genome having low variability across the genomes of healthy subjects, as described above. The sensitivity of each group of classifications was then generated based on the known status of each subject in the CCGA. The results of these classifications are illustrated in FIG. 17A, with the results from the full-depth (unfiltered) data sets illustrated on the left of each grouping (e.g., 1702), the results from the sequence-coverage control data sets illustrated in the middle of each grouping (e.g., 1704), and the results from the size-selected data sets illustrated on the right of each grouping (e.g., 1706).

Figure 17A:
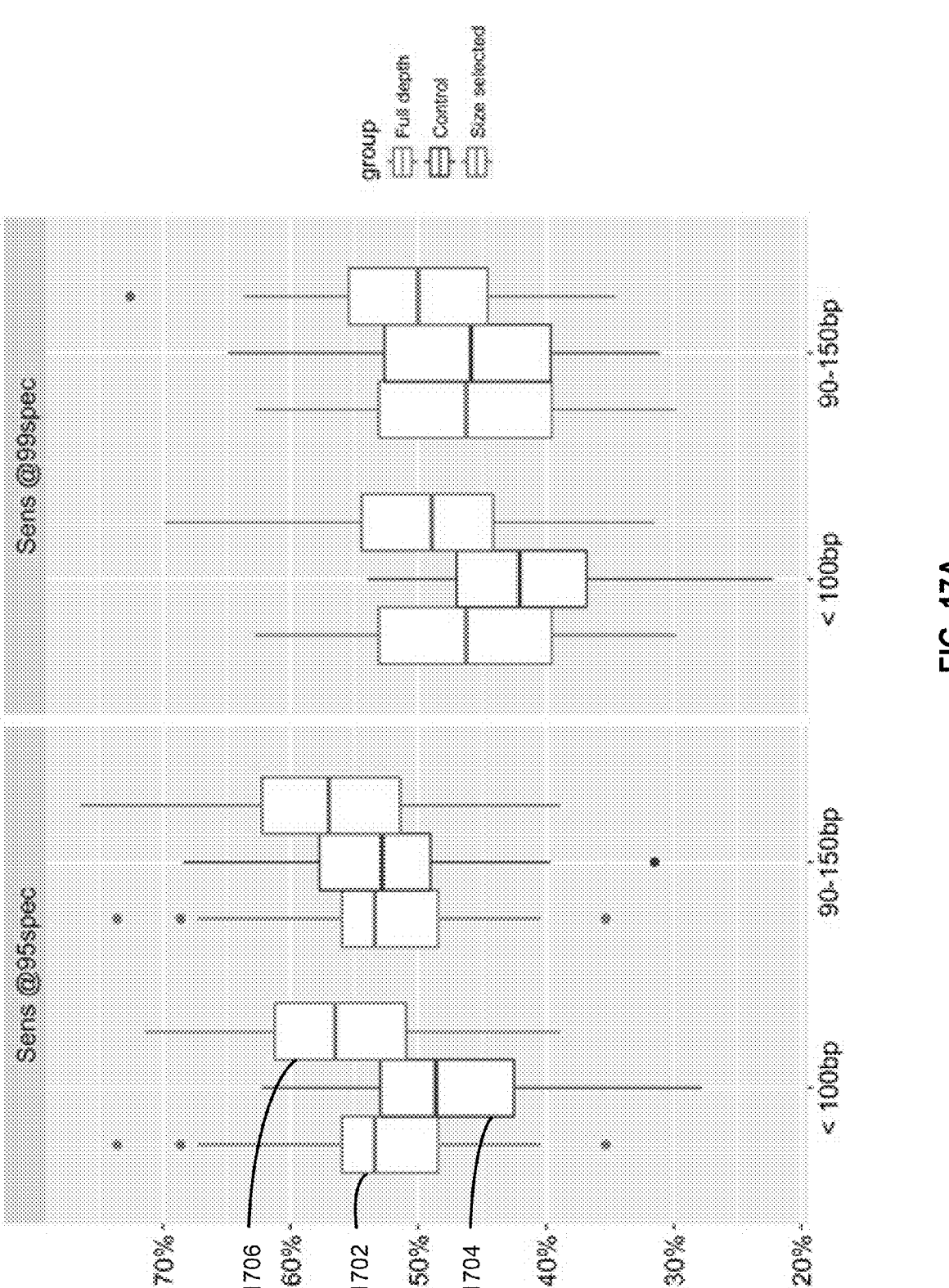
FIG. 17A illustrates box plots of the specificity of cancer classification using full (unfiltered) CCGA WGS data sets, size-selected (filtered) CCGAWGS data sets, and control data sets with randomly selected sequence reads from the full (unfiltered) CCG AWGS data sets to match the sequence coverage of the seize-selected (filtered) CCG AWGS data sets, as described in Example 6.

As compared to the control data sets having the same sequence coverage, the size-selected data sets consistently performed better (compare the right plot of each grouping to the middle plot of each grouping in FIG. 17A). This is consistent with the fact that the size-selected data sets should contain more sequence reads from cancer-derived cfDNA fragments than the control data set. Remarkably, however, both types of size-selected data sets also performed better than the corresponding full data sets, despite having 5- to 50-fold less sequence coverage and containing fewer sequence reads from cancer-derived cfDNA fragments than the control data set (compare the right plot of each grouping to the left plot of each grouping in FIG. 17A).

Example 7

Cancer Classification Following In Silico Size-Selection

Figure 17B:
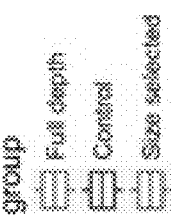
FIG. 17B illustrates box plots of the specificity of cancer classification using full (unfiltered) CCGAWGS data sets, size-selected (filtered) CCGAWGS data sets, and control data sets with randomly selected sequence reads from the full (unfiltered) CCG AWGS data sets to match the sequence coverage of the seize-selected (filtered) CCG AWGS data sets, as described in Example 7.

The analysis outlined in Example 5 was repeated for in silico selection of sequence reads corresponding to cfDNA of 100 nucleotides or less in all cancer types in the CCGA study, e.g., without excluding uterine, thyroid, prostate, melanoma, renal, and HR+ stage VII breast cancers. Again, as a control, the full data sets where sub-sampled to sequence coverage matching the sequence coverage of the size-selected data sets. Fifty rounds of classification were performed using 90-10 splits of CCGA training data, balanced for cancer and non-cancer data sets. As shown in FIG. 17B, in silico size selection across all cancer types provided improvements in classification sensitivity at both 95% specificity and 99% specificity, against both the full data sets and the sequence coverage-matched control data sets. The classification statistics for this analysis are presented in Table 1.

TABLE 1

| Statistics for cancer classification following in silico filtering of CCGA data sets to sequence reads representing cfDNA fragments with lengths of 100 nucleotides or less. | | | | |
|---|---|---|---|---|
| Size select vs. . . . | Subsample | Full depth | Subsample | Size select vs. . . . |
| Sens@spec of . . . | 95% | | 99% | |
| p-value | 2e–6 | 0.13 | 3e–8 | 4e–3 |
| mean change | 0.051 | 0.013 | 0.052 | 0.023 |
| (2.5%, 97.5% CI) | (0.032, 0.069) | (–0.004, 0.031) | (0.036, 0.067) | (0.007, 0.038) |

Figure 17C:
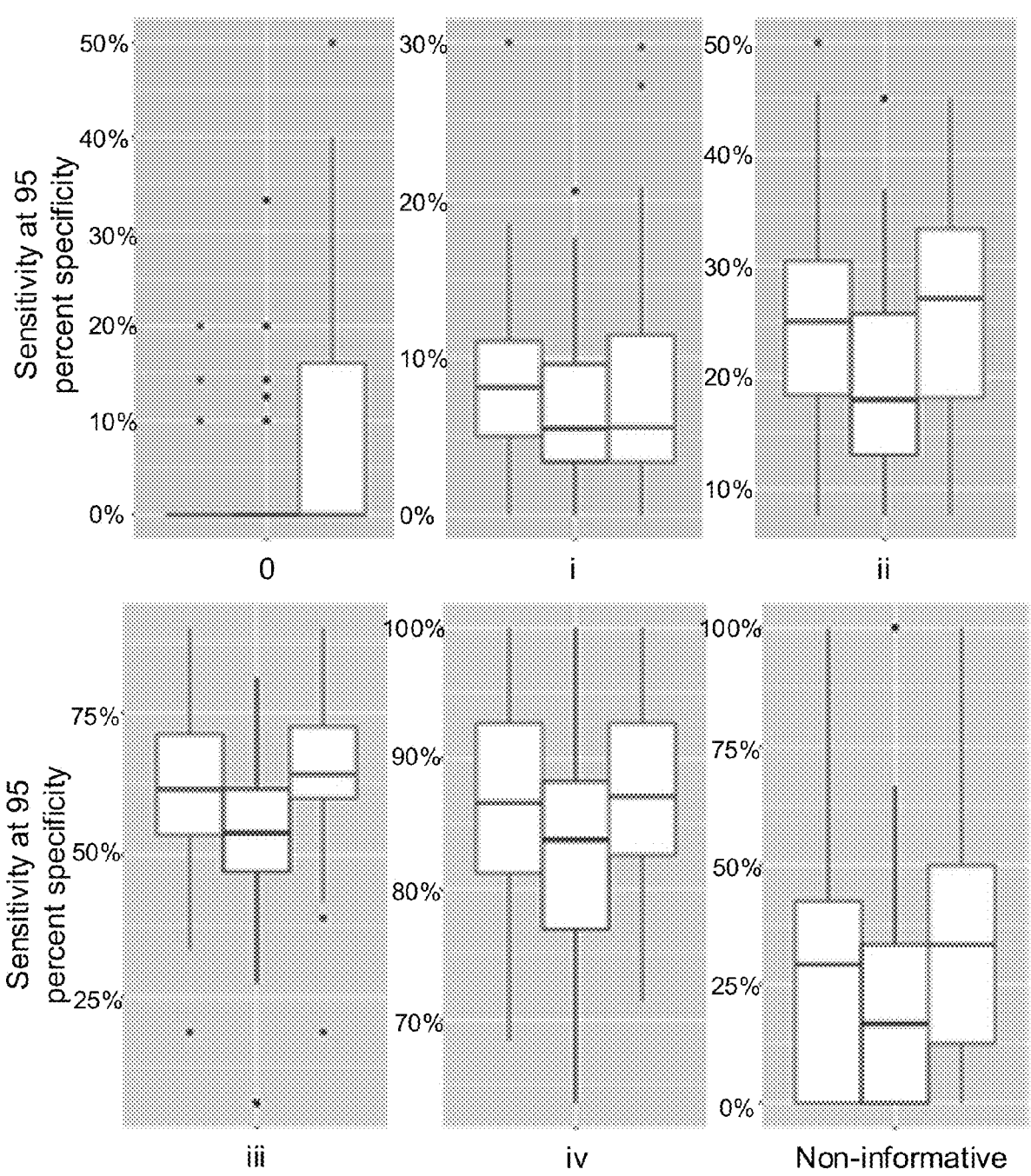
FIGS. 17C and 17D illustrate box plots of the specificity of cancer classification using full (unfiltered) CCGA WGS data sets, size-selected (filtered) CCGA WGS data sets, and control data sets with randomly selected sequence reads from the full (unfiltered) CCG AWGS data sets to match the sequence coverage of the seize-selected (filtered) CCG AWGS data sets, for each cancer stage, as described in Example 7.
Figure 17D:
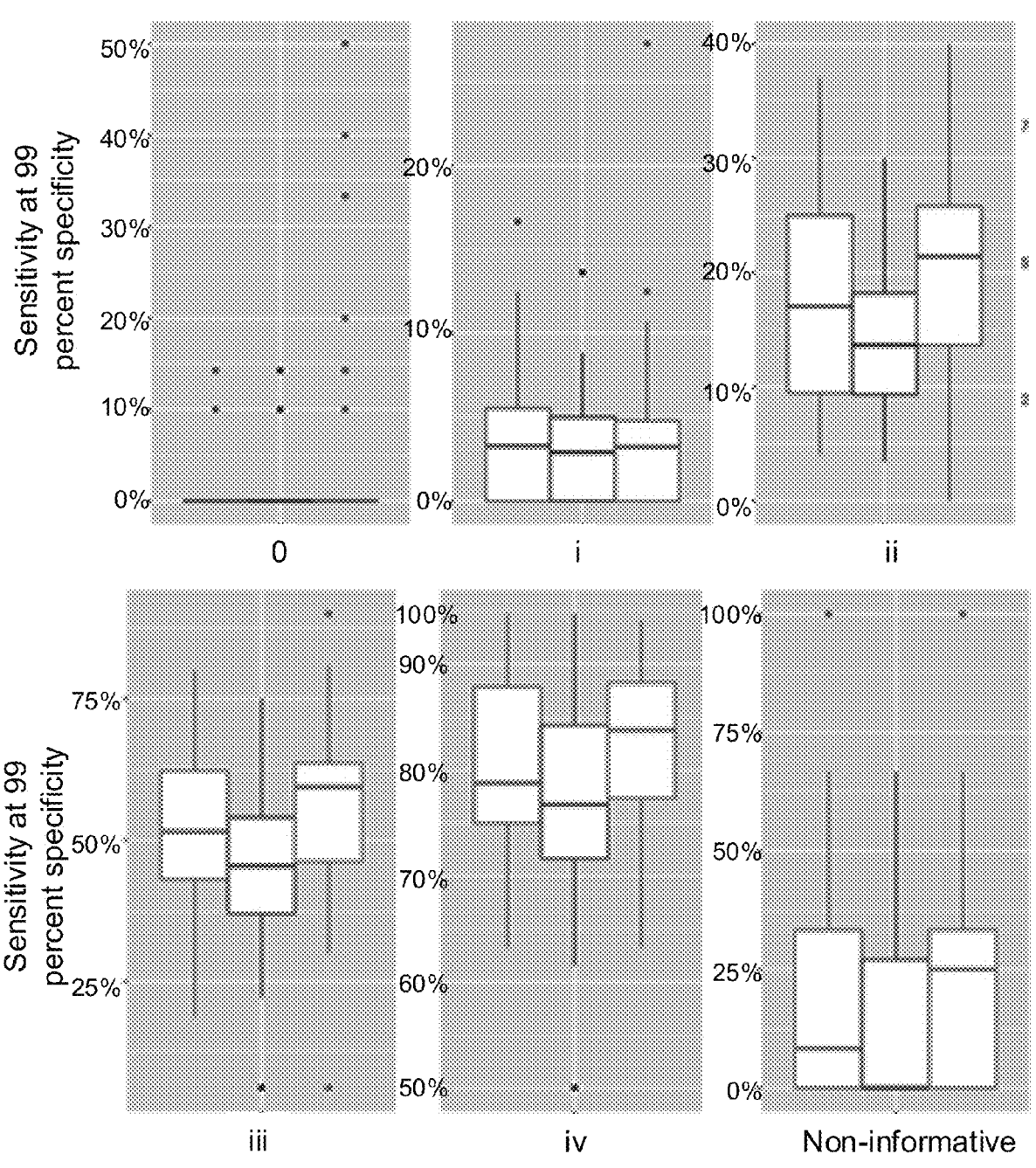

Next, the classification data generated for all cancers above was analyzed with respect to the stage of the cancer. As shown in FIGS. 17C (95% specificity) and 17D (99% specificity), the size-selected data provided equivalent or better sensitivity than the sequence coverage-matched control data sets for all cancer stages at both 95% and 98% specificity. Significantly, the size-selected data provided equivalent or better sensitivity than the full data sets for all cancer stages at both specificities, except for stage 1 cancers determined at 95% specificity. The classification statistics for this analysis are shown in FIG. 17E.

Figure 17F:
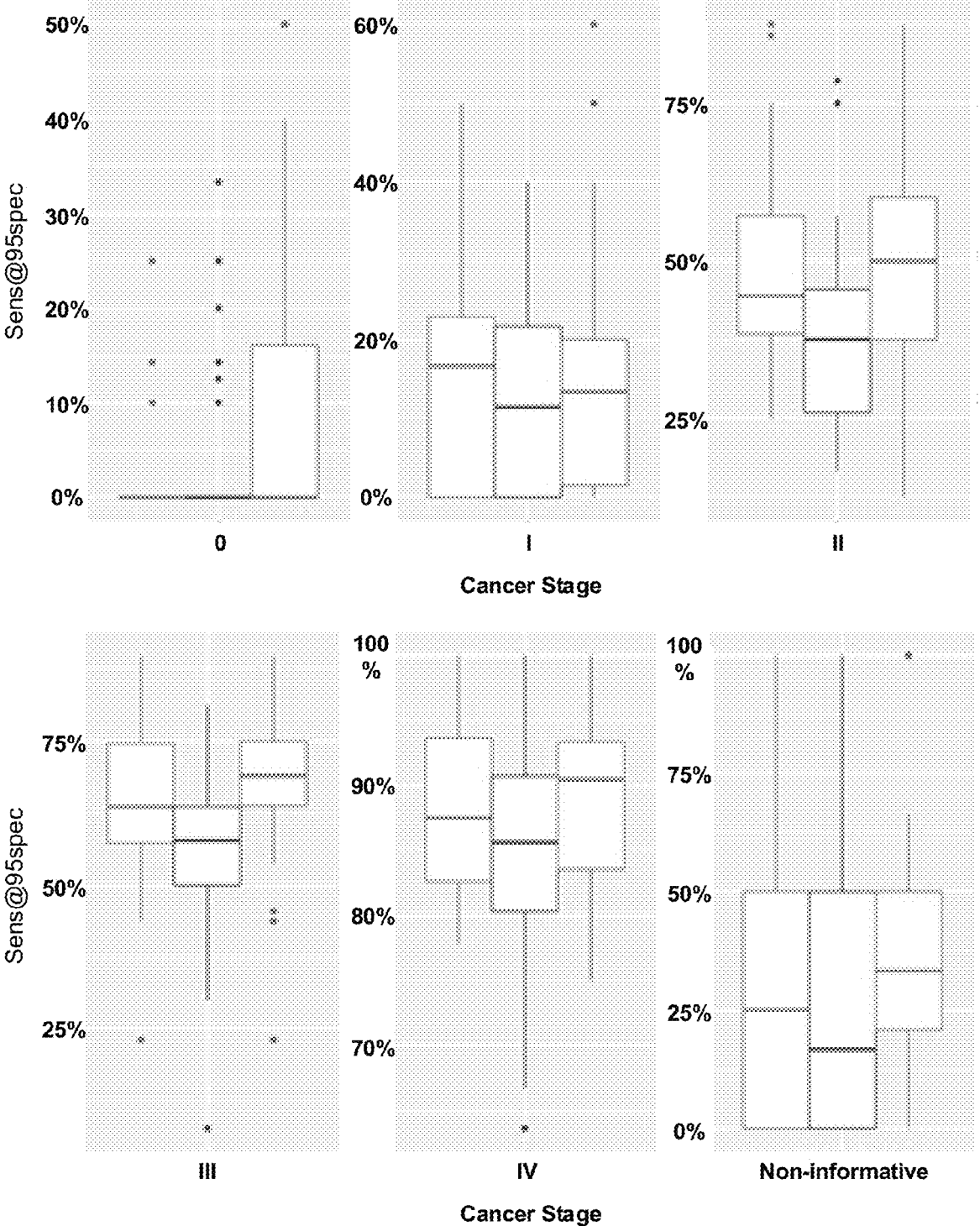
FIGS. 17F and 17G illustrate box plots of the specificity of cancer classification using full (unfiltered) CCGA WGS data sets, size-selected (filtered) CCGA WGS data sets, and control data sets with randomly selected sequence reads from the full (unfiltered) CCG AWGS data sets to match the sequence coverage of the seize-selected (filtered) CCG AWGS data sets, for each cancer stage of cancers that tend to shed into the bloodstream, as described in Example 7.
Figure 17G:
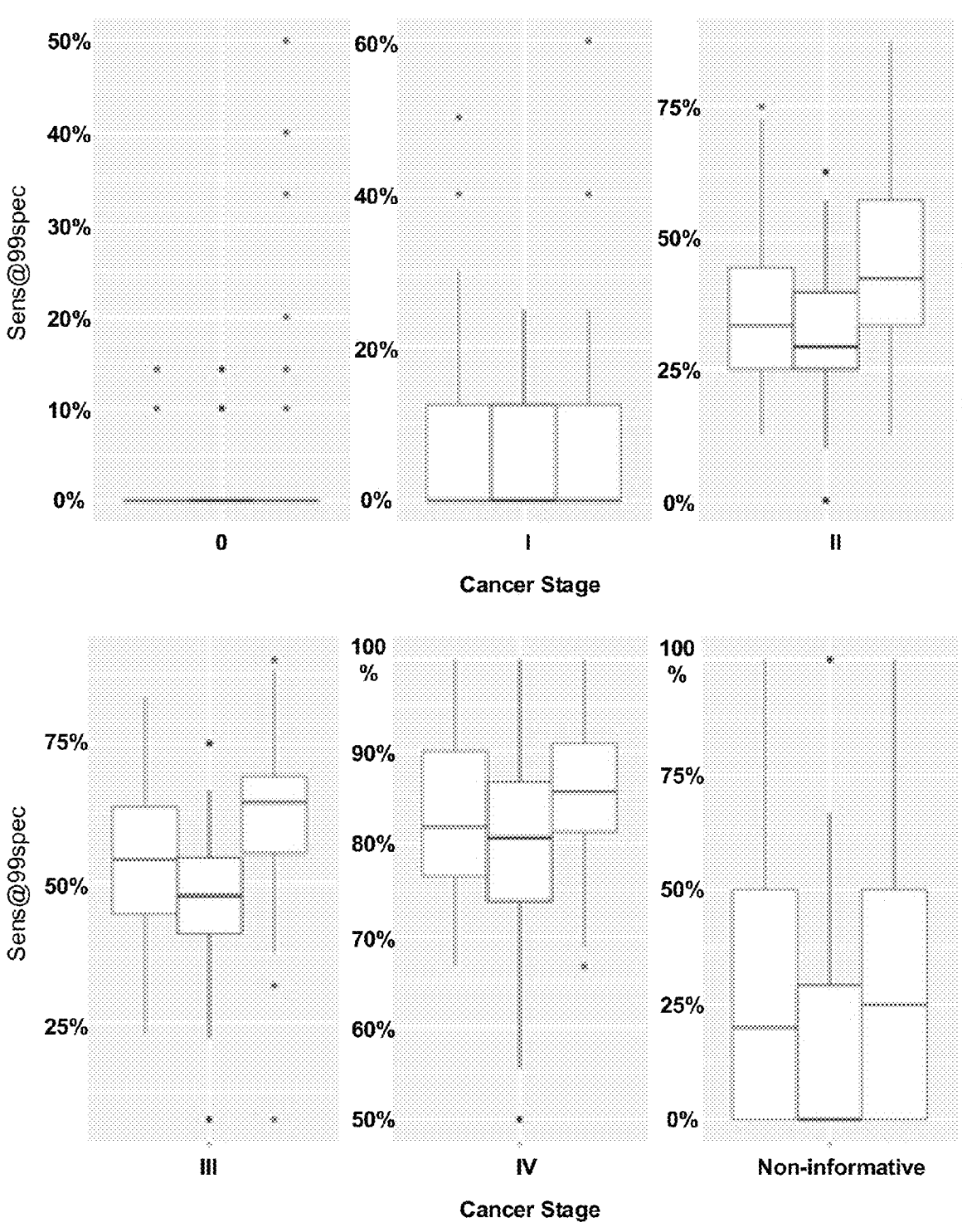

Next, the classification data generated for cancers that are more likely to shed into the blood as cell-free nucleic acids, e.g., excluding uterine, thyroid, prostate, melanoma, renal, and HR+ breast cancers, above was analyzed with respect to the stage of the cancer. As shown in FIGS. 17F (95% specificity) and 17G (99% specificity), the size-selected data provided equivalent or better sensitivity than the sequence coverage-matched control data sets for all cancer stages at both 95% and 98% specificity. Significantly, the size-selected data provided equivalent or better sensitivity than the full data sets for all cancer stages at both specificities, except for stage 1 cancers determined at 95% specificity. The classification statistics for this analysis are shown in FIG. 17H.

Example 8

In Vitro Size-Selection

Figure 18:
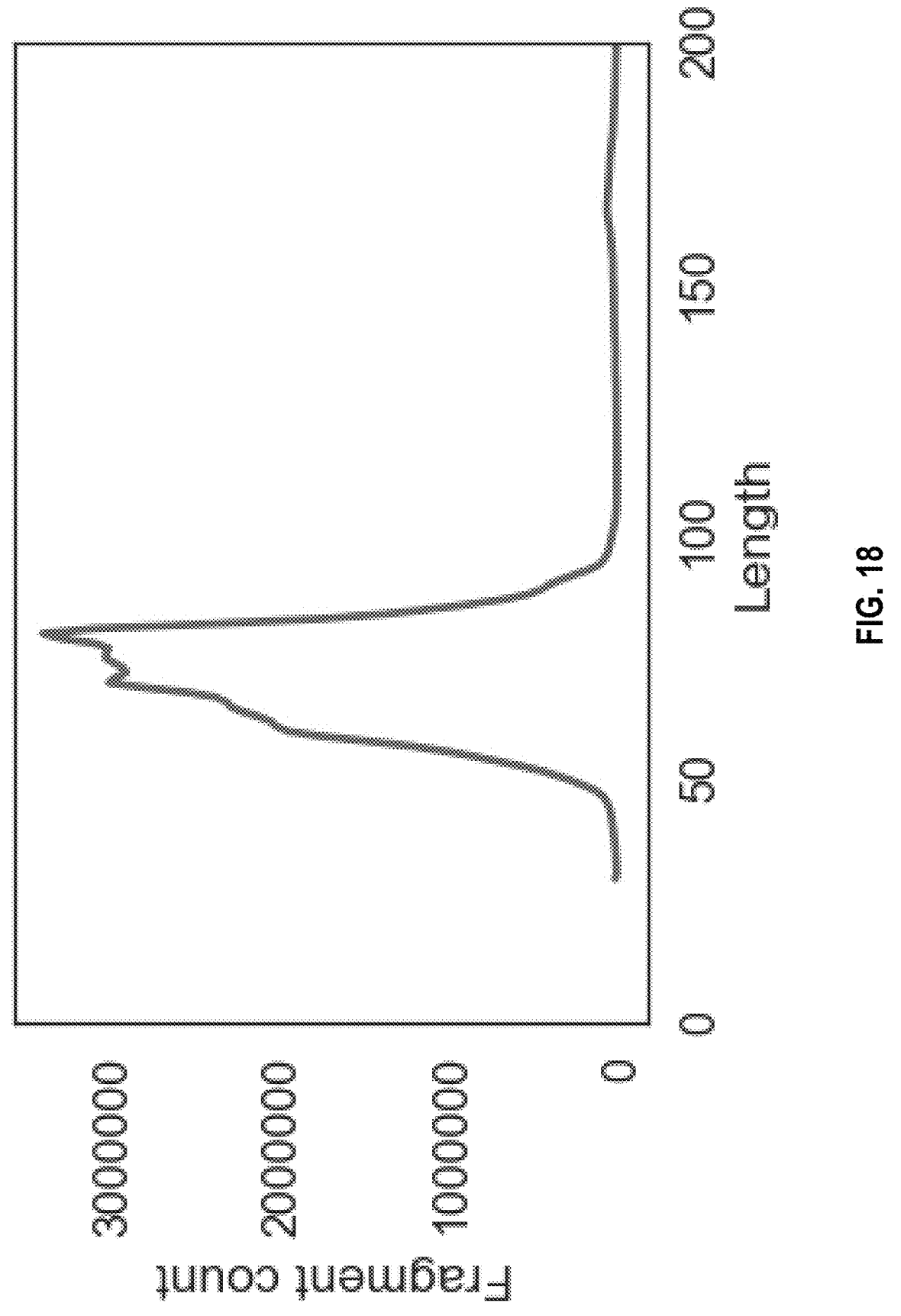
FIG. 18 illustrates the fragment count generated following in vitro size selection of a cfDNA library, as described in Example 8.

It was next determined whether in vitro size selection of DNA fragments prior to sequencing might be a viable alternative to in silico filtering after sequencing. Briefly, a cfDNA library was prepared from a cfDNA sample obtained from a healthy subject with tumor-derived cfDNA titrated in, e.g., as described above with reference to FIG. 13. The DNA fragments in the cfDNA library were then size selected using a Pipen Prep® agarose gel electrophoretic-based size selection instrument (Sage Science) set at a base pair target value of 0-100+x nucleotides, where x is the number of nucleotides added to the cfDNA fragment during library preparation. The size selected fragments were then sequenced by WGS. As shown in FIG. 18, the generated sequence reads show an appropriate size selection and a sharp cut-off at about 100 nucleotides. Further, when the sequence reads were analyzed, an enrichment in sequence reads of the tumor-derived cfDNA were observed, similar to the in silico size-selection results. Further, other sequencing metrics, e.g., duplication rate and total read loss, were similar to the metrics observed without in vitro size selection.

Example 9

Tumor Fraction Determination Following In Vitro Size-Selection

It was next asked whether in vitro size-selection of DNA fragments, prior to sequencing, would provide a similar improvement in classification sensitivity as the in silico size-selection of sequence reads provided in Examples 5 and 7. Briefly, 65 cancer samples and 29 non-cancer samples were selected from collected CCGA samples across a variety of cancers and cancer stages, as shown in Tables 2 and 3. 38 of the selected cancers were shown to shed more into the bloodstream.

TABLE 2

| Cancer stage of the samples used in the in vitro size selection studies. | |
|---|---|
| Stage | Count |
| I | 13 |
| II | 15 |

TABLE 2-continued

| Cancer stage of the samples used in the in vitro size selection studies. | |
| --- | --- |
| Stage | Count |
| III | 21 |
| IV | 12 |
| Non-informative | 4 |

TABLE 3

| Cancer type of the samples used in the in vitro size selection studies. | | | |
| --- | --- | --- | --- |
| Type | Count | Type | Count |
| Breast | 18 | Hepatobiliary | 3 |
| Colorectal | 13 | Lymphoma | 3 |
| Lung | 6 | Pancreas | 3 |
| Renal | 5 | Cervix | 2 |
| Head/Neck | 3 | Other | 9 |

Briefly, cfDNA libraries were prepared from the selected samples, as described above with reference to FIG. 13. Adapters containing UMI sequences, primer hybridization sites, etc., added to the fragments increased the lengths of the cfDNA fragments by approximately 170 nucleotides. In vitro size selection was then performed according to standard protocols using a Pipen Prep® instrument (Sage Science), set to select a size range of either 200-310 nucleotides or 200-320 nucleotides, representing cfDNA fragments of 30-140 or 30-150 nucleotides ligated to 3' and 5' adaptors totaling 170 nucleotides. Sequence reads were then generated for the size-selected libraries, as described above with reference to FIG. 13.

The fraction of sequence reads from cancer-derived cfDNA fragments was then estimated using cancer-derived variant detection. As discussed above, sequencing reactions were performed for cfDNA samples of each of the 65 cancer subjects with and without in vitro size selection either between 30-140 nucleotides or 30-150 nucleotides. Sequencing reactions were also performed against genomic DNA preparations of tumor-matched samples from each of the 35 cancer subjects. The fraction of cancer-derived sequence reads was then estimated by comparing cancer-derived variant alleles identified in the tumor-matched sample with sequence reads of the cell-free DNA either from the size-selected sample or following in silico size selection. As shown in FIG. 19, in vitro size selection to a range of either 30-140 (orange) or 30-150 (blue) nucleotides increased the estimated tumor fraction of almost every sample. In several cases, the increase resulted in a tumor fraction that is above a level of detection for the whole genome sequencing classifier, estimated to be about 0.5%, denoted as the dashed line in the FIG. 19. Tables 4 and 5, below, show the fold improvement in samples grouped by original tumor fraction and cancer stage, respectively.

TABLE 4

| Median improvement in tumor fraction following in vitro size selection grouped by the original tumor fraction of the sample. | |
| --- | --- |
| Original TF | Median fold improvement |
| <=0.005 | 2.24 |
| <=0.01 | 2.38 |

TABLE 4-continued

| Median improvement in tumor fraction following in vitro size selection grouped by the original tumor fraction of the sample. | |
| --- | --- |
| Original TF | Median fold improvement |
| <=0.05 | 2.00 |
| <=0.1 | 1.78 |
| <=0.2 | 1.45 |
| <=0.5 | 1.41 |

TABLE 5

| Median improvement in tumor fraction following in vitro size selection grouped by cancer stage. | |
| --- | --- |
| Stage | Median fold improvement |
| I | 1.89 |
| II | 2.12 |
| III | 2.24 |
| IV | 1.58 |
| NI | 2.24 |

Example 10

Classification Sensitivity Improvement Following In Vitro Size-Selection

Figure 20:
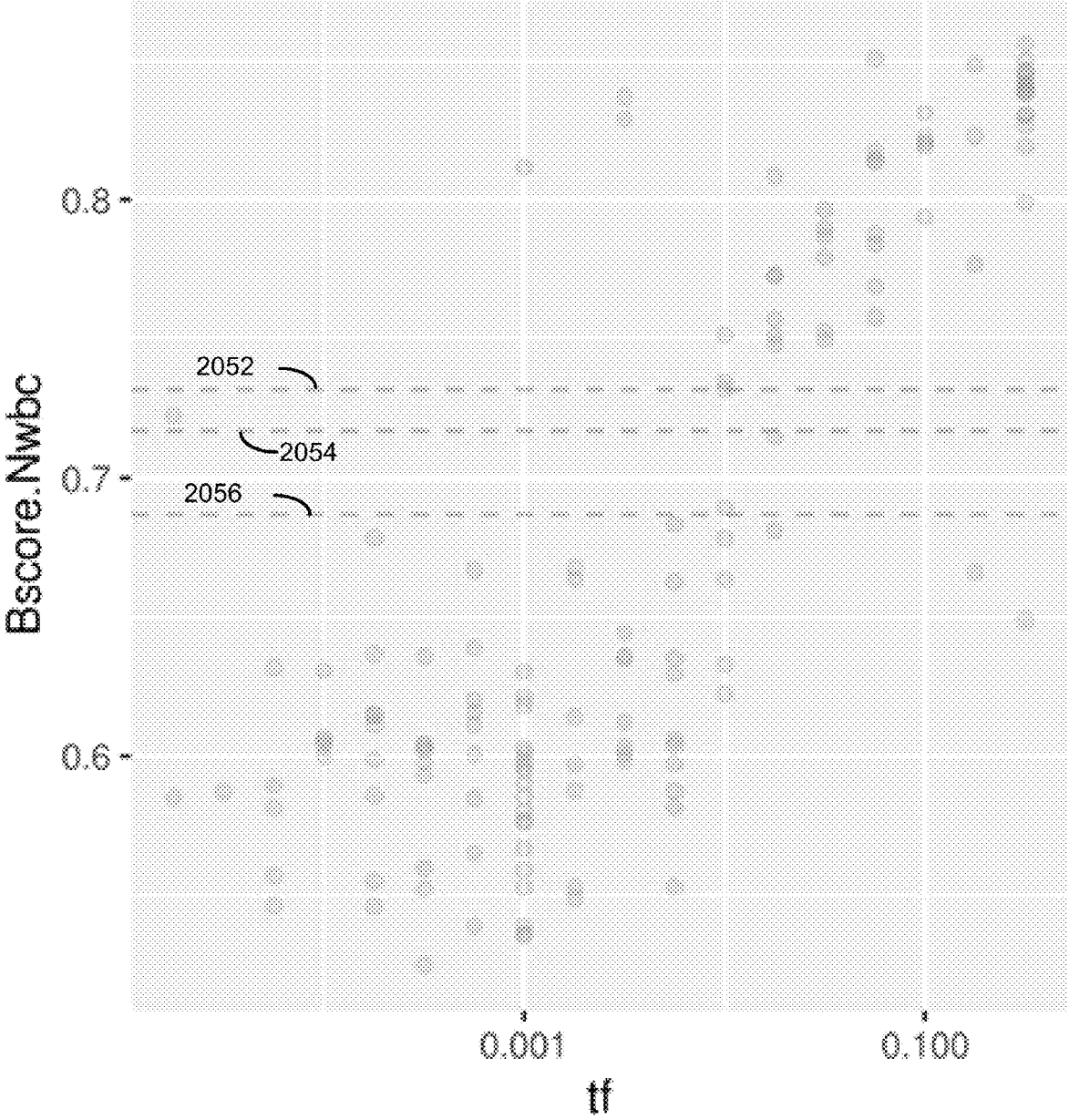
FIG. 20 illustrates classification scores generated using sequence reads from full cfDNA samples and in vitro size-selected cfDNA samples, plotted as a function of the original tumor fraction of the sample, as described in Example 10.

The sequence read data sets generated on the full cfDNA samples and on the cfDNA samples following in vitro size selection from all 65 cancer samples were input into a cancer classifier trained against copy number variation across a plurality of predetermined genomic bins, each representing a predefined portion of the human genome having low variability across the genomes of healthy subjects, as described above, to generate a 'B-score' for each data set. The resulting classification scores (cancer=orange; non-cancer=blue) were then plotted against the original tumor fraction of the sample, as shown in FIG. 20. Specificities of 95% (2156), 98% (2154), and 99% (2152) were determined based on the classification scores and the tumor fraction of samples at those classification scores were determined to be LOD levels. The sensitivities of the classifications using the full data sets or the in vitro size-selected data set were then estimated at each specificity based on the determined LOD levels. As reported in Table 6, in vitro size selection of the cfDNA fragments improved the sensitivity of the assay by about 20-30% at all three specificities.

TABLE 6

| Classification sensitivity following in vitro size selection. | | | | |
| --- | --- | --- | --- | --- |
| Specificity | Median TF in ($p - \delta$, $p + \delta$) | Original sensitivity | In vitro sensitivity | Ratio |
| 95% | 0.008 | 0.46 | 0.56 | 1.22 |
| 98% | 0.010 | 0.46 | 0.54 | 1.18 |
| 99% | 0.014 | 0.39 | 0.51 | 1.30 |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features, and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still, further variations and alternate elements will be apparent to one of skill in the art.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

We claim:

1. A method of analyzing sequence reads of nucleic acid samples in connection with a cancer condition, comprising:

receiving, at a data collection component of a computer system, a first set of sequence reads of the nucleic acid samples from each healthy subject in a reference group of healthy subjects, wherein the nucleic acid samples comprise a set of cell-free DNA (cfDNA) fragments and wherein the first set of sequence reads is derived from a DNA sequencing process and wherein the first set of sequence reads are not known to contain one or more mutations indicative of the cancer condition;

aligning, using a processor of the computer system, each sequence read in the first set of sequence reads to regions in a reference genome;

establishing, using the processor and subsequent to the aligning, a low variability filter, wherein the establishing comprises:

identifying, using the processor, numbers of sequence reads aligned to each of the regions in the reference genome across each healthy subject in the reference group of healthy subjects;

deriving, using the processor and based on the identifying, quantity data associated with each of the regions based on the numbers of sequence reads;

calibrating, using the processor, the quantity data for each of the regions;

computing, using the processor, reference quantities for each of the regions based on the calibrated quantity data, wherein the reference quantities comprise at least a first reference quantity and a second reference quantity, wherein the first reference quantity corresponds to an average of the calibrated quantity data and wherein the second reference quantity is a standard deviation of the calibrated quantity data;

determining, using the processor, a difference between the first reference quantity and the second reference quantity for each of the regions;

classifying each of the regions as a high variability region or a low variability region by comparing the difference against a predetermined threshold, wherein the high variability region is defined by the difference being greater than the predetermined threshold and wherein the low variability region is defined by the difference between less than the predetermined threshold;

receiving, at the data collection component, a training set of sequence reads from subjects in a training group, wherein the training set includes a second set of sequence reads of nucleic acid samples from healthy subjects and a third set of sequence reads of nucleic acid samples from cancer subjects who are known to have the cancer condition, wherein the second set of sequence reads of nucleic acid samples are not known to contain the one or more mutations indicative of the cancer condition and wherein the third set of sequence reads of nucleic acid samples do contain the one or more mutations indicative of the cancer condition and wherein the training set of sequence reads from the subjects in the training group comprise cfDNA fragments of varying length;

applying, using the processor, the established low variability filter to the training set of sequence reads;

generating, using the processor and based on the applying, a filtered training set of sequence reads, wherein the generating the filtered training set of sequence reads comprises discarding one or more sequence reads in the training set of sequence reads that are aligned to the high variability region in the reference genome training, using the processor, a machine learning model on the filtered training set of sequence reads;

applying, using the processor, a predictive capability of the trained machine learning model to identify differences between the second set of sequence reads of nucleic acid samples from the healthy subjects and the third set of sequence reads of nucleic acid samples from the cancer subjects.

2. The method of claim 1, wherein the cancer condition is a cancer type selected from the group consisting of lung cancer, ovarian cancer, kidney cancer, bladder cancer, hepato-biliary cancer, pancreatic cancer, upper gastrointestinal cancer, sarcoma, breast cancer, liver cancer, prostate cancer, brain cancer, and combinations thereof.

3. The method of claim 1, further comprising: performing initial data processing of the first set of sequence reads of nucleic acid samples from each healthy subject in the reference group of healthy subjects based on a fourth set of sequence reads of nucleic acid samples from a baseline group of healthy subjects, wherein the reference group and the baseline group do not overlap, and wherein the initial data processing comprises correction of GC biases or normalization of numbers of sequence reads that align to regions of the reference genome.

4. The method of claim 1, further comprising: performing initial data processing of the sequence reads of nucleic acid samples from each subject in the training group based on a fourth set of sequence reads of nucleic acid samples from a baseline group of healthy subjects, wherein the baseline group and the training group do not overlap, and wherein the initial data processing comprises correction of GC biases or normalization of numbers of sequence reads aligned to regions of the reference genome.

5. The method of claim 1, wherein the quantity data consists of one quantity corresponding to a total number of sequence reads that align to the low variability region.

6. The method of claim 1, wherein the quantity data comprises multiple quantities each corresponding to a subset of the sequence reads that align to the low variability region, wherein each sequence read within a same subset corresponds to nucleic acid samples having a same predetermined fragment size or size range, wherein sequence reads in different subsets correspond to nucleic acid samples having a different fragment size or size range.

7. The method of claim 1, wherein the one or more parameters are determined by principal component analysis (PCA).

8. The method of claim 1, further comprising: refining the one or more parameters in a multi-fold cross-validation process by dividing the second filtered training set of sequence reads into a filtered training subset and a filtered validation subset.

9. The method of claim 8, wherein the filtered training and validation subsets in one fold of the multi-fold cross-validation process are different from another filtered training and validation subset in another fold of the multi-fold cross-validation process.

10. The method of claim 1, wherein the high variability region in the reference genome corresponds to a plurality of regions in the reference genome that exhibit variability above the predetermined threshold and wherein each of the plurality of regions has the same size.

11. The method of claim 1, wherein the high variability region in the reference genome includes a plurality of high variability regions that correspond to a plurality of regions in the reference genome that exhibit variability above the predetermined threshold and wherein each of the plurality of regions do not have the same size.

12. The method of claim 1, wherein the one or more parameters are determined based on a subset of the training set of sequence reads.

13. The method of claim 1, wherein the nucleic acid samples from the subjects in the training group comprise cfDNA fragments that are longer than the predetermined threshold length, wherein the predetermined threshold length is less than 160 nucleotides.

14. The method of claim 13, wherein the predetermined threshold length is 140 nucleotides or less.

15. The method of claim 13, wherein the sequence reads in the training set includes sequence reads of cfDNA fragments in the nucleic acid samples from the subjects in the training group having a length falling between a second threshold length and a third threshold length, wherein: the second threshold length is from 240 to 260 nucleotides, and the third threshold length is from 290 nucleotides to 310 nucleotides.

16. A computer system comprising: one or more processors; and a non-transitory computer-readable medium including one or more sequences of instructions that, when executed by the one or more processors, cause the processors to receive, at a data collection component of the computer system, a first set of sequence reads of nucleic acid samples from each healthy subject in a reference group of healthy subjects, wherein the nucleic acid samples comprise cell-free DNA (cfDNA) fragments and wherein the first set of sequence reads is derived from a DNA sequencing process and wherein the first set of sequence reads are not known to contain one or more mutations indicative of a cancer condition;

align, using the one or more processors, each sequence read in the first set of sequence reads to regions in a reference genome;

establish, using the one or more processors and subsequent to the aligning, a low variability filter, wherein the instructions to establish comprise instructions to:

identify, using the one or more processors, numbers of sequence reads aligned to each of the regions in the reference genome across each healthy subject in the reference group of healthy subjects;

derive, using the one or more processors and based on the identifying, quantity data associated with each of the regions based on the numbers of sequence reads;

calibrate, using the one or more processors, the quantity data for each of the regions;

compute, using the one or more processors, reference quantities for each of the regions based on the calibrated quantity data, wherein the reference quantities comprise at least a first reference quantity and a second reference quantity, wherein the first reference quantity corresponds to an average of the calibrated quantity data and wherein the second reference quantity is a standard deviation of the calibrated quantity data;

determine, using the one or more processors, a difference between the first reference quantity and the second reference quantity for each of the regions;

classify, using the one or more processors, each of the regions as a high variability region or a low variability region by comparing the difference against a predetermined threshold, wherein the high variability region is defined by the difference being greater than the predetermined threshold and wherein the low variability region is defined by the difference between less than the predetermined threshold;

receive, at the data collection component, a training set of sequence reads from subjects in a training group, wherein the training set includes a second set of sequence reads of nucleic acid samples from healthy subjects and a third set of sequence reads of nucleic acid samples from cancer subjects who are known to have a cancer condition, wherein the second set of sequence reads of nucleic acid samples are not known to contain the one or more mutations indicative of the cancer condition and wherein the third set of sequence reads of nucleic acid samples do contain the one or more mutations indicative of the cancer condition and wherein the training set of sequence reads from the subjects in the training group comprise cfDNA fragments of varying length;

apply, using the one or more processors, the established low variability filter to the training set of sequence reads;

generate, using the one or more processors and based on the applying, a filtered training set of sequence reads, wherein the instructions to generate the filtered training set of sequence reads comprise instructions to discard one or more sequence reads in the filtered training set of sequence reads that are aligned to the high variability region in the reference genome;

training, using the processor, a machine learning model on the filtered training set of sequence reads;

applying, using the processor, a predictive capability of the trained machine learning model to identify differences between the second set of sequence reads of nucleic acid samples from the healthy subjects and the third set of sequence reads of nucleic acid samples from the cancer subjects.

17. A non-transitory computer-readable storage medium having stored thereon program code instructions that, when executed by a processor of a computer system, cause the computer system to perform a method comprising:

receiving, at a data collection component of a computer system, a first set of sequence reads of nucleic acid samples from each healthy subject in a reference group of healthy subjects, wherein the nucleic acid samples comprise a first set of cell-free DNA (cfDNA) fragments and wherein the first set of sequence reads is derived from a DNA sequencing process and wherein the first set of sequence reads are not known to contain one or more mutations indicative of a cancer condition;

aligning, using a processor of the computer system, each sequence read in the first set of sequence reads to regions in a reference genome;

establishing, using the processor and subsequent to the aligning, a low variability filter, wherein the establishing comprises:

identifying, using the processor, numbers of sequence reads aligned to each of the regions in the reference genome across each healthy subject in the reference group of healthy subjects;

deriving, using the processor and based on the identifying, quantity data associated with each of the regions based on the numbers of sequence reads;

calibrating, using the processor, the quantity data for each of the regions;

computing, using the processor, reference quantities for each of the regions based on the calibrated quantity data, wherein the reference quantities comprise at least a first reference quantity and a second reference quantity, wherein the first reference quantity corresponds to an average of the calibrated quantity data and wherein the second reference quantity is a standard deviation of the calibrated quantity data;

determining, using the processor, a difference between the first reference quantity and the second reference quantity for each of the regions;

classifying each of the regions as a high variability region or a low variability region by comparing the difference against a predetermined threshold, wherein the high variability region is defined by the difference being greater than the predetermined threshold and wherein the low variability region is defined by the difference between less than the predetermined threshold;

receiving, at the data collection component, a training set of sequence reads from subjects in a training group, wherein the training set includes a second set of sequence reads of nucleic acid samples from healthy subjects and a third set of sequence reads of nucleic acid samples from cancer subjects who are known to have a cancer condition, wherein the second set of sequence reads of nucleic acid samples are not known to contain the one or more mutations indicative of the cancer condition and wherein the third set of sequence reads of nucleic acid samples do contain the one or more mutations indicative of the cancer condition and wherein the training set of sequence reads from the subjects in the training group comprise cfDNA fragments of varying length;

applying, using the processor, the established low variability filter to the training set of sequence reads;

generating, using the processor and based on the applying, a filtered training set of sequence reads, wherein the generating the filtered training set of sequence reads comprises discarding one or more sequence reads in the filtered training set of sequence reads that are aligned to the high variability region in the reference genome;

training, using the processor, a machine learning model on the filtered training set of sequence reads;

applying, using the processor, a predictive capability of the trained machine learning model to identify differences between the second set of sequence reads of nucleic acid samples from the healthy subjects and the third set of sequence reads of nucleic acid samples from the cancer subjects.

* * * * *